United States Patent [19]
Rorer

[11] Patent Number: 4,784,684
[45] Date of Patent: Nov. 15, 1988

[54] HERBICIDAL PYRIDINESULFONAMIDES

[75] Inventor: Morris P. Rorer, Newark, Del.

[73] Assignee: E. I. Du Pont de Nemours and Company, Wilmington, Del.

[21] Appl. No.: 15,615

[22] Filed: Feb. 17, 1987

Related U.S. Application Data

[60] Division of Ser. No. 724,451, Apr. 22, 1985, Pat. No. 4,668,279, which is a continuation-in-part of Ser. No. 638,964, Aug. 8, 1984, abandoned.

[51] Int. Cl.[4] .................. A01N 43/66; C07D 251/18; C07D 401/14
[52] U.S. Cl. ........................................ 71/93; 544/182; 544/212; 544/207; 544/209; 544/219
[58] Field of Search .................... 71/93; 544/212, 207, 544/209, 219, 182

[56] References Cited

U.S. PATENT DOCUMENTS

| 4,378,991 | 4/1983 | Levitt | 71/93 |
| 4,456,469 | 6/1984 | Adams, Jr. | 71/93 |
| 4,460,401 | 7/1984 | Sauers | 71/92 |
| 4,465,505 | 8/1984 | Wolf | 71/92 |
| 4,511,392 | 4/1985 | Rorer | 71/90 |
| 4,544,401 | 10/1985 | Levitt | 71/92 |

FOREIGN PATENT DOCUMENTS

| 0013480 | 3/1983 | European Pat. Off. | |
| 103543 | 3/1984 | European Pat. Off. | 544/212 |
| 161211 | 11/1985 | European Pat. Off. | |
| 834305 | 2/1984 | South Africa | |
| 836639 | 2/1984 | South Africa | |

Primary Examiner—John M. Ford

[57] ABSTRACT

Novel pyridinesulfonamide compounds containing ortho-heterocyclic substituents such as N-[(4,6-dimethoxypyrimidin-2-yl)aminocarbonyl]-2-(1H-1,2,4-triazol-1-yl)-3-pyridinesulfonamide display utility as herbicides and plant growth regulants.

24 Claims, No Drawings

HERBICIDAL PYRIDINESULFONAMIDES

RELATED U.S. APPLICATION DATA

This application is a division of application Ser. No. 724,451, filed Apr. 22, 1985, now U.S. Pat. No. 4,668,279, which, in turn, is a continuation-in-part of prior application Ser. No. 638,964, filed Aug. 8, 1984, now abandoned.

BACKGROUND OF THE INVENTION

Herbicidal pyridinesulfonamides of the formula

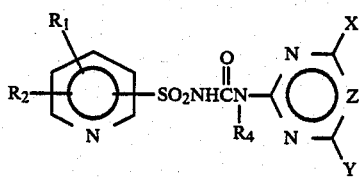

where
  $R_1$ is H, Cl, Br, F, $C_1$-$C_4$ alkyl, $C_1$-$C_4$ alkoxy, $C_1$-$C_4$ alkylthio, $NO_2$ or $CO_2R_5$; and
  $R_2$ is H, Cl, Br or $CH_3$;
are disclosed in European Patent Application (EP-A) No. 13,480.

EP-A No. 35,893 discloses herbicidal pyridinesulfonamides of formula

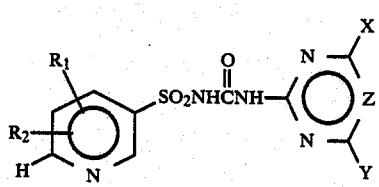

where
  $R_1$ is $S(O)_nR_3$; and
  $R_2$ is H, Cl, F, Br, $CH_3$, $OCH_3$, $CF_3$, $NO_2$, CN or $NH_2$.

EP-A No. 83,975 and EP-A No. 85,476 disclose herbicidal benzenesulfonamides of formula

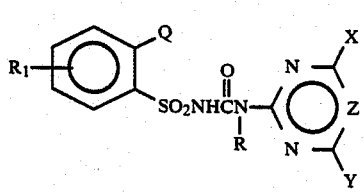

where
  Q is various saturated and unsaturated 5- and 6-membered heterocycles.

U.S. Pat. No. 4,378,991 discloses herbicidal benzenesulfonamides of formula

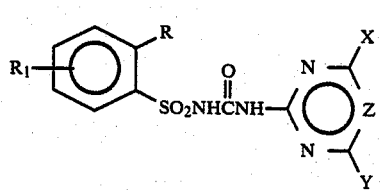

where
  R is, among other values, phenyl; and
  $R_1$ is H, F, Cl, Br, $NO_2$, $CF_3$, $C_1$-$C_4$ alkyl, $OCF_3$ or $C_1$-$C_4$ alkoxy.

EP-A No. 97,122, published Dec. 28, 1983, discloses herbicidal sulfonamides of formula

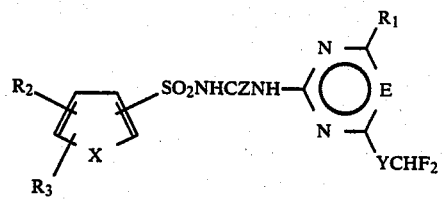

where
  X is O, S, $NR_4$ or $CR_5$=N; and
  $R_2$ is H, $C_1$-$C_3$ alkyl, haloalkyl, alkoxy, alkylthio, alkylsulfinyl or alkylsulphonyl, halogen, $NO_2$, $CWR_8$, $SO_2NR_6R_7$ or $COR_9$.

South African Patent Application No. 836,639 discloses herbicidal sulfonamides of formula

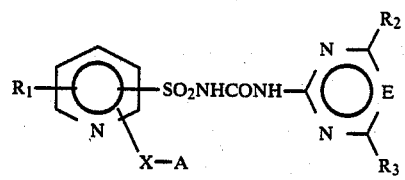

where
  X is O, S, SO, $SO_2$ or XA may form an amino radical $NR_6R_7$; and
  $R_1$ is H, halogen, $C_1$-$C_4$ alkyl, $C_1$-$C_4$ alkoxy, $C_1$-$C_4$ haloalkyl, $C_1$-$C_4$ haloalkoxy, $C_2$-$C_5$ alkoxyalkoxy, $C_1$-$C_5$ alkylthio, $C_1$-$C_5$ alkylsulfinyl or $C_1$-$C_5$ alkylsulfonyl.

SUMMARY OF THE INVENTION

This invention relates to compounds of Formulae I and II, agriculturally suitable compositions containing them and their method of use as preemergent and/or postemergent herbicides or plant growth regulants.

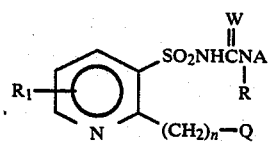 I

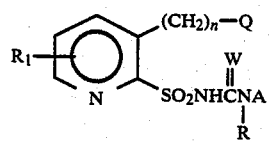 II wherein
  R is H or $CH_3$;
  $R_1$ is H, Cl, Br, $SCH_3$ or $CH_3$;
  n is 0, 1 or 2;
  W is O or S;
  Q is phenyl optionally substituted with Cl, $OCH_3$, or $CH_3$, a saturated 5- or 6-membered ring containing one heteroatom selected from O, S, or N, or an unsaturated 5- or 6-membered ring containing 1 to 3 heteroatoms selected from 0–1S, 0–1O or 0–3N and when Q is an unsaturated 5- or 6-membered ring, it may optionally be substituted by one or more groups selected from $C_1$–$C_4$ alkyl, halogen, $C_3$–$C_4$ alkenyl $C_1$–$C_3$ alkoxy, $C_1$–$C_3$ alkylthio, $C_3$–$C_4$ alkenylthio, $C_1$–$C_2$ haloalkoxy or $C_1$–$C_2$ haloalkylthio;

A is

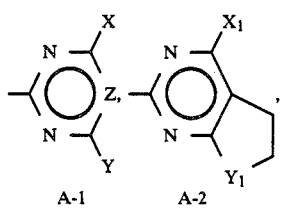
A-1    A-2

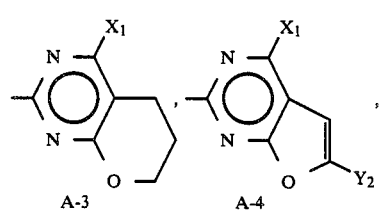
A-3    A-4

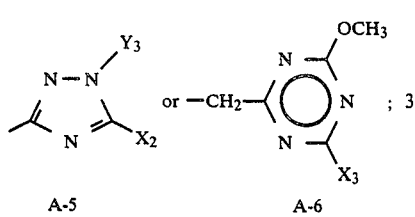
A-5    A-6

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$ or $CF_3$;

Y is H, $C_1$–$C_2$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$,

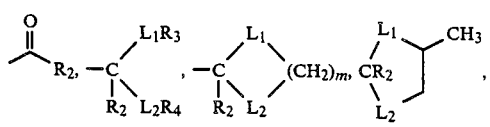

$OCF_2H$, $SCF_2H$ or cyclopropyl;
m is 2 or 3;
$L_1$ and $L_2$ are independently O or S;
$R_2$ is H or $CH_3$;
$R_3$ and $R_4$ are independently $C_1$–$C_2$ alkyl;
Z is CH or N;
$Y_1$ is O or $CH_2$;
$X_1$ is $CH_3$, $OCH_3$, $OC_2H_5$ or $OCF_2H$;
$Y_2$ is H or $CH_3$;
$X_2$ is $OCH_3$ $SCH_3$ or $CH_3$;
$Y_3$ is $CH_3$, $C_2H_5$ or $CH_2CF_3$; and
$X_3$ is $CH_3$ or $OCH_3$;
provided that
(a) when X is Cl, F, Br or I, then Z is CH and Y is $OCH_3$, $OC_2H_5$, $N(OCH_3)CH_3$, $NHCH_3$, $N(CH_3)_2$, $NH_2$ or $OCF_2H$;
(b) when Y is cyclopropyl, X is other than Cl, F, Br or I;
(c) when Q is 1H-1,2,4-triazol-1-yl, then Z is CH;

(d) when X or Y is $OCF_2H$, then Z is CH;
(e) when Q is a saturated 5- or 6-membered ring containing one nitrogen atom, it is bonded to the pyridine ring through carbon; and
(f) when W is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

;

and their agriculturally suitable salts.

Preferred for reasons of greater ease of synthesis and/or greater herbicidal efficacy are:

(1) Compounds of Formulae I and II wherein
R is H;
W is O;
Q is selected from the group consisting of

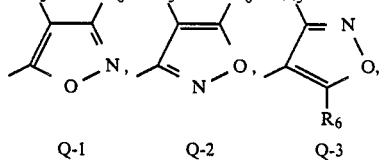
Q-1    Q-2    Q-3

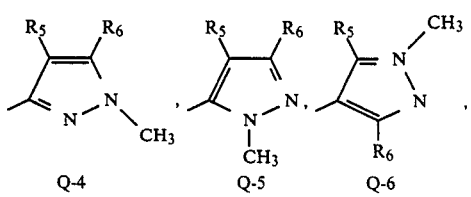
Q-4    Q-5    Q-6

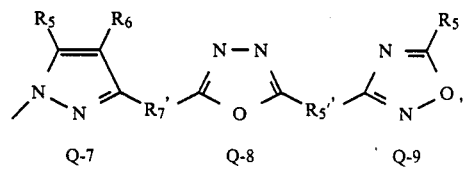
Q-7    Q-8    Q-9

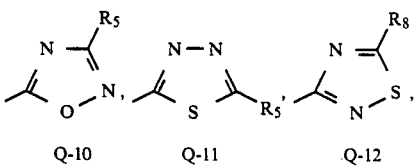
Q-10    Q-11    Q-12

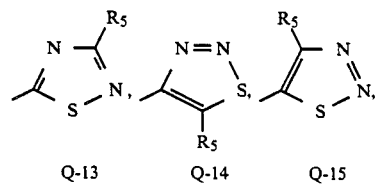
Q-13    Q-14    Q-15

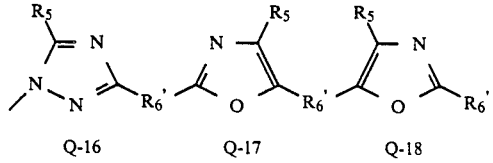
Q-16    Q-17    Q-18

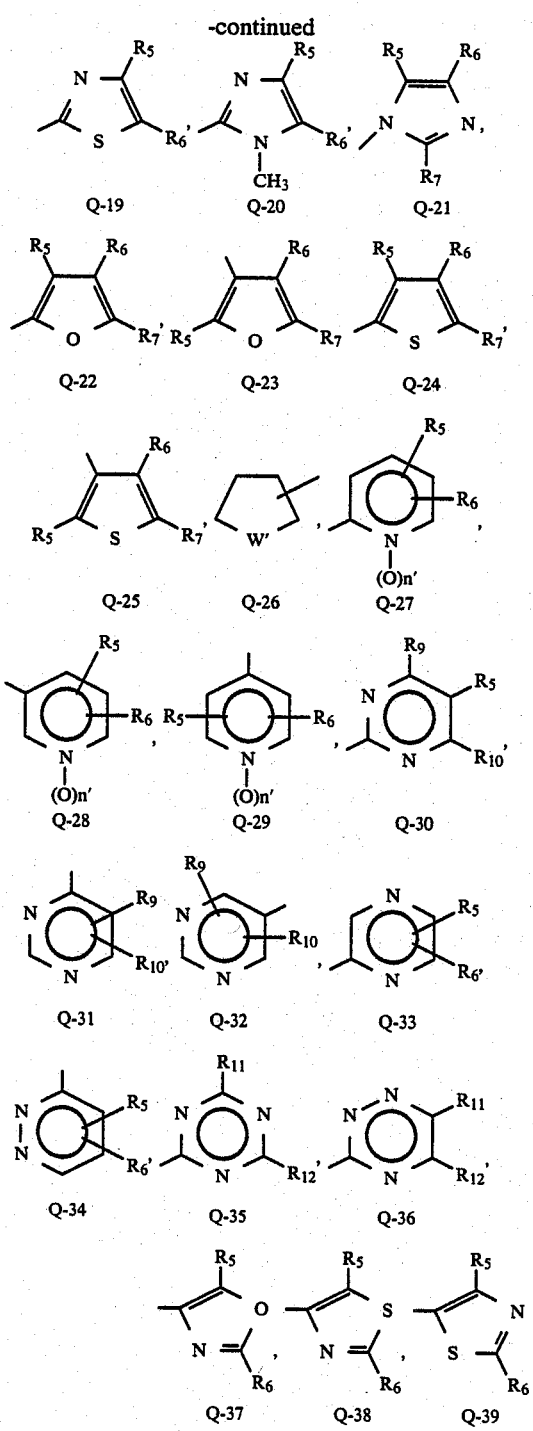

Q-16, Q-17, Q-18, Q-21, Q-22, Q-24, Q-27, Q-30, Q-33, Q-37, Q-38 and phenyl;

(3) Compounds of Preferred 2 where X is $CH_3$, $OCH_3$, $OCH_2CH_3$ or Cl, and Y is $CH_3$, $CH_2CH_3$, $OCH_3$, $OCF_2H$, $CH(OCH_3)_2$ or $CH_2OCH_3$;

(4) Compounds of Preferred 3 where n is O;

(5) Compounds of Preferred 4 where Y is $CH_3$, $CH_2CH_3$, $OCH_3$ or $OCF_2H$;

(6) Compounds of Preferred 5 of Formula I;

(7) Compounds of Preferred 5 of Formula II;

(8) Compounds of Preferred 6 where Q is Q-1;

(9) Compounds of Preferred 6 where Q is Q-2;

(10) Compounds of Preferred 6 where Q is Q-3;

(11) Compounds of Preferred 6 where Q is Q-4;

(12) Compounds of Preferred 6 where Q is Q-7;

(13) Compounds of Preferred 6 where Q is Q-8;

(14) Compounds of Preferred 6 where Q is Q-9;

(15) Compounds of Preferred 6 where Q is Q-10;

(16) Compounds of Preferred 6 where Q is Q-11;

(17) Compounds of Preferred 6 where Q is Q-14;

(18) Compounds of Preferred 6 where Q is Q-16;

(19) Compounds of Preferred 6 where Q is Q-17;

(20) Compounds of Preferred 6 where Q is Q-18;

(21) Compounds of Preferred 6 where Q is Q-21;

(22) Compounds of Preferred 6 where Q is Q-22;

(23) Compounds of Preferred 6 where Q is Q-24;

(24) Compounds of Preferred 6 where Q is Q-27;

(25) Compounds of Preferred 6 where Q is Q-30;

(26) Compounds of Preferred 6 where Q is Q-33;

(27) Compounds of Preferred 6 where Q is Q-37;

(28) Compounds of Preferred 6 where Q is Q-38;

(29) Compounds of Preferred 6 where Q is phenyl;

(30) Compounds of Preferred 7 where Q is Q-1;

(31) Compounds of Preferred 7 where Q is Q-2;

(32) Compounds of Preferred 7 where Q is Q-3;

(33) Compounds of Preferred 7 where Q is Q-4;

(34) Compounds of Preferred 7 where Q is Q-7;

(35) Compounds of Preferred 7 where Q is Q-8;

(36) Compounds of Preferred 7 where Q is Q-9;

(37) Compounds of Preferred 7 where Q is Q-10;

(38) Compounds of Preferred 7 where Q is Q-11;

(39) Compounds of Preferred 7 where Q is Q-14;

(40) Compounds of Preferred 7 where Q is Q-16;

(41) Compounds of Preferred 7 where Q is Q-17;

(42) Compounds of Preferred 7 where Q is Q-18;

(43) Compounds of Preferred 7 where Q is Q-21;

(44) Compounds of Preferred 7 where Q is Q-22;

(45) Compounds of Preferred 7 where Q is Q-24;

(46) Compounds of Preferred 7 where Q is Q-27;

(47) Compounds of Preferred 7 where Q is Q-30;

(48) Compounds of Preferred 7 where Q is Q-33;

(49) Compounds of Preferred 7 where Q is Q-37;

(50) Compounds of Preferred 7 where Q is Q-38;

(51) Compounds of Preferred 7 where Q is phenyl;

An exemplary compound within the scope of this invention is N-[(4,6-dimethoxypyrimidin-2-yl)aminocarbonyl]-2-(1H-1,2,4-triazol-1-yl)-3-pyridinesulfonamide, m.p. 235°–238° C.

and phenyl;
n' is 0 or 1;
$R_5$, $R_6$ and $R_7$ are independently H or $CH_3$;
$R_5'$ is H, $CH_3$, $C_2H_5$, $C_1$–$C_3$ alkylthio, $SCH_2CH=CH_2$, $SCF_2H$, $OCH_3$ or $OCH_2CH_3$;
$R_8$ is H or Cl;
$R_9$ and $R_{10}$ are independently H, $CH_3$ or $OCH_3$;
$R_{11}$ and $R_{12}$ are independently $CH_3$ or $OCH_3$;
W' is O, S or $NR_{13}$; and
$R_{13}$ is H, $C_1$–$C_3$ alkyl or $CH_2CH=CH_2$;

(2) Compounds of Preferred 1 where A is A-1; $R_1$ is H, n' is O and Q is selected from the group consisting of Q-1, Q-2, Q-3, Q-4, Q-7, Q-8, Q-9, Q-10, Q-11, Q-14,

DETAILED DESCRIPTION OF THE INVENTION

Synthesis

The compounds of Formulae I and II can be prepared by one or more of the methods shown below in Equations 1, 2 and 3.

As shown in Equation 1 below, the compounds of Formulae I and II (wherein W is O) can be prepared by treating 2-heterocyclic-3-pyridinesulfonamides or 3-heterocyclic-2-pyridinesulfonamides of Formula III with the methyl ester of a pyrimidine or triazine-carbamic acid of Formula IV in the presence of an equimolar quantity of trimethylaluminum.

Equation 1

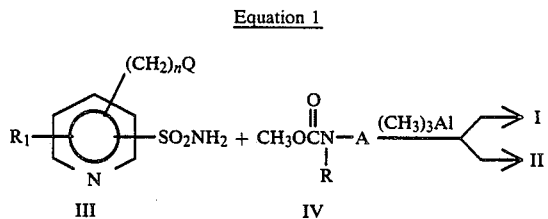

wherein

A, R, $R_1$, n and Q are as previously defined.

The reaction of Equation 1 is best carried out at temperaures between 23° and 83° C. in an inert solvent such as methylene chloride or 1,2-dichloroethane for 12 to 96 hours under an inert atmosphere. The product can be isolated by the addition of an aqueous acetic acid or hydrochloric acid solution followed by extraction of the product into methylene chloride or direct filtration of a product of low solubility. The product can ordinarily be purified by trituration with solvents such as n-butyl chloride, ethyl acetate or diethyl ether or by chromatography procedures. The methyl carbamates, IV, can be conveniently prepared by treatment of the corresponding heteroaromatic amines of Formula VII with dimethyl carbonate or methyl chloroformate in the presence of a base such as sodium hydride or pyridine.

Further details of this reaction and the preparation of the carbamates of Formula IV can be found in unexamined European Patent Application (EP-A) No. 83,975 (published July 20, 1983).

Alternatively, compounds of Formulae I and II (wherein W is O) can be prepared by the reaction of sulfonamides of Formula III with the phenyl ester of the appropriate carbamic acid, V, in the presence of an equimolar quantity of a tertiary amine base such as 1,8-diazabicyclo[5.4.0]undec-7-ene (DBU), as shown below in Equation 2.

Equation 2

$$\text{III} + \text{C}_6\text{H}_5\text{OC}\underset{\underset{\text{R}}{|}}{\overset{\overset{\text{O}}{\|}}{\text{N}}}-\text{A} \xrightarrow[(2) \text{H}_3\text{O}]{(1) \text{DBU}} \begin{matrix} \nearrow \text{I} \\ \searrow \text{II} \end{matrix}$$

V wherein

A and B are as previously defined.

The reaction of Equation 2 is carried out at 20° to 30° C. in an inert solvent such as dioxane or acetonitrile. Aqueous acid workup affords the desired products, according to the teachings of EP-A No. 70,804 (published Jan. 26, 1983) and South African Patent Application Nos. 825042 and 830441. The phenyl carbamates, V, can be prepared by treating the corresponding heteroaromatic amines of Formula VII with diphenyl carbonate or phenyl chloroformate in the presence of a base such as sodium hydride or pyridine.

Also, compounds of Formulae I and II (wherein W is O or S) may be prepared by reacting an appropriate 2-heterocyclic-3-pyridinesulfonyl isocyanate or 3-heterocyclic-2-pyridinesulfonyl isocyanate of Formula VI with the appropriately substituted aminoheterocycle, VII, as shown below in Equation 3.

Equation 3

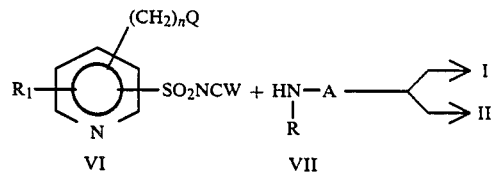

wherein

A, R, $R_1$, n and Q are as previously defined, and W is O or S.

The reaction is best performed in an inert solvent such as methylene chloride, tetrahydrofuran, acetonitrile or toluene at 23° to 100° C. for one to 24 hours. In cases where the products are insoluble in the reaction solvent, they may be isolated by simple filtration. When the product are soluble, they may be isolated by evaporation of the solvent and trituration of the residue with an inert solvent such as 1-chlorobutane, diethyl ether or ethyl acetate and filtration. The products may be further purified by column chromatography procedures or recrystallization.

Sulfonyl isocyanates of Formula VI above may be prepared, although often times in low yields, from corresponding sulfonamides of Formula II by methods analogous to those described in U.S. Pat. No. 4,238,621 and EP-A No. 83,975 (published July 20, 1983). Thus, by a preferred method, sulfonamides are reacted with phosgene, in the presence of n-butyl isocyanate and a tertiary amine catalyst, at reflux in an inert solvent such as xylenes. A preferred catalyst is 1,4-diazabicyclo[2.2.-2]octane (DABCO). Alternatively, isocyanates, VI, may be prepared by (1) reacting sulfonamides, III, with n-butyl isocyanate and a base such as potassium carbonate at reflux in an inert solvent such as 2-butanone to form a n-butylsulfonylurea; and (2) reacting this compound with phosgene and DABCO catalyst at reflux in xylenes solvent.

Sulfonyl isothiocyanates can be prepared by treatment of sulfonamides of Formula III with carbon disulfide and potassium hydroxide followed by reaction of the dipotassium salt with phosgene according to K. Hartke, Arch. Pharm., 299, 174 (1966).

2- and 3-Pyridinesulfonamides of Formula III above are important intermediates for the preparation of the compounds of this invention, and can be prepared by methods known in the literature, or simple modifications thereof, by those skilled in the art.

For example, 3-pyridinesulfonamides of Formula III, substituted in the 2-position with a pyrazol-1-yl, 1,2,4-triazol-1-yl or imidazol-1-yl group (Q is Q-7, Q-16 or Q-21) may be prepared by the sequence of reactions shown in Equation 4 below.

Equation 4

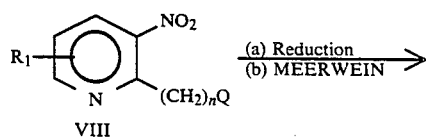

Equation 4
-continued

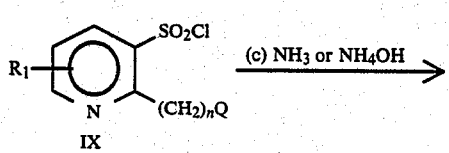

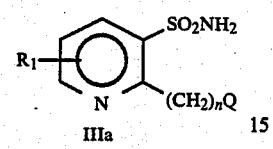

Equation 5

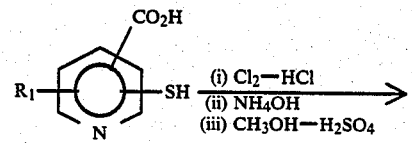

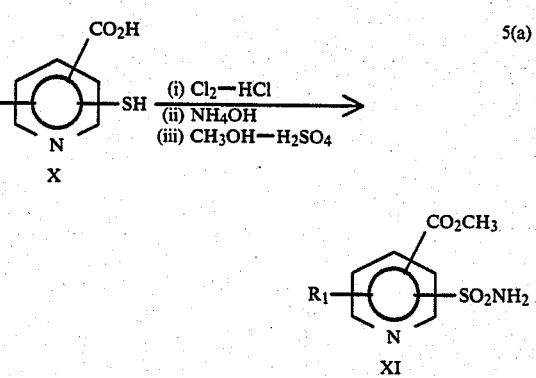

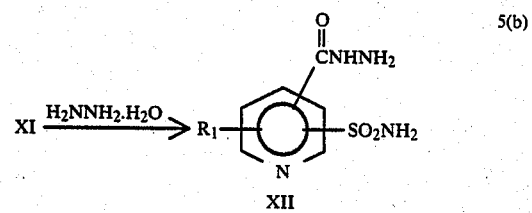

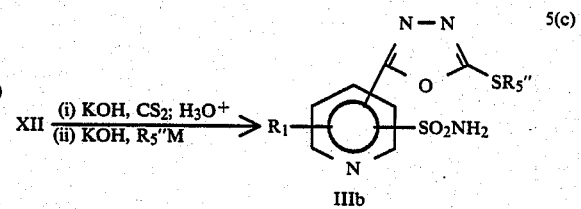

wherein
R₁ is as originally defined;
Q is Q-7, Q-16 or Q-21; and
n is 0, 1 or 2.

Reaction 4(a)

In this reaction 3-nitropyridines, VIII, are reduced to corresponding 3-aminopyridines, for example, by reaction with stannous chloride in hydrochloric acid by conventional methods. Details and references for this and other methods for reducing nitropyridines to corresponding aminopyridines can be found in "Pyridine and Derivatives", Chapter IX, pp. 8–10, E. Klingsberg, Ed., a part of the series "The Chemistry of Heterocyclic Compounds", A. Weissberger, Ed. The 3-nitropyridines, VIII, are prepared by reacting appropriate 2-chloro-3-nitropyridines with sodium salts of appropriate pyrazoles, 1,2,4-triazoles or imiazoles in an inert solvent such as N,N-dimethylformamide (DMF), according to the teachings of U.S. Pat. No. 3,489,761.

Reaction 4(b)

In this reaction 3-pyridinesulfonyl chlorides, IX, are prepared by the Meerwein reaction by diazotizing corresponding 3-aminopyridines with sodium nitrite in hydrochloric acid and acetic acid, and reacting the diazonium salts with excess sulfur dioxide in acetic acid in the presence of copper(I) chloride or copper(II) chloride catalyst. For details, refer to analogous reactions described in Y. Morisawa et al., *J. Med. Chem.*, 23, 1376 (1980), EP-A No. 83,975 and H. L. Hale and F. Sowinski, *J. Org. Chem.*, 25, 1824 (1960).

Reaction 4(c)

And in this reaction, sulfonyl chlorides, IX, are transformed to sulfonamides, IIIa, by reaction with anhydrous ammonia in an inert solvent such as tetrahydrofuran, or by reaction with aqueous ammonium hydroxide in an inert solvent such as tetrahydrofuran by conventional methods. For details, refer to analogous reactions described in references cited above for Reaction 4(b).

2- and 3-Pyridinesulfonamides of Formula III, substituted in the 3- and 2-positions respectively with 5-thiooxadiazol-2-yl groups (Q is Q-8), may be prepared from corresponding 2- and 3-mercaptopyridyl carboxylic acids, X, by the sequence of reactions shown below in Equation 5.

wherein
R₁ is as previously defined;
R₅″ is $C_1$–$C_3$ alkyl, $CH_2CH=CH_2$ or $CF_2H$; and
M is Cl, Br or I.

Reactions 5(a)

In these reactions pyridinesulfonamides, XI, are prepared by analogy with the teachings of Y. Morisawa et al., *J. Med. Chem.*, 23, 1376 (1980). The method comprises (i) chlorinated appropriate 2-carboxy-3-mercaptopyridines or 3-carboxy-2-mercaptopyridines in concentrated hydrochloric acid and water at about $-25°$ to $5°$ C. to form corresponding carboxypyridyl sulfonyl chlorides; (ii) aminating the isolated sulfonyl chlorides with concentrated ammonium hydroxide to form the corresponding carboxypyridylsulfonamides; and (iii) esterifying these compounds by refluxing in methanol with sulfuric acid catalyst to form sulfonamides, XI.

Alternatively, mercaptopyridines, X, may be chlorinated in the presence of potassium hydrogen difluoride in an inert solvent such as water and methanol at about $-30°$ to $0°$ C. to form the corresponding carboxypyridyl sulfonyl fluorides. Subsequent reaction of these compounds with ammonia can provide the corresponding sulfonamides. For further details refer to analogous reactions described in D. J. Brown and J. A. Hoskins, *J. Chem. Soc. Perkin* Trans I, 522 (1972).

Reaction 5(b)

This reaction is also run by analogy with the teachings of ibid. The method comprises reacting pyridyl esters, XI, with excess hydrazine monohydrate in methanol at reflux for several hours. Under certain conditions sulfonamides, XI, may ring-close to saccharin-like structures, either during their preparation in Reaction 5(a) or during reflux with hydrazine in Reaction 5(b). In either case, subsequent reaction with hydrazine as described above may provide hydrazides, XII.

Reaction 5(c)

The conversion of hydrazides to 5-mercaptooxadiazoles is well-known in the literature, e.g., R. W. Young and K. H. Wood, *J. Am. Chem. Soc.*, 77, 400 (1955). In a typical procedure, hydrazides, XII, are heated at reflux with equimolar amounts of potassium hydroxide and an excess of carbon disulfide in methanol or ethanol solvent until the evolution of hydrogen sulfide has nearly stopped. Oxadiazoles, IIIb ($R_5''=H$), are isolated by concentration of the solvent, addition of water to the residue, filtration of the aqueous suspension to remove insoluble impurities, acidification of the aqueous filtrate with hydrochloric acid and filtration.

Alkylation of 5-mercaptooxadiazoles is also well-known in the literature, e.g., S. Giri et al., *Agr. Biol. Chem.*, 40, 17 (1976). Typically, oxadiazoles, IIIb ($R_5''=H$), are reacted with an equimolar amount of base such as potassium hydroxide and excess alkylating agent, $R_5''M$, at reflux in an inert solvent such as methanol or ethanol for 0.5 to 24 hours. Sulfonamides, IIIb, are isolated by concentration of the solvent, addition of water to the residue and filtration. For the case where $R_5''=CF_2H$, the reaction is preferably run in DMF solvent at 60°-90° C. with excess potassium carbonate as base. Following addition of water, sulfonamides, IIIb, are isolated by filtration.

2- and 3-Pyridinesulfonamides of Formula III, substituted in the 3- and 2-positions respectfully with a phenyl group, may be prepared from corresponding 3-phenyl-2-pyridinols and 2-phenyl-3-pyridinols, XIII, by the sequence of reactions shown below in Equation 6.

Equation 6

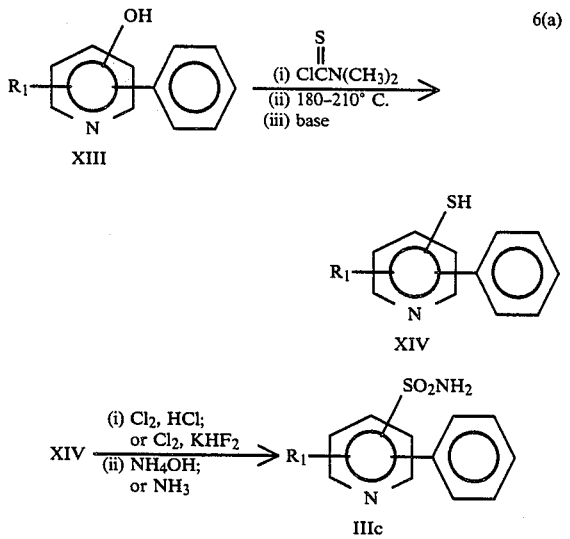

wherein
$R_1$ is as previously defined.

Reaction 6(a)

In these reactions mercaptopyridines, XIV, are prepared by analogy with the teaching of B. Blank et al., *J. Med. Chem.*, 17, 1065 (1974). The method comprises (i) reacting pyridinols, XIII, with dimethylthiocarbamoyl chloride and a base such as 1,4-diazabicyclo[2.2.2]octane (DABCO) in DMF to form the corresponding N,N-dimethyl-O-thiocarbamates; (ii) heating these compounds at elevated temperatures, e.g., 180°-210° C. to form the corresponding N,N-dimethyl-S-carbamates; and (iii) heating these compounds with a base such as sodium carbonate or sodium hydroxide in an inert solvent such as methanol to form mercaptopyridines, XIV.

Reaction 6(b)

These reactions are run by procedures analogous to those described above for the preparation of XI (Equation 5a).

2- and 3-Pyridinesulfonamides of Formula III, substituted in the 3- and 2-positions respectively with pyridinyl, pyrimidinyl, pyrazinyl, pyridazinyl or triazinyl groups (Q is Q-27 to Q-36) may be prepared by the sequence of reactions shown in Equation 7 below.

Equation 7

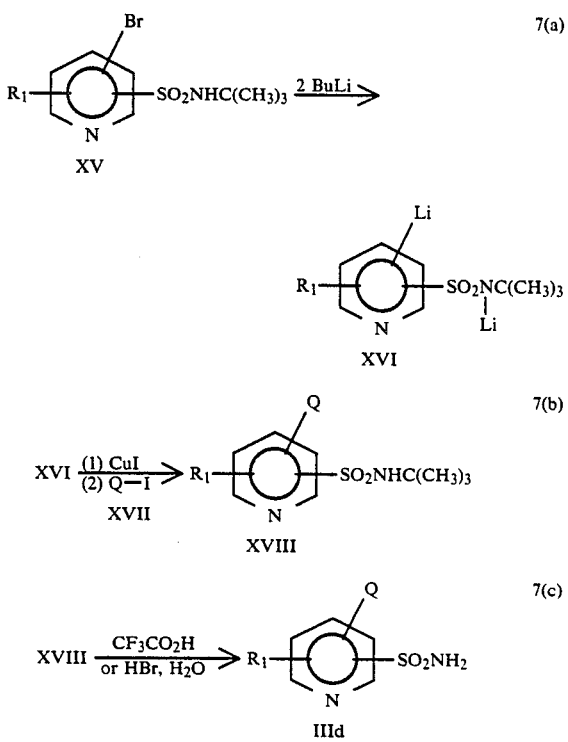

wherein
$R_1$ is H or $CH_3$; and
Q is Q-27 to Q-36.

The compounds of Formula III(d) are prepared by analogy with the teachings of EP-A No. 85,476 (published Dec. 13, 1983).

Reaction 7(a,b)

An appropriate 2-bromo-3-(N-t-butyl)pyridinesulfonamide or 3-bromo-2-(N-t-butyl)pyridinesulfonamide is dissolved in an ethereal solvent, such as tetrahydrofuran, and two equivalents of n-butyllithium in hexanes are added at about −70° C. After 1-5 hours at about −70° C., the corresponding compound of Formula XVI is formed. This is not isolated, but one equivalent of copper(I) iodide is added at about −70° C., followed by 1-1.5 equivalents of an appropriately substituted heteroaromatic iodide of Formula XVII. The reaction mixture is stirred at 0° to 70° C. for 1-3 days, concentrated and poured onto aqueous ammonia. Compounds of Formula XVIII are isolated by filtration if solids, or by extraction with methylene chloride and concentration if oils. The compounds, XVIII, may be further purified by recrystallization or chromatography procedures. The compounds of Formula XV and XVII may be prepared by methods known to those skilled in the art. Pertinent references for the preparation of iodocompounds, XVII, are described in EP-A No. 85,476.

Reaction 7(c)

This reaction is conducted by stirring a compound of Formula XVIII with 2-10 equivalents of trifluoroacetic acid or aqueous HBr with or without an inert solvent at 30°-70° C. for 1-3 days. The product, IIId, may be isolated as a trifluoroacetate or hydrobromide salt by evaporation of solvent and excess acid and trituration with ether. The free base may be obtained by neutralization of the salt with aqueous base, extraction into an organic solvent, and concentration of the organic extracts.

2- and 3-Pyridinesulfonamides of Formula IIIe can be prepared as shown in Equation 8 by procedures analogous to the preparation of Compounds IIIb described in Equation 5.

Equation 8

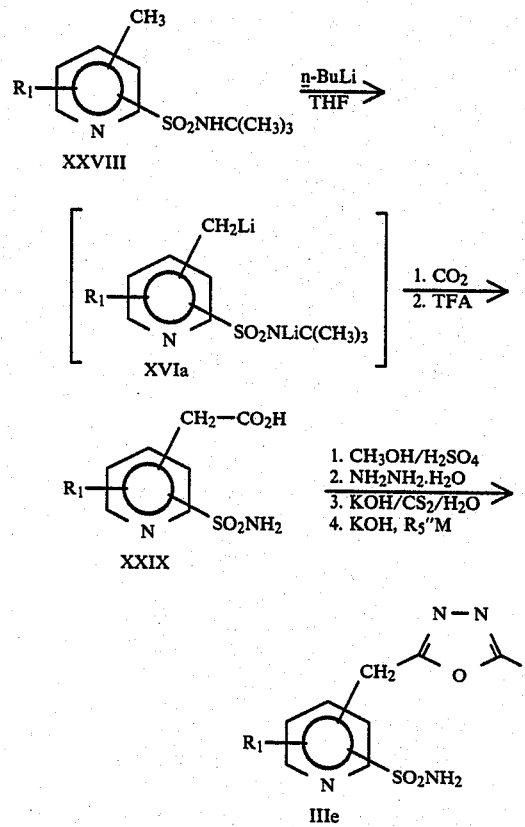

wherein
$R_1$ is as previously defined;
$R_5''$ is $C_1$-$C_3$ alkyl or $CF_2H$; and
M is Cl, Br or I.

Compounds of Formula IIIf in Equation 9a can be prepared from the lithium salt XVIa by procedures described for the preparation of similar compounds in Equation 7 and Compound IIIg can be prepared as shown in Equation 9b.

Equation 9a

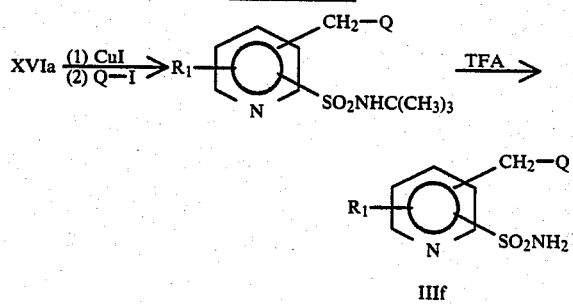

wherein
$R_1$ is H; and
Q is Q-27 to Q-36.

Equation 9b

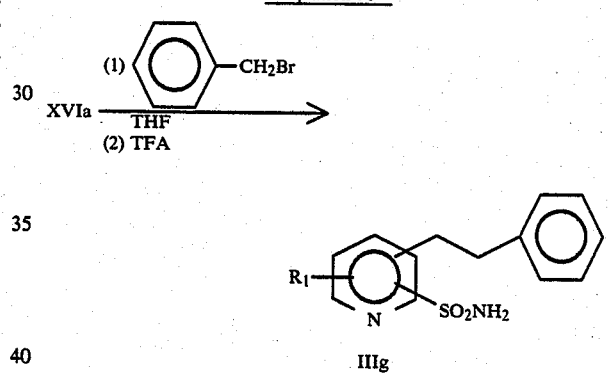

The dilithio salt XVIa can be prepared by lithiation of the appropriate picolinesulfonamides according to the teachings of R. E. Smith, S. Boatman and C. R. Hauser; *J. Org. Chem.*, 33, 2083 (1968).

Nitropyridines of Formula IIIh containing an o-alkylfuran or thiophene group (Q is Q-22 to Q-25), can be prepared by analogy with the teachings in EP-A No. 85,476, and references cited therein as illustrated in Equation 10.

Equation 10

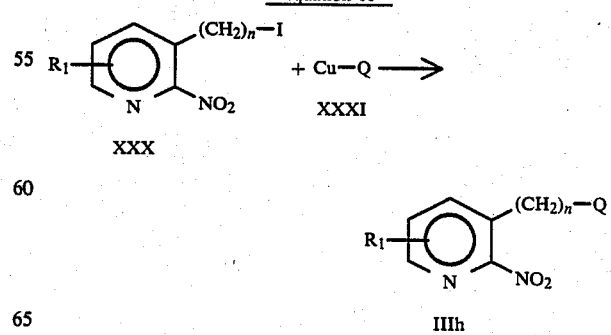

wherein
$R_1$ and n are as originally defined; and

Q is Q-22 to Q-25.

Thus, a furyl- or thienylcopper compound of Formula XXXI is reacted with an o-(iodoalkyl)nitropyridine of Formula XXX in an inert solvent such as pyridine or quinoline at 0° to 60° C. for 1–3 days. The product, IIIh, is isolated by addition of acid such as acetic acid and water, extraction with methylene chloride, stripping of solvent and chromatographing the crude product. The copper compounds of Formula XXXI are prepared by reacting the corresponding lithium compounds with cuprous iodide or cuprous bromide in an inert solvent such as ethyl ether. The detailed procedures for analogous types of reactions are described in the following references: M. Nilsson and C. Ullenius, *Acta. Chem. Scand.*, 24, 2379–2388 (1970); C. Ullenius, *Acta. Chem. Scand.*, 26, 3383–3386 (1972).

2- and 3-Pyridinesulfonamides of Formula III substituted in the 3- and 2-positions, respectively, with a tetrahydrofuran group (Q is Q-26) may be prepared as shown in Equation 11.

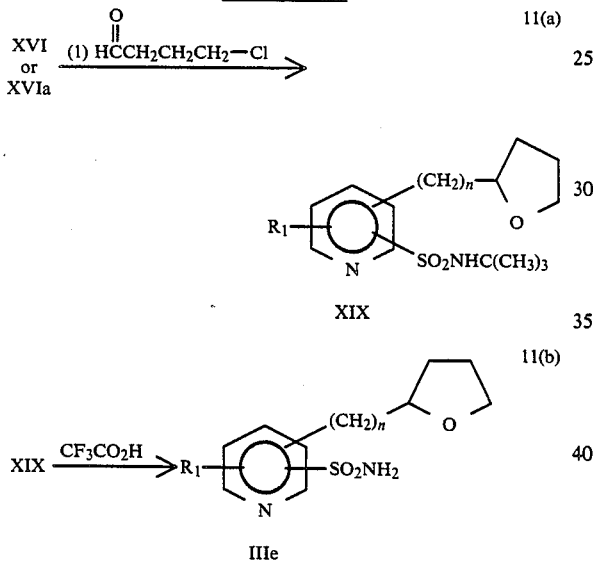

wherein
$R_1$ is H or $CH_3$; and
n is 0 or 1.

The compounds of Formula IIIe are prepared by analogy with the teachings in Ep-A No. 85,476 (published Aug. 10, 1983).

Reaction 11(a)

In this reaction dilithio salt, XVI or XVIa, in tetrahydrofuran is treated with one equivalent of 4-chloro- or 4-bromobutyraldehyde at −70° C. to −80° C. After stirring at about 25° C. for 1–3 days, the reaction is quenched by the addition of an acid such as acetic acid, and the product, XIX, is isolated and purified by stripping the solvent and chromatographing the residue.

Reaction 11(b)

This reaction is run by procedures analogous to those described above in Equation 7(c).

3-Pyridinesulfonamides of Formula IIIi, substituted in the 2-position by a furan or thiophene group (Q is Q-22 to Q-25) may be prepared as shown below in Equation 12.

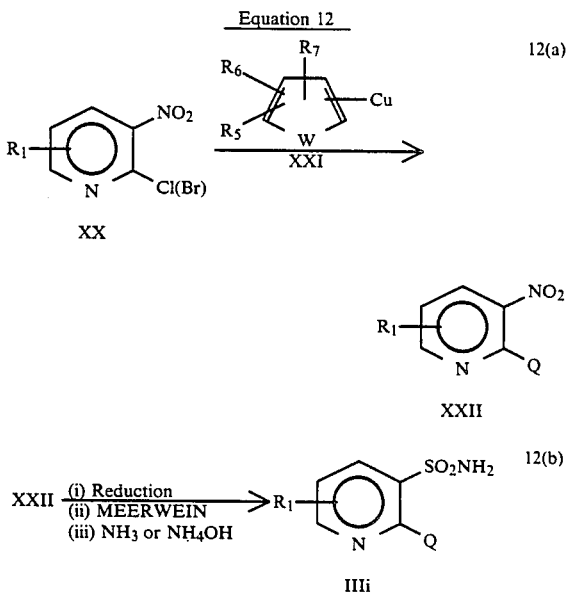

wherein
$R_1$, $R_5$, $R_6$ and $R_7$ are as originally defined;
Q is Q-22 to Q-25; and
W is O or S.

Reactions 12(a,b)

In Reaction 12(a) a furyl- or thienylcopper compound of Formula XXI is reacted with an appropriate chloro- or bromonitropyridine of Formula XX in a solvent such as pyridine or quinoline. The copper compounds of Formula XXI are prepared by reacting the corresponding lithium compounds with cuprous iodide or cuprous bromide in a solvent such as diethyl ether. The detailed procedures for analogous types of reactions are described in the following references: M. Nilsson and C. Ullenius, *Acta. Chem. Scand.*, 24, 2379–2388 (1970); C. Ullenius, *Acta. Chem. Scand.*, 26, 3383–3386 (1972).

2-Pyridinesulfonamides of Formula IIIj, substituted in the 3-position by a furan or thiophene group (Q is Q-22 to Q-25) may be prepared by the sequence of reactions shown in Equation 13 below.

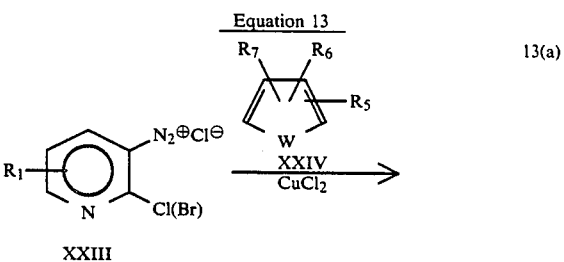

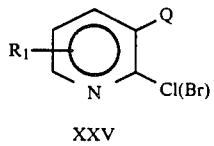

-continued
Equation 13

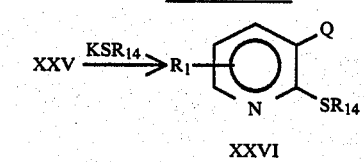

XXVI

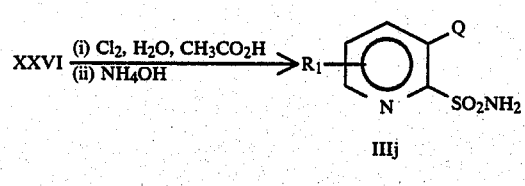

IIIj

Equation 14

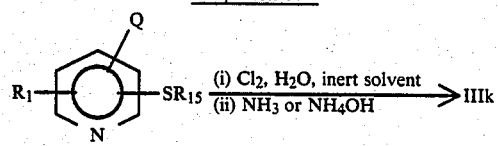

XXVII wherein
$R_1$, $R_5$, $R_6$ and $R_7$ are as originally defined;
$R_{14}$ is $CH_2CH_2CH_3$ or $CH_2C_6H_5$;
Q is Q-22 to Q-25; and
W is O or S.

Reaction 13(a)

In this reaction a 2-halo-3-pyridyl diazonium salt is coupled with an appropriately substituted thiophene or furan in the presence of a catalyst such as cupric chloride. This reaction may be run by procedures analogous to those described in Gomberg and Bachman, *J. Am. Chem. Soc.*, 46, 2339 (1924); J. Johnson, *J. Chem. Soc.*, 895 (1946); and in *J. Pharm. Soc. (Japan)*, 90, 1150–1155 (1970), or simple modifications thereof, by those skilled in the art. In cases where both the α- and the β-position of the thiophene or furan are available for coupling, both isomers are usually obtained with the α-coupled product being the predominant isomer. These isomers may be separated by fractional crystallization or chromatography procedures.

Reaction 13(b)

In this reaction thiopyridines of Formula XXVI are prepared by conventional methods by treating 2-halopyridines, XXV, with potassium benzyl or propylmercaptan in an inert solvent such as DMF at about 25° to 130° C. for one to 24 hours. Following isolation by usual methods, the product, XXVI, may be purified by chromatography procedures.

Reaction 13(c)

And in this reaction the products of Reaction 13(b) are oxidatively chlorinated in a suitable inert solvent such as chloroform, methylene chloride or acetic acid, in the presence of water, to produce the corresponding sulfonyl chlorides. The reaction is carried out in the presence of at least 2.5 molar equivalents of water and at least three molar equivalents of chlorine at about −30° to 5° C. for 1–5 hours. Following isolation of the sulfonyl chlorides, the sulfonyl chlorides are reacted with ammonia or ammonium hydroxide by conventional methods.

Other 2- and 3-pyridinesulfonamides of Formula III may also be prepared by oxidatively chlorinating appropriate 3-heterocyclic-2-thiopyridines and 2-heterocyclic-3-thiopyridines of Formula XXVII to corresponding sulfonyl chlorides, followed by amination to corresponding sulfonamides, as shown below in Equation 14.

wherein
$R_1$ is as originally defined; and
$R_{15}$ is H, $C_2H_5$ or $CH_2C_6H_5$.

The reactions of Equation 14 are carried out by methods analogous to those described above in Equation 13(c) and for the preparation of XI (Equation 5a). The compounds of Formula XXVII may be prepared by those skilled in the art by the application of appropriate methods selected from the variety of known literature procedures for preparing substituted aromatic heterocycles. See, for example, EP-A No. 83,975 (published July 20, 1983), and references cited therein, which describe methods for transforming various o-(substituted)-nitrobenzenes to corresponding o-(heterocyclic)nitrobenzenes, in which the o-heterocyclic groups are Q-1 to Q-21. By carrying out similar reactions on appropriately substituted pyridines, or simple modifications thereof, those skilled in the art may prepare many of the compounds of Formula XXVII above.

There exist a variety of known methods for incorporating a mercapto or alkylthio group into the 2- or 3-position of a pyridine ring, methods which are useful for the preparation of the compounds of the general Formula XXVII described above in Equation 14. The choice of methods used depends in part on the reaction sequences used to prepare compounds XXVII, which would be obvious to those skilled in the art. These methods include (i) reacting 3-pyridyl diazonium salts with potassium ethyl xanthate to form corresponding 3-mercaptopyridines, which can be alkylated to 3-benzyl- or 3-propylthiopyridines by obvious methods; for details, refer to analogous reactions described in *J. Pharm. Belq.*, 22, 213 (1967); ibid., 29, 281 (1974) and *J. Org. Chem.*, 23, 1924 (1958); (ii) saponifying N,N-dimethyl-S-carbamates, prepared from 2- or 3-pyridinols, to form corresponding 2- or 3-mercaptopyridines; for general details see Equation 6(a) above; (iii) reacting 3-halopyridines, containing an activating ortho-group such as aldehyde, ketone, carboxylic ester, amide, nitrile or nitro group, with potassium propanethiol or benzylthiol in an inert solvent such as DMF or hexamethylphosphoramide by known methods to form corresponding 3-benzylthiol- or 3-propanethiolpyridines; (iv) displacing a 2-halogen on a pyridine ring by sulfur nucleophiles such as potassium or sodium hydrosulfide, thiourea or potassium benzylthiol or propanethiol to form 2-thiosubstituted pyridines; for details, see analogous reactions described in *J. Het. Chem.*, 3, 27. (1966); ibid., 17, 149 (1980); ibid. 5, 647 (1958); *J. Am. Chem. Soc.*, 68, 342 (1946) and ibid., 70, 3908 (1948); and (v) diazotizing and converting 2-aminopyridines to 2-pyridinols which may be converted to 2-pyridinethiols with $P_4S_4$; for details see analogous reactions described in *Farmaco Ed. Sci.*, 22, 1069 (1967).

The preparation of pyridinethiols is also reviewed in "Pyridine and Its Derivatives", Part 4, 1964, by H. L. Hale, a part of the series "*The Chemistry of Heterocyclic*

*Compounds"*, A. Weissberger, Ed., published by Interscience Publ., New York and London.

The heterocyclic amines of Formula VII in Equation 3 are also important intermediates for the preparation of the compounds of this invention, and can be prepared by methods known in the literature, or simple modifications thereof, by those skilled in the art. For details, see, for example, EP-A No. 84,224 (published July 27, 1983) and W. Braker et al., *J. Am. Chem. Soc.,* 69, 3072 (1947), which describe the synthesis of pyrimidine- and triazineamines substituted by acetals and thioacetals such as dialkoxymethyl or 1,3-dioxolan-2-yl. See also, for example, South African patent application Nos. 825,045 and 825,671 which describe the synthesis of aminopyrimidines and triazines substituted by such groups as haloalkoxy or haloalkylthio groups, e.g., $OCH_2CH_2F$, $OCH_2CF_3$, $OCF_2H$ or $SCF_2H$. Also, South African Patent Application No. 837,434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

Also, the 5,6-dihydrofuro[2,3-d]pyrimidin-2-amines, the cyclopenta[d]pyrimidin-2-amines (VII, A=A-2) and the 6,7-dihydro-5H-pyrano[2,3-d]pyrimidin-2-amines (VII, A=A-3) can be prepared as described in EP-A No. 15,683. Also, the furo[2,3-d]pyrimidin-2-amines (VII, A=A-4) are described in EP-A No. 46,677.

Compounds of Formula VII, where A is A-5, are described in EP-A No. 73,562. Compounds of Formula VII, where A is A-6, are described in EP-A No. 94,260.

In addition, general methods for preparing aminopyrimidines and triazines have been reviewed in the following publications:

"The Chemistry of Heterocyclic Compounds", a series published by Interscience Publishers, Inc., New York and London;

"Pyrimidines", Vol. 16 of the same series, by D. J. Brown.

"s-Triazines and Derivatives", Vol. 13 of the same series, by E. M. Smolin and L. Rappaport; and F. C. Schaefer, U.S. Pat. No. 3,154,547 and K. R. Huffman and F. C. Schaefer, *J. Org. Chem.,* 28, 1812 (1963) which describe the synthesis of triazines.

Agriculturally suitable salts of compounds of Formulae I and II are also useful herbicides and can be prepared in a number of ways known to the art. For example, metal salts can be made by contacting compounds of Formulae I or II with a solution of an alkali or alkaline earth metal salt having a sufficiently basic anion (e.g., hydroxide, alkoxide, carbonate or hydroxide). Quaternary amine salts can be made by similar techniques.

Salts of compounds of Formulae I and II can also be prepared by exchange of one cation for another. Cationic exchange can be effected by direct contact of an aqueous solution of a salt of a compound of Formulae I or II (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formulae I or II (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formulae I or II with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

3-Nitro-2-(1H-1,2,4-triazol-1-yl)pyridine

A solution of 10 g of 2-chloro-3-nitropyridine dissolved in 30 ml of dry DMF was added dropwise to a suspension containing 6.9 g of 1,2,4-triazole sodium salt (90%, Aldrich Chemical Co.) in 40 ml of dry DMF. After a slow exotherm had subsided, the suspension was heated at 60° for three hours, then cooled to 25° C. and poured onto 500 ml of ice-water to yield a precipitate. After the mixture was filtered, the isolated solid was washed 2×50 ml of water and suction-dried to yield 12 g of crude product. The product was recrystallized from 2-propanol to yield 8 g of the subject compound; m.p. 131°–133°.

Anal. calc. for $C_7H_5N_5O_2$: C, 43.9; H, 2.7; N, 36.6; Found: C, 44.6; H, 2.7; N, 36.7.

EXAMPLE 2

3-Amino-2-(1H-1,2,4-triazol-1-yl)pyridine

To a suspensionn containing 35.4 g of stannous chloride dihydrate in 100 ml of concentrated hydrochloric acid was added portionwise 10 g of the compound prepared in Example 1 over a 0.25 hour period. After the resulting exotherm (23°–79°) slowed, the suspension was heated at 85°–90° for one hour, then cooled to 0°. The mixture was poured onto excess ice-water (about 700 ml), and the suspension was made strongly basic to litmus by addition of 50% aqueous NaOH to yield a precipitate. After filtering the mixture, the isolated solid was washed with water, suction-dried, then recrystallized from ethyl acetate-hexanes to yield 3 g of the subject compound; m.p. 103°–105°.

Anal. calc. for $C_7H_7N_5$: C, 52.2; H, 4.4; N, 43.4; Found: C, 52.4; H, 4.3; N, 41.6.

EXAMPLE 3

2-(1H-1,2,4-Triazol-1-yl)-3-pyridinesulfonyl chloride

A diazonium salt was prepared by adding a solution of 9 g of sodium nitrite in 30 ml of water to a suspension of 20 g of the compound prepared by the procedure of Example 2 in 45 ml of concentrated hydrochloric acid and 127 ml of glacial acetic acid at 0°–25°. After stirring about 0.4 hour, the diazonium suspension was poured slowly into a mixture consisting of 93 ml of acetic acid, 5.3 g of cupric chloride dihydrate and 37 ml of sulfur dioxide while cooling the reaction flask at 10°–20° in a dry ice-acetone bath. During the addition a delayed vigorous gas evolution with foaming occurred and was controlled by cooling and decreasing the rate of addition of the diazonium suspension. After addition was complete, the cooling was removed and the suspension was stirred at ambient temperature for four hours. The suspension was poured into ice-water (about 800 ml)

and stirred to yield a solid. After the mixture was filtered, the isolated solid was washed 2×50 ml of water and suction-dried overnight to yield 17 g of the subject compound; m.p. 128°–132°.

Anal. calc. for $C_7H_5ClN_4O_2S$: C, 34.4; H, 2.1; N, 22.9; Found: C, 34.4; H, 2.1; N, 23.2.

EXAMPLE 4

2-(1H-1,2,4-Triazol-1-yl)-3-pyridinesulfonamide

To a suspension containing 15 g of the compound prepared in Example 3 in 125 ml of tetrahydrofuran was added dropwise 23 ml of concentrated aqueous ammonium hydroxide while maintaining the reaction temperature at 10°–20° with external ice-water cooling. After stirring at room temperature for three hours, the suspension was concentrated in vacuo to a water suspension. The suspension was poured into ice-water (about 200 ml) and stirred to yield a solid. The mixture was filtered to yield 12 g of crude product, which was recrystallized from acetonitrile to yield 8 g of the subject compound; m.p. 185°–188°.

Anal. calc. for $C_7H_7N_5O_2S$: C, 37.3; H, 3.2; N, 31.0; Found: C, 37.4, H, 3.0; N, 30.9.

EXAMPLE 5

N-[(4,6-Dimethoxypyrimidin-2-yl)aminocarbonyl]-2-(1H-1,2,4-triazol-1-yl)-3-pyridinesulfonamide To a suspension containing 0.5 g of the sulfonamide prepared in Example 4 in 10 ml of p-dioxane was added 0.6 g of phenyl(4,6-dimethoxypyrimidin-2-yl)carbamate followed by 0.33 g of 1,8-diazabicyclo[5.4.0]undec-7-ene (DBU). The suspension was stirred at room temperature for about two hours then diluted with about 75 ml of water to form a solution. After acidifying the solution with conc. hydrochloric acid (red to litmus) and stirring 0.5 hour, a precipitate formed. The mixture was filtered and the isolated solid was washed with 10 ml water and suction-dried for 24 hours to yield 0.7 g of the subject compound; m.p. 226°–230°.

Anal. calc. for $C_{14}H_{14}N_8O_5S$: C, 41.4; H, 3.5; N, 27.6; Found: C, 41.3; H, 3.7; N, 27.4.

IR (nujol): 1715 cm-1 (C=O).

Using the techniques described in Equations 1–14 and Examples 1–5, or simple modifications thereof, the following compounds in Tables Ia–IIg can be made by those skilled in the art.

TABLE Ia

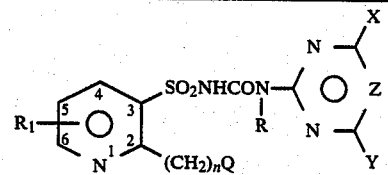

| Q | n | R | R₁ | X | Y | Z | m.p. °C. |
|---|---|---|----|---|---|---|----------|
| Q-1 (R₅, R₆ = H) | 0 | CH₃ | H | OCH₃ | OCH₃ | CH | |
| Q-1 (R₅, R₆ = H) | 0 | H | H | CH₃ | CH₃ | CH | |
| Q-1 (R₅, R₆ = H) | 0 | H | H | CH₃ | OCH₃ | CH | |
| Q-1 (R₅, R₆ = H) | 0 | H | H | OCH₃ | OCH₃ | CH | |
| Q-1 (R₅, R₆ = H) | 0 | H | H | Cl | OCH₃ | CH | |
| Q-1 (R₅ = H, R₆ = CH₃) | 0 | H | H | OCH₃ | OCH₃ | CH | |
| Q-1 (R₅ = CH₃, R₆ = H) | 0 | H | H | OCH₃ | OCH₃ | CH | |
| Q-2 (R₅, R₆ = H) | 0 | H | H | CH₃ | CH₃ | CH | |
| Q-2 (R₅, R₆ = H) | 0 | H | H | OCH₃ | OCH₃ | CH | |
| Q-2 (R₅, R₆ = H) | 0 | H | H | CH₃ | OCH₃ | CH | |
| Q-2 (R₅, R₆ = H) | 0 | H | H | Cl | OCH₃ | CH | |
| Q-2 (R₅ = CH₃, R₆ = H) | 0 | H | H | OCH₃ | OCH₃ | CH | |
| Q-2 (R₅ = H, R₆ = CH₃) | 0 | H | H | OCH₃ | OCH₃ | CH | |
| Q-3 (R₅, R₆ = H) | 0 | H | H | CH₃ | CH₃ | CH | |
| Q-3 (R₅, R₆ = H) | 0 | H | H | CH₃ | OCH₃ | CH | |
| Q-3 (R₅, R₆ = H) | 0 | H | H | OCH₃ | OCH₃ | CH | |
| Q-3 (R₅, R₆ = H) | 0 | H | H | Cl | OCH₃ | CH | |
| Q-3 (R₅ = CH₃; R₆ = H) | 0 | H | H | OCH₃ | OCH₃ | CH | |
| Q-4 (R₅, R₆ = H) | 0 | H | H | CH₃ | CH₃ | CH | |
| Q-4 (R₅, R₆ = H) | 0 | H | H | OCH₃ | CH₃ | CH | |
| Q-4 (R₅, R₆ = H) | 0 | H | H | OCH₃ | OCH₃ | CH | |
| Q-4 (R₅, R₆ = H) | 0 | H | H | Cl | OCH₃ | CH | |
| Q-5 (R₅, R₆ = H) | 0 | H | H | OCH₃ | OCH₃ | CH | |
| Q-5 (R₅, R₆ = H) | 0 | H | H | CH₃ | CH₃ | CH | |
| Q-5 (R₅, R₆ = H) | 0 | H | H | CH₃ | OCH₃ | CH | |
| Q-5 (R₅, R₆ = H) | 0 | H | H | Cl | OCH₃ | CH | |
| 4-chlorophenyl | 0 | H | H | OCH₃ | OCH₃ | CH | |
| 3-methoxyphenyl | 0 | H | H | OCH₃ | OCH₃ | CH | |
| 3-methylphenyl | 0 | H | H | OCH₃ | OCH₃ | CH | |
| Q-6 (R₅ = H) | 0 | H | H | OCH₃ | OCH₃ | CH | |
| Q-6 (R₅ = H) | 0 | H | H | CH₃ | OCH₃ | CH | |
| Q-6 (R₅ = H) | 0 | H | H | CH₃ | CH₃ | CH | |
| Q-6 (R₅ = H) | 0 | H | H | Cl | OCH₃ | CH | |
| Q-7 (R₅, R₆, R₇ = H) | 0 | H | H | CH₃ | CH₃ | CH | |
| Q-7 (R₅, R₆, R₇ = H) | 0 | H | H | OCH₃ | OCH₃ | CH | |
| Q-7 (R₅, R₆, R₇ = H) | 0 | H | H | CH₃ | OCH₃ | CH | |
| Q-7 (R₅, R₆, R₇ = H) | 0 | H | H | Cl | OCH₃ | CH | |
| Q-7 (R₅, R₇ = CH₃; R₆ = H) | 0 | H | H | OCH₃ | OCH₃ | CH | 204–207 |
| Q-8 (R₅' = H) | 0 | H | H | CH₃ | CH₃ | CH | |
| Q-8 (R₅' = H) | 0 | H | H | OCH₃ | OCH₃ | CH | |
| Q-8 (R₅' = H) | 0 | H | H | CH₃ | OCH₃ | CH | |
| Q-8 (R₅' = H) | 0 | H | H | Cl | OCH₃ | CH | |

TABLE Ia-continued

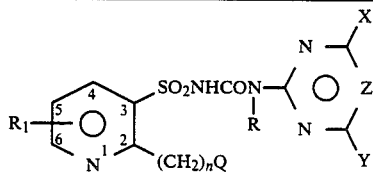

| Q | n | R | R₁ | X | Y | Z | m.p. °C. |
|---|---|---|---|---|---|---|---|
| Q-8 (R₅' = CH₃) | 0 | H | H | OCH₃ | OCH₃ | CH | |
| Q-8 (R₅' = CH₃) | 0 | H | H | CH₃ | OCH₃ | CH | |
| Q-8 (R₅' = CH₃) | 0 | H | H | CH₃ | CH₃ | CH | |
| Q-8 (R₅' = CH₃) | 0 | H | H | Cl | OCH₃ | CH | |
| Q-8 (R₅' = CH₃) | 0 | CH₃ | H | OCH₃ | OCH₃ | CH | |
| Q-8 (R₅' = C₂H₅) | 0 | H | H | CH₃ | CH₃ | CH | |
| Q-8 (R₅' = C₂H₅) | 0 | H | H | OCH₃ | OCH₃ | CH | |
| Q-8 (R₅' = C₂H₅) | 0 | H | H | CH₃ | OCH₃ | CH | |
| Q-8 (R₅' = C₂H₅) | 0 | H | H | Cl | OCH₃ | CH | |
| Q-8 (R₅' = SCH₃) | 0 | H | H | OCH₃ | OCH₃ | CH | |
| Q-8 (R₅' = SCH₃) | 0 | H | H | CH₃ | OCH₃ | CH | |
| Q-8 (R₅' = SCH₃) | 0 | H | H | CH₃ | CH₃ | CH | |
| Q-8 (R₅' = SCH₃) | 0 | H | H | Cl | OCH₃ | CH | |
| Q-8 (R₅' = SC₂H₅) | 0 | H | H | CH₃ | CH₃ | CH | |
| Q-8 (R₅' = SC₂H₅) | 0 | H | H | OCH₃ | OCH₃ | CH | |
| Q-8 (R₅' = SC₂H₅) | 0 | H | H | CH₃ | OCH₃ | CH | |
| Q-8 (R₅' = SC₂H₅) | 0 | H | H | Cl | OCH₃ | CH | |
| Q-8 (R₅' = SCH₂CH=CH₂) | 0 | H | H | OCH₃ | OCH₃ | CH | |
| Q-8 (R₅' = SCH₂CH=CH₂) | 0 | H | H | CH₃ | OCH₃ | CH | |
| Q-8 (R₅' = SCH₂CH=CH₂) | 0 | H | H | CH₃ | CH₃ | CH | |
| Q-8 (R₅' = SCH₂CH=CH₂) | 0 | H | H | Cl | OCH₃ | CH | |
| Q-8 (R₅' = SCF₂H) | 0 | H | H | OCH₃ | OCH₃ | CH | |
| Q-8 (R₅' = SCF₂H) | 0 | H | H | CH₃ | CH₃ | CH | |
| Q-8 (R₅' = SCF₂H) | 0 | H | H | OCH₃ | CH₃ | CH | |
| Q-8 (R₅' = SCF₂H) | 0 | H | H | Cl | OCH₃ | CH | |
| Q-8 (R₅' = SC₃H₇) | 0 | H | H | OCH₃ | OCH₃ | CH | |
| Q-8 (R₅' = SC₃H₇) | 0 | H | H | CH₃ | OCH₃ | CH | |
| Q-8 (R₅' = SC₃H₇) | 0 | H | H | Cl | OCH₃ | CH | |
| Q-8 (R₅' = OCH₃) | 0 | H | H | OCH₃ | OCH₃ | CH | |
| Q-8 (R₅' = OC₂H₅) | 0 | H | H | OCH₃ | OCH₃ | CH | |
| Q-9 (R₅ = H) | 0 | H | H | OCH₃ | OCH₃ | CH | |
| Q-9 (R₅ = H) | 0 | H | H | CH₃ | OCH₃ | CH | |
| Q-9 (R₅ = H) | 0 | H | H | CH₃ | CH₃ | CH | |
| Q-9 (R₅ = H) | 0 | H | H | Cl | OCH₃ | CH | |
| Q-9 (R₅ = CH₃) | 0 | H | H | OCH₃ | OCH₃ | CH | |
| Q-9 (R₅ = CH₃) | 0 | H | H | CH₃ | OCH₃ | CH | |
| Q-9 (R₅ = CH₃) | 0 | H | H | CH₃ | CH₃ | CH | |
| Q-9 (R₅ = CH₃) | 0 | H | H | Cl | OCH₃ | CH | |
| Q-10 (R₅ = H) | 0 | H | H | CH₃ | CH₃ | CH | |
| Q-10 (R₅ = H) | 0 | H | H | OCH₃ | OCH₃ | CH | |
| Q-10 (R₅ = H) | 0 | H | H | CH₃ | OCH₃ | CH | |
| Q-10 (R₅ = H | 0 | H | H | Cl | OCH₃ | CH | |
| Q-10-(R₅ = CH₃) | 0 | H | H | CH₃ | CH₃ | CH | |
| Q-10-(R₅ = CH₃) | 0 | H | H | OCH₃ | OCH₃ | CH | |
| Q-10-(R₅ = CH₃) | 0 | H | H | CH₃ | OCH₃ | CH | |
| Q-10-(R₅ = CH₃) | 0 | H | H | Cl | OCH₃ | CH | |
| Q-11 (R₅ = H) | 0 | H | H | OCH₃ | OCH₃ | CH | |
| Q-12 (R₈ = H) | 0 | H | H | OCH₃ | OCH₃ | CH | |
| Q-12 (R₈ = Cl) | 0 | H | H | OCH₃ | OCH₃ | CH | |
| Q-13 (R₅ = CH₃) | 0 | H | H | OCH₃ | OCH₃ | CH | |
| Q-14 (R₅ = H) | 0 | H | H | OCH₃ | OCH₃ | CH | |
| Q-14 (R₅ = H) | 0 | H | H | CH₃ | OCH₃ | CH | |
| Q-14 (R₅ = H) | 0 | H | H | Cl | OCH₃ | CH | |
| Q-15 (R₅ = H) | 0 | H | H | OCH₃ | OCH₃ | CH | |
| Q-16 (R₅, R₆ = H) | 0 | H | H | CH₃ | CH₃ | CH | 240–243 |
| Q-16 (R₅, R₆ = H) | 0 | H | H | OCH₃ | OCH₃ | CH | 235–238 |
| Q-16 (R₅, R₆ = H) | 0 | H | H | CH₃ | OCH₃ | CH | 225–228 |
| Q-16 (R₅, R₆ = H) | 0 | H | H | Cl | OCH₃ | CH | |
| Q-17 (R₅ = CH₃, R₆ = CH₃) | 0 | H | H | OCH₃ | OCH₃ | CH | |
| Q-17 (R₅ = CH₃, R₆ = CH₃) | 0 | H | H | CH₃ | OCH₃ | CH | |
| Q-17 (R₅ = H, R₆ = CH₃) | 0 | H | H | CH₃ | CH₃ | CH | |
| Q-17 (R₅ = H, R₆ = CH₃) | 0 | H | H | Cl | OCH₃ | CH | |
| Q-18 (R₅ = H, R₆ = CH₃) | 0 | H | H | OCH₃ | OCH₃ | CH | |
| Q-18 (R₅ = CH₃, R₆ = CH₃) | 0 | H | H | CH₃ | OCH₃ | CH | |
| Q-18 (R₅ = H, R₆ = CH₃) | 0 | H | H | CH₃ | CH₃ | CH | |
| Q-18 (R₅ = H, R₆ = CH₃) | 0 | H | H | Cl | OCH₃ | CH | |
| Q-19 (R₅ = CH₃, R₆ = H) | 0 | H | H | OCH₃ | OCH₃ | CH | |
| Q-20 (R₅, R₆ = CH₃) | 0 | H | H | OCH₃ | OCH₃ | CH | |
| Q-21 (R₅, R₆, R₇ = H) | 0 | H | H | OCH₃ | OCH₃ | CH | |
| Q-22 (R₅, R₆, R₇ = H) | 0 | H | H | OCH₃ | OCH₃ | CH | |
| Q-23 (R₅, R₆, R₇ = H) | 0 | H | H | OCH₃ | OCH₃ | CH | |

TABLE Ia-continued

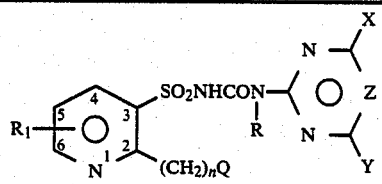

| Q | n | R | R$_1$ | X | Y | Z | m.p. °C. |
|---|---|---|---|---|---|---|---|
| Q-24 (R$_5$, R$_6$, R$_7$ = H) | 0 | H | H | OCH$_3$ | CH$_3$ | CH | |
| Q-25 (R$_5$, R$_6$, R$_7$ = H) | 0 | H | H | OCH$_3$ | OCH$_3$ | CH | |
| Q-26 (W' = O) | 0 | H | H | OCH$_3$ | OCH$_3$ | CH | |
| Q-27 (R$_5$, R$_6$ = H, n' = 0) | 0 | H | H | OCH$_3$ | OCH$_3$ | CH | |
| Q-28 (R$_5$, R$_6$ = H, n' = 0) | 0 | H | H | OCH$_3$ | OCH$_3$ | CH | |
| Q-29 (R$_5$, R$_6$ = H, n' = 0) | 0 | H | H | OCH$_3$ | OCH$_3$ | CH | |
| Q-30 (R$_5$ = H; R$_9$, R$_{10}$ = OCH$_3$) | 0 | H | H | OCH$_3$ | OCH$_3$ | CH | |
| Q-30 (R$_5$ = H; R$_9$, R$_{10}$ = CH$_3$) | 0 | H | H | OCH$_3$ | OCH$_3$ | CH | |
| Q-31 (R$_9$, R$_{10}$ = H) | 0 | H | H | OCH$_3$ | OCH$_3$ | CH | |
| Q-32 (R$_9$, R$_{10}$ = H) | 0 | H | H | OCH$_3$ | OCH$_3$ | CH | |
| Q-33 (R$_5$, R$_6$ = H) | 0 | H | H | OCH$_3$ | OCH$_3$ | CH | |
| Q-34 (R$_5$, R$_6$ = H) | 0 | H | H | OCH$_3$ | OCH$_3$ | CH | |
| Q-35 (R$_{11}$, R$_{12}$ = OCH$_3$) | 0 | H | H | OCH$_3$ | OCH$_3$ | CH | |
| Q-36 (R$_{11}$, R$_{12}$ = CH$_3$) | 0 | H | H | OCH$_3$ | OCH$_3$ | CH | |
| C$_6$H$_5$ | 0 | H | H | CH$_3$ | CH$_3$ | CH | |
| C$_6$H$_5$ | 0 | H | H | OCH$_3$ | CH$_3$ | CH | |
| C$_6$H$_5$ | 0 | H | H | OCH$_3$ | OCH$_3$ | CH | |
| C$_6$H$_5$ | 0 | H | H | Cl | OCH$_3$ | CH | |
| Q-1 (R$_5$, R$_6$ = H) | 0 | H | H | CH$_3$ | OCH$_3$ | N | |
| Q-2 (R$_5$, R$_6$ = H) | 0 | H | H | OCH$_3$ | OCH$_3$ | N | |
| Q-3 (R$_5$ = CH$_3$, R$_6$ = H) | 0 | H | H | OCH$_3$ | OCH$_3$ | N | |
| Q-8 (R$_5'$ = CH$_3$) | 0 | H | H | CH$_3$ | OCH$_3$ | N | |
| Q-8 (R$_5'$ = SCH$_3$) | 0 | H | H | OCH$_3$ | OCH$_3$ | N | |
| Q-9 (R$_5$ = CH$_3$) | 0 | H | H | CH$_3$ | OCH$_3$ | N | |
| Q-10 (R$_5$ = CH$_3$) | 0 | H | H | CH$_3$ | OCH$_3$ | N | |
| Q-12 (R$_8$ = Cl) | 0 | H | H | CH$_3$ | OCH$_3$ | N | |
| Q-17 (R$_5$ = H, R$_6$ = CH$_3$) | 0 | H | H | OCH$_3$ | CH$_3$ | N | |
| Q-18 (R$_5$ = H, R$_6$ = CH$_3$) | 0 | H | H | CH$_3$ | OCH$_3$ | N | |
| Q-18 (R$_5$ = H, R$_6$ = CH$_3$) | 0 | H | H | OCH$_3$ | OCH$_3$ | N | |
| Q-22 (R$_5$, R$_6$, R$_7$ = H) | 0 | H | H | CH$_3$ | OCH$_3$ | N | |
| Q-26 (W' = O) | 0 | H | H | CH$_3$ | OCH$_3$ | N | |
| Q-27 (R$_5$, R$_6$ = H, n' = 0) | 0 | H | H | CH$_3$ | OCH$_3$ | N | |
| Q-27 (R$_5$, R$_6$ = H, n' = 0) | 0 | H | H | OCH$_3$ | OCH$_3$ | N | |
| Q-30 (R$_5$, R$_9$, R$_{10}$ = H) | 0 | H | H | CH$_3$ | OCH$_3$ | N | |
| Q-30 (R$_5$, R$_9$, R$_{10}$ = H) | 0 | H | H | OCH$_3$ | OCH$_3$ | N | |
| Q-33 (R$_5$, R$_6$ = H) | 0 | H | H | CH$_3$ | OCH$_3$ | N | |
| C$_6$H$_5$ | 0 | H | H | CH$_3$ | OCH$_3$ | N | |
| C$_6$H$_5$ | 0 | H | H | OCH$_3$ | OCH$_3$ | N | |
| C$_6$H$_5$ | 0 | H | H | CH$_3$ | CH$_3$ | N | |
| Q-2 (R$_5$, R$_6$ = H) | 0 | H | 5-Cl | OCH$_3$ | OCH$_3$ | CH | |
| Q-16 (R$_5$ = H, R$_6$ = CH$_3$) | 0 | H | 6-Br | OCH$_3$ | OCH$_3$ | CH | |
| Q-8 (R$_5'$ = SCH$_3$) | 0 | H | 5-CH$_3$ | OCH$_3$ | OCH$_3$ | CH | |
| Q-8 (R$_5'$ = SCH$_3$) | 0 | H | 5-Cl | OCH$_3$ | CH$_3$ | N | |
| Q-1 (R$_5$, R$_6$ = H) | 0 | H | 5-CH$_3$ | OCH$_3$ | CH$_3$ | N | |
| Q-1 (R$_5$, R$_6$ = H) | 0 | CH$_3$ | H | OCH$_3$ | CH$_3$ | N | |
| Q-8 (R$_5'$ = SCH$_3$) | 0 | H | H | OC$_2$H$_5$ | CH$_3$ | CH | |
| Q-1 (R$_5$, R$_6$ = H) | 0 | H | H | F | OCH$_3$ | CH | |
| Q-2 (R$_5$, R$_6$ = H) | 0 | H | H | Br | OCH$_3$ | CH | |
| Q-3 (R$_5$, R$_6$ = H) | 0 | H | H | I | OCH$_3$ | CH | |
| Q-8 (R$_5'$ = SCH$_3$) | 0 | H | H | OCF$_2$H | OCH$_3$ | CH | |
| Q-10 (R$_5$ = CH$_3$) | 0 | H | H | CH$_2$F | OCH$_3$ | CH | |
| Q-18 (R$_5$ = H, R$_6$ = CH$_3$) | 0 | H | H | OCH$_2$CH$_2$F | CH$_3$ | CH | |
| Q-17 (R$_5$ = H, R$_6$ = CH$_3$) | 0 | H | H | OCH$_2$CHF$_2$ | CH$_3$ | CH | |
| Q-8 (R$_5'$ = SCH$_3$) | 0 | H | H | OCH$_2$CF$_3$ | OCH$_3$ | CH | |
| Q-10 (R$_5$ = CH$_3$) | 0 | H | H | CF$_3$ | OCH$_3$ | CH | |
| Q-2 (R$_5$, R$_6$ = H) | 0 | H | H | OCH$_2$CH$_3$ | OCH$_3$ | N | |
| Q-1 (R$_5$, R$_6$ = H) | 0 | H | H | OCH$_2$CH$_2$F | CH$_3$ | N | |
| Q-8 (R$_5'$ = SCH$_3$) | 0 | H | H | OCH$_2$CF$_3$ | OCH$_3$ | N | |
| Q-9 (R$_5$ = CH$_3$) | 0 | H | H | OCH$_3$ | H | CH | |
| Q-16 (R$_5$ = H, R$_6$ = CH$_3$) | 0 | H | H | CH$_3$ | OC$_2$H$_5$ | CH | |
| Q-8 (R$_5'$ = SCH$_3$) | 0 | H | H | CH$_3$ | CH$_2$OCH$_3$ | CH | |
| Q-8 (R$_5'$ = CH$_3$) | 0 | H | H | OC$_2$H$_5$ | NHCH$_3$ | N | |
| Q-17 (R$_5$ = H, R$_6$ = CH$_3$) | 0 | H | H | OCH$_3$ | N(OCH$_3$)CH$_3$ | N | |
| Q-8 (R$_5'$ = SCH$_3$) | 0 | H | H | OCH$_3$ | N(CH$_3$)$_2$ | N | |
| Q-18 (R$_5$ = H, R$_6$ = CH$_3$) | 0 | H | H | OCH$_3$ | C$_2$H$_5$ | CH | |
| Q-12 (R$_8$ = Cl) | 0 | H | H | OCH$_3$ | CF$_3$ | CH | |
| Q-11 (R$_5$ = CH$_3$) | 0 | H | H | OCH$_3$ | SCH$_3$ | N | |
| Q-18 (R$_5$ = H, R$_6$ = CH$_3$) | 0 | H | H | CH$_3$ | OCH$_2$CH=CH$_2$ | N | |
| Q-10 (R$_5$ = H) | 0 | H | H | CH$_3$ | OCH$_2$C≡CH | N | |
| Q-13 (R$_5$ = CH$_3$) | 0 | H | H | OCH$_3$ | CH$_2$OCH$_2$CH$_3$ | CH | |
| Q-17 (R$_5$ = H, R$_6$ = CH$_3$) | 0 | H | H | CH$_3$ | OCH$_2$CH$_2$OCH$_3$ | CH | |

TABLE Ia-continued

| Q | n | R | R₁ | X | Y | Z | m.p. °C. |
|---|---|---|---|---|---|---|---|
| Q-14 (R₅ = H) | 0 | H | H | CH₃ | CH₂SCH₃ | CH | |
| Q-1 (R₅, R₆ = H) | 0 | H | H | OCH₃ | i-C₃H₇ | CH | |
| Q-10 (R₅ = CH₃) | 0 | H | H | CH₃ | C(=O)H | CH | |
| Q-1 (R₅, R₆ = H) | 0 | H | H | CH₃ | C(=O)CH₃ | CH | |
| Q-8 (R₅' = SCH₃) | 0 | H | H | OCH₃ | CH(OCH₃)₂ | CH | |
| Q-1 (R₅, R₆ = H) | 0 | H | H | CH₃ | CH(OCH₃)₂ | N | |
| Q-8 (R₅ = SCH₃) | 0 | H | H | OCH₃ | CH(OC₂H₅)₂ | CH | |
| Q-2 (R₅, R₆ = H) | 0 | H | H | OCH₃ | CH(SCH₃)₂ | CH | |
| Q-3 (R₅, R₆ = H) | 0 | H | H | OCH₃ | C(CH₃)(OCH₃)₂ | CH | |
| Q-8 (R₅' = SCH₃) | 0 | H | H | OCH₃ | 1,3-dioxolan-2-yl | CH | |
| Q-18 (R₅ = H, R₆ = CH₃) | 0 | H | H | CH₃ | 1,3-dioxan-2-yl | CH | |
| Q-17 (R₅ = H, R₆ = CH₃) | 0 | H | H | OCH₃ | 1,3-oxathiolan-2-yl | CH | |
| Q-8 (R₅' = CH₃) | 0 | H | H | OCH₃ | 4-methyl-1,3-dioxolan-2-yl | CH | |
| Q-10 (R₅ = H) | 0 | H | H | OCH₃ | OCF₂H | CH | |
| Q-14 | 0 | H | H | OCH₃ | SCF₂H | CH | |
| Q-8 (R₅' = SCH₃) | 0 | H | H | OCH₃ | cyclopropyl | N | |
| Q-1 (R₅, R₆ = H) | 0 | H | H | OCH₃ | cyclopropyl | CH | |
| C₆H₅ | 0 | H | H | OCH₃ | cyclopropyl | N | |
| C₆H₅ | 0 | H | H | OCH₃ | cyclopropyl | CH | |
| Q-1 (R₅, R₆ = H) | 1 | CH₃ | H | OCH₃ | OCH₃ | CH | |
| Q-1 (R₅, R₆ = H) | 1 | H | H | CH₃ | CH₃ | CH | |
| Q-1 (R₅, R₆ = H) | 1 | H | H | CH₃ | OCH₃ | CH | |

TABLE Ia-continued

| Q | n | R | R₁ | X | Y | Z | m.p. °C. |
|---|---|---|----|---|---|---|---------|
| Q-1 (R₅, R₆ = H) | 1 | H | H | OCH₃ | OCH₃ | CH | |
| Q-1 (R₅, R₆ = H) | 1 | H | H | Cl | OCH₃ | CH | |
| Q-1 (R₅ = H, R₆ = CH₃) | 1 | H | H | OCH₃ | OCH₃ | CH | |
| Q-1 (R₅ = H, CH₃, R₆ = H) | 1 | H | H | OCH₃ | OCH₃ | CH | |
| Q-2 (R₅, R₆ = H) | 1 | H | H | CH | CH | CH | |
| Q-2 (R₅, R₆ = H) | 1 | H | H | OCH₃ | OCH₃ | CH | |
| Q-2 (R₅, R₆ = H) | 1 | H | H | CH₃ | OCH₃ | CH | |
| Q-2 (R₅, R₆ = H) | 1 | H | H | Cl | OCH₃ | CH | |
| Q-2 (R₅ = CH₃, R₆ = H) | 1 | H | H | OCH₃ | OCH₃ | CH | |
| Q-2 (R₅ = H, R₆ = CH₃) | 1 | H | H | OCH₃ | OCH₃ | CH | |
| Q-3 (R₅, R₆ = H) | 1 | H | H | CH₃ | CH₃ | CH | |
| Q-3 (R₅, R₆ = H) | 1 | H | H | CH₃ | OCH₃ | CH | |
| Q-3 (R₅, R₆ = H) | 1 | H | H | OCH₃ | OCH₃ | CH | |
| Q-3 (R₅, R₆ = H) | 1 | H | H | Cl | OCH₃ | CH | |
| Q-3 (R₅ = CH₃; R₆ = H) | 1 | H | H | OCH₃ | OCH₃ | CH | |
| Q-4 (R₅, R₆ = H) | 1 | H | H | CH₃ | CH₃ | CH | |
| Q-4 (R₅, R₆ = H) | 1 | H | H | OCH₃ | CH₃ | CH | |
| Q-4 (R₅, R₆ = H) | 1 | H | H | OCH₃ | OCH₃ | CH | |
| Q-4 (R₅, R₆ = H) | 1 | H | H | Cl | OCH₃ | CH | |
| Q-5 (R₅, R₆ = H) | 1 | H | H | OCH₃ | OCH₃ | CH | |
| Q-5 (R₅, R₆ = H) | 1 | H | H | CH₃ | CH₃ | CH | |
| Q-5 (R₅, R₆ = H) | 1 | H | H | CH₃ | OCH₃ | CH | |
| Q-5 (R₅, R₆ = H) | 1 | H | H | Cl | OCH₃ | CH | |
| Q-6 (R₅ = H) | 1 | H | H | OCH₃ | OCH₃ | CH | |
| Q-6 (R₅ = H) | 1 | H | H | CH₃ | OCH₃ | CH | |
| Q-6 (R₅ = H) | 1 | H | H | CH₃ | CH₃ | CH | |
| Q-6 (R₅ = H) | 1 | H | H | Cl | OCH₃ | CH | |
| Q-8 (R₅' = H) | 1 | H | H | CH₃ | CH₃ | CH | |
| Q-8 (R₅' = H) | 1 | H | H | OCH₃ | OCH₃ | CH | |
| Q-8 (R₅' = H) | 1 | H | H | CH₃ | OCH₃ | CH | |
| Q-8 (R₅' = H) | 1 | H | H | Cl | OCH₃ | CH | |
| Q-9 (R₅ = H) | 1 | H | H | OCH₃ | OCH₃ | CH | |
| Q-9 (R₅ = H) | 1 | H | H | CH₃ | CH₃ | CH | |
| Q-10 (R₅ = H) | 1 | H | H | OCH₃ | OCH₃ | CH | |
| Q-10 (R₅ = H) | 1 | H | H | CH₃ | CH₃ | CH | |
| Q-10 (R₅ = H) | 1 | H | H | Cl | OCH₃ | CH | |
| Q-11 (R₅ = H) | 1 | H | H | OCH₃ | OCH₃ | CH | |
| Q-11 (R₅ = H) | 1 | H | H | CH₃ | OCH₃ | CH | |
| Q-12 (R₈ = H) | 1 | H | H | CH₃ | CH₃ | CH | |
| Q-12 (R₈ = H) | 1 | H | H | Cl | OCH₃ | CH | |
| Q-13 (R₅ = CH₃) | 1 | H | H | OCH₃ | OCH₃ | CH | |
| Q-14 (R₅ = H) | 1 | H | H | CH₃ | CH₃ | CH | |
| Q-14 (R₅ = H) | 1 | H | H | OCH₃ | OCH₃ | CH | |
| Q-14 (R₅ = H) | 1 | H | H | CH₃ | OCH₃ | CH | |
| Q-14 (R₅ = H) | 1 | H | H | Cl | OCH₃ | CH | |
| Q-15 (R₅ = H) | 1 | H | H | OCH₃ | OCH₃ | CH | |
| Q-16 (R₅ = H, R₆ = H) | 1 | H | H | CH₃ | OCH₃ | CH | |
| Q-16 (R₅ = H, R₆ = H) | 1 | H | H | CH₃ | CH₃ | CH | |
| Q-16 (R₅ = H, R₆ = H) | 1 | H | H | Cl | OCH₃ | CH | |
| Q-17 (R₅ = H, R₆ = H) | 1 | H | H | CH₃ | CH₃ | CH | |
| Q-17 (R₅ = H, R₆ = H) | 1 | H | H | OCH₃ | OCH₃ | CH | |
| Q-18 (R₅ = H, R₆ = H) | 1 | H | H | CH₃ | OCH₃ | CH | |
| Q-18 (R₅ = H, R₆ = H) | 1 | H | H | Cl | OCH₃ | CH | |
| Q-18 (R₅ = H, R₆ = H) | 1 | H | H | OCH₃ | OCH₃ | CH | |
| Q-19 (R₅ = CH₃, R₆ = H) | 1 | H | H | OCH₃ | OCH₃ | CH | |
| Q-20 (R₅, R₆ = CH₃) | 1 | H | H | OCH | OCH | CH | |
| Q-22 (R₅, R₆, R₇ = H) | 1 | H | H | OCH₃ | OCH₃ | CH | |
| Q-24 (R₅, R₆, R₇ = H) | 1 | H | H | OCH₃ | CH₃ | CH | |
| Q-28 (R₅, R₆ = H, n' = 0) | 1 | H | H | OCH₃ | OCH₃ | CH | |
| Q-30 (R₅ = H, R₉, R₁₀ = CH₃) | 1 | H | H | OCH₃ | OCH₃ | CH | |
| Q-33 (R₅, R₆ = H) | 1 | H | H | OCH₃ | OCH₃ | CH | |
| Q-35 (R₁₁, R₁₂ = OCH₃) | 1 | H | H | OCH₃ | OCH₃ | CH | |
| C₆H₅ | 1 | H | H | OCH₃ | OCH₃ | CH | |
| C₆H₅ | 1 | H | H | OCH₃ | CH₃ | CH | |
| Q-37 (R₅ = H) | 1 | H | H | OCH₃ | OCH₃ | CH | |
| Q-38 (R₅ = H) | 1 | H | H | OCH₃ | OCH₃ | CH | |
| Q-39 (R₅, R₆ = H) | 1 | H | H | OCH₃ | OCH₃ | CH | |
| Q-1 (R₅, R₆ = H) | 1 | H | H | OCH₃ | OCH₃ | N | |
| Q-2 (R₅, R₆ = H) | 1 | H | H | CH₃ | OCH₃ | N | |
| Q-8 (R₅' = CH₃) | 1 | H | H | CH₃ | OCH₃ | N | |
| Q-8 (R₅' = CH₃) | 1 | H | H | OCH₃ | OCH₃ | N | |

TABLE Ia-continued

[Structure: R₁-pyridine ring with SO₂NHCON(R)- linkage to pyrimidine/triazine ring bearing X, Y, Z substituents; (CH₂)ₙQ at position 2]

| Q | n | R | $R_1$ | X | Y | Z | m.p. °C. |
|---|---|---|-------|---|---|---|----------|
| Q-12 ($R_8$ = Cl) | 1 | H | H | $OCH_3$ | $OCH_3$ | N | |
| Q-17 ($R_5$ = H, $R_6$ = $CH_3$) | 1 | H | H | $OCH_3$ | $OCH_3$ | N | |
| Q-18 ($R_5$ = H, $R_6$ = $CH_3$) | 1 | H | H | $OCH_3$ | $OCH_3$ | N | |
| Q-22 ($R_5$, $R_6$, $R_7$ = H) | 1 | H | H | $OCH_3$ | $CH_3$ | N | |
| Q-26 (W' = S) | 1 | H | H | $OCH_3$ | $OCH_3$ | N | |
| Q-27 ($R_5$, $R_6$ = H, n' = 1) | 1 | H | H | $OCH_3$ | $OCH_3$ | N | |
| Q-30 ($R_5$, $R_9$, $R_{10}$ = H) | 1 | H | H | $OCH_3$ | $OCH_3$ | N | |
| Q-33 ($R_5$, $R_6$ = H) | 1 | H | H | $OCH_3$ | $OCH_3$ | N | |
| $C_6H_5$ | 1 | H | H | $CH_3$ | $OCH_3$ | N | |
| $C_6H_5$ | 1 | H | H | $OCH_3$ | $OCH_3$ | N | |
| Q-2 ($R_5$, $R_6$ = H) | 1 | H | 5-Cl | $OCH_3$ | $OCH_3$ | N | |
| Q-16 ($R_5$ = H, $R_6$ = $CH_3$) | 1 | H | 5-Br | $OCH_3$ | $OCH_3$ | CH | |
| Q-8 ($R_5'$ = $SCH_3$) | 1 | H | 5-$CH_3$ | $OCH_3$ | $OCH_3$ | CH | |
| Q-8 ($R_5'$ = $SCH_3$) | 1 | H | 5-Cl | $OCH_3$ | $CH_3$ | N | |
| Q-1 ($R_5$, $R_6$ = H) | 1 | $CH_3$ | 5-$CH_3$ | $OCH_3$ | $CH_3$ | N | |
| Q-1 ($R_5$, $R_6$ = H) | 1 | $CH_3$ | H | $OCH_3$ | $CH_3$ | N | |
| Q-8 ($R_5'$ = $SCH_3$) | 1 | H | H | $OC_2H_5$ | $CH_3$ | CH | |
| Q-1 ($R_5$, $R_6$ = H) | 1 | H | H | F | $OCH_3$ | CH | |
| Q-2 ($R_5$, $R_6$ = H) | 1 | H | H | Br | $OCH_3$ | CH | |
| Q-3 ($R_5$, $R_6$ = H) | 1 | H | H | I | $OCH_3$ | CH | |
| Q-8 ($R_5'$, R = $SCH_3$) | 1 | H | H | $OCF_2H$ | $OCH_3$ | CH | |
| Q-10 ($R_5$ = $CH_3$) | 1 | H | H | $CH_2F$ | $OCH_3$ | CH | |
| Q-18 ($R_5$ = H, $R_6$ = $CH_3$) | 1 | H | H | $OCH_2CH_2F$ | $CH_3$ | CH | |
| Q-17 ($R_5$ = H, $R_6$ = $CH_3$) | 1 | H | H | $OCH_2CHF_2$ | $CH_3$ | CH | |
| Q-8 ($R_5'$ = $SCH_3$) | 1 | H | H | $OCH_2CF_3$ | $OCH_3$ | CH | |
| Q-10 ($R_5$ = $CH_3$) | 1 | H | H | $CF_3$ | $OCH_3$ | CH | |
| Q-2 ($R_5$, $R_6$ = H) | 1 | H | H | $OCH_2CH_3$ | $OCH_3$ | N | |
| Q-1 ($R_5$, $R_6$ = H) | 1 | H | H | $OCH_2CH_2F$ | $CH_3$ | N | |
| Q-8 ($R_5'$ = $SCH_3$) | 1 | H | H | $OCH_2CF_3$ | $OCH_3$ | N | |
| Q-9 ($R_5$ = $CH_3$) | 1 | H | H | $OCH_3$ | H | CH | |
| Q-16 ($R_5$, $R_6$ = H) | 1 | H | H | $CH_3$ | $OC_2H_5$ | CH | |
| Q-8 ($R_5'$ = $SCH_3$) | 1 | H | H | $CH_3$ | $CH_2OCH_3$ | CH | |
| Q-8 ($R_5'$ = $CH_3$) | 1 | H | H | $OC_2H_5$ | $NHCH_3$ | N | |
| Q-17 | 1 | H | H | $OCH_3$ | $N(OCH_3)CH_3$ | N | |
| Q-8 ($R_5'$ = $SCH_3$) | 1 | H | H | $OCH_3$ | $N(CH_3)_2$ | N | |
| Q-18 ($R_5$ = H, $R_6$ = $CH_3$) | 1 | H | H | $OCH_3$ | $C_2H_5$ | CH | |
| Q-12 ($R_8$ = Cl) | 1 | H | H | $OCH_3$ | $CF_3$ | CH | |
| Q-11 ($R_5$ = $CH_3$) | 1 | H | H | $OCH_3$ | $SCH_3$ | N | |
| Q-18 ($R_5$ = H, $R_6$ = $CH_3$) | 1 | H | H | $CH_3$ | $OCH_2CH=CH_2$ | N | |
| Q-10 ($R_5$ = $CH_3$) | 1 | H | H | $CH_3$ | $OCH_2C\equiv CH$ | N | |
| Q-13 ($R_5$ = $CH_3$) | 1 | H | H | $OCH_3$ | $CH_2OCH_2CH_3$ | CH | |
| Q-17 ($R_5$ = H, $R_6$ = $CH_3$) | 1 | H | H | $CH_3$ | $OCH_2CH_2OCH_3$ | CH | |
| Q-14 ($R_5$ = H) | 1 | H | H | $CH_3$ | $CH_2SCH_3$ | CH | |
| Q-1 ($R_5$, $R_6$ = H) | 1 | H | H | $OCH_3$ | $i$-$C_3H_7$ | CH | |
| Q-10 ($R_5$ = $CH_3$) | 1 | H | H | $CH_3$ | $\overset{O}{\underset{\|}{C}}H$ | CH | |
| Q-1 ($R_5$, $R_6$ = H) | 1 | H | H | $CH_3$ | $\overset{O}{\underset{\|}{C}}CH_3$ | CH | |
| Q-8 ($R_5'$ = $SCH_3$) | 1 | H | H | $OCH_3$ | $CH(OCH_3)_2$ | CH | |
| Q-1 ($R_5$, $R_6$ = H) | 1 | H | H | $CH_3$ | $CH(OCH_3)_2$ | N | |
| Q-8 ($R_5$ = $SCH_3$) | 1 | H | H | $OCH_3$ | $CH(OC_2H_5)_2$ | CH | |
| Q-2 ($R_5$, $R_6$ = H) | 1 | H | H | $OCH_3$ | $CH(SCH_3)_2$ | CH | |
| Q-3 ($R_5$, $R_6$ = H) | 1 | H | H | $OCH_3$ | $C(CH_3)(OCH_3)_2$ | CH | |
| Q-8 ($R_5'$ = $SCH_3$) | 1 | H | H | $OCH_3$ | 1,3-dioxolan-2-yl | CH | |
| Q-18 ($R_5$ = H, $R_6$ = $CH_3$) | 1 | H | H | $CH_3$ | 1,3-dioxan-2-yl | CH | |

TABLE Ia-continued

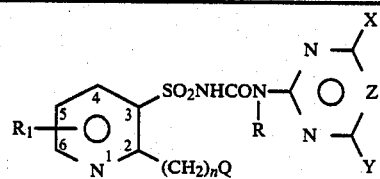

| Q | n | R | R₁ | X | Y | Z | m.p. °C. |
|---|---|---|---|---|---|---|---|
| Q-17 (R₅ = H, R₆ = CH₃) | 1 | H | H | OCH₃ | ![O-CH(-S-)CH₂CH₂ ring] | | |
| Q-8 (R₅' = CH₃) | 1 | H | H | OCH₃ | ![O-CH(-O-)CH(CH₃)CH₂ ring] | CH | |
| Q-10 (R₅ = H) | 1 | H | H | OCH₃ | OCF₂H | CH | |
| Q-14 (R₅ = H) | 1 | H | H | OCH₃ | SCF₂H | CH | |
| Q-8 (R₅' = SCH₃) | 1 | H | H | OCH₃ | cyclopropyl (CH₂-CH-CH₂) | N | |
| Q-1 (R₅, R₆ = H) | 1 | H | H | OCH₃ | cyclopropyl | CH | |
| C₆H₅ | 1 | H | H | OCH₃ | cyclopropyl | N | |
| C₆H₅ | 1 | H | H | OCH₃ | cyclopropyl | CH | |
| Q-35 (R₁₁ = R₁₂ = OCH₃) | 1 | H | H | OCH₃ | cyclopropyl | CH | |
| Q-39 (R₅ = R₆ = H) | 1 | H | H | OCH₃ | cyclopropyl | CH | |
| Q-1 (R₅, R₆ = H) | 2 | H | H | OCH₃ | OCH₃ | CH | |
| Q-5 (R, R₆ = H) | 2 | H | H | OCH₃ | OCH₃ | CH | |
| Q-8 (R₅' = H) | 2 | H | H | OCH₃ | OCH₃ | CH | |
| Q-14 (R₅ = H) | 2 | H | H | OCH₃ | OCH₃ | CH | |
| Q-16 (R₅ = H, R₆ = CH₃) | 2 | H | H | OCH₃ | OCH₃ | CH | |
| Q-1 (R₅, R₆ = H) | 2 | H | H | OCH₃ | OCH₃ | N | |
| Q-10 (R₅ = H) | 2 | H | H | OCH₃ | OCH₃ | N | |
| Q-12 (R₈ = H) | 2 | H | H | CH₃ | OCH₃ | N | |
| Q-18 (R₅ = H, R₆ = CH₃) | 2 | H | H | OCH₃ | OCH₃ | N | |
| Q-24 (R₅, R₆, R₇ = H) | 2 | H | H | OCH₃ | OCH₃ | N | |
| Q-27 (R₅, R₆ = H, n' = 1) | 2 | H | H | OCH₃ | CH₃ | N | |
| Q-33 (R₅, R₆, = H) | 2 | H | H | OCH₃ | OCH₃ | N | |
| Q-37 (R₅, R₆ = H) | 2 | H | H | OCH₃ | OCH₃ | CH | |
| Q-7 (R₅, R₇ = CH₃, R₆ = H) | 0 | H | H | CH₃ | OCH₃ | CH | 220–224 |
| Q-7 (R₅, R₇ = CH₃, R₆ = H) | 0 | H | H | CH₃ | CH₃ | CH | 212–216 |
| Q-7 (R₅, R₇ = CH₃, R₆ = H) | 0 | H | H | Cl | OCH₃ | CH | 193–195 |
| Q-7 (R₅, R₇ = CH₃, R₆ = H) | 0 | H | H | OCH₃ | OCH₃ | N | 190–193 |

TABLE Ib

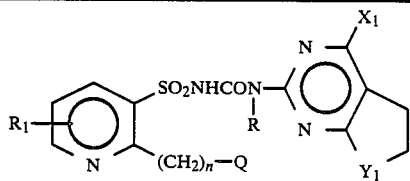

| Q | n | R | R$_1$ | X$_1$ | Y$_1$ | m.p. °C. |
|---|---|---|---|---|---|---|
| Q-1(R$_5$, R$_6$ = H) | 0 | H | H | CH$_3$ | O | |
| Q-2(R$_5$, R$_6$ = H) | 0 | H | H | CH$_3$ | O | |
| Q-3(R$_5$, R$_6$ = H) | 0 | H | H | CH$_3$ | O | |
| Q-4(R$_5$, R$_6$ = H) | 0 | H | H | CH$_3$ | O | |
| Q-7(R$_5$, R$_6$, R$_7$ = H) | 0 | H | H | CH$_3$ | O | |
| Q-8(R$_5$' = SCH$_3$) | 0 | H | H | CH$_3$ | O | |
| Q-8(R$_5$' = CH$_3$) | 0 | H | H | CH$_3$ | O | |
| Q-8(R$_5$' = H) | 0 | H | H | CH$_3$ | O | |
| Q-9(R$_5$ = CH$_3$) | 0 | H | H | CH$_3$ | O | |
| Q-10(R$_5$ = CH$_3$) | 0 | H | H | CH$_3$ | O | |
| Q-14(R$_5$ = H) | 0 | H | H | CH$_3$ | O | |
| Q-16(R$_5$, R$_6$ = H) | 0 | H | H | CH$_3$ | O | |
| Q-17(R$_5$, R$_6$ = H) | 0 | H | H | CH$_3$ | O | |
| Q-18(R$_5$, R$_6$ = H) | 0 | H | H | CH$_3$ | O | |
| Q-21(R$_5$, R$_6$, R$_7$ = H) | 0 | H | H | CH$_3$ | O | |
| Q-22(R$_5$, R$_6$, R$_7$ = H) | 0 | H | H | CH$_3$ | O | |
| Q-24(R$_5$, R$_6$, R$_7$ = H) | 0 | H | H | CH$_3$ | O | |
| Q-27(R$_5$, R$_6$ = H, n' = 0) | 0 | H | H | CH$_3$ | O | |
| Q-30(R$_5$, R$_9$, R$_{10}$ = H) | 0 | H | H | CH$_3$ | O | |
| Q-33(R$_5$, R$_6$ = H) | 0 | H | H | CH$_3$ | O | |
| Q-8(R$_5$' = SCH$_3$) | 0 | H | H | OCH$_3$ | O | |
| Q-1(R$_5$, R$_6$ = H) | 0 | H | H | OC$_2$H$_5$ | O | |
| Q-9(R$_5$ = CH$_3$) | 0 | H | H | OCF$_2$H | O | |
| Q-8(R$_5$' = CH$_3$) | 0 | H | H | OCH$_3$ | CH$_2$ | |
| Q-8(R$_5$' = SCH$_3$) | 0 | H | H | OCH$_3$ | CH$_2$ | |
| Q-1(R$_5$, R$_6$ = H) | 1 | H | H | CH$_3$ | O | |
| Q-2(R$_5$, R$_6$ = H) | 1 | H | H | CH$_3$ | O | |
| Q-8(R$_5$' = SCH$_3$) | 1 | H | H | CH$_3$ | O | |
| Q-8(R$_5$' = CH$_3$) | 1 | H | H | CH$_3$ | O | |
| Q-14(R$_5$ = H) | 1 | H | H | CH$_3$ | O | |
| Q-16(R$_5$, R$_6$ = H) | 1 | H | H | CH$_3$ | O | |
| Q-17(R$_5$, R$_6$ = H) | 1 | H | H | CH$_3$ | O | |
| Q-18(R$_5$, R$_6$ = H) | 1 | H | H | CH$_3$ | O | |
| Q-33(R$_5$, R$_6$ = H) | 1 | H | H | CH$_3$ | O | |
| Q-1(R$_5$, R$_6$ = H) | 1 | H | H | OC$_2$H$_5$ | O | |
| Q-8(R$_5$' = CH$_3$) | 1 | H | H | OCF$_2$H | O | |
| Q-8(R$_5$' = SCH$_3$) | 1 | H | H | OCH$_3$ | CH$_2$ | |
| Q-8(R$_5$' = CH$_3$) | 2 | H | H | CH$_3$ | O | |
| Q-14(R$_5$ = H) | 2 | H | H | CH$_3$ | O | |
| Q-8(R$_5$' = SCH$_3$) | 2 | H | H | OC$_2$H$_5$ | O | |
| Q-33, (R$_5$, R$_6$ = H) | 2 | H | H | CH$_3$ | O | |

TABLE Ic

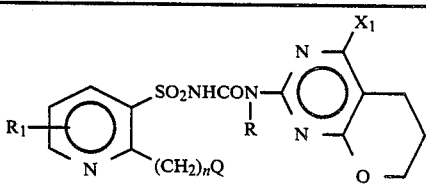

| Q | n | R | R$_1$ | X$_1$ | m.p. °C. |
|---|---|---|---|---|---|
| Q-1(R$_5$, R$_6$ = H) | 0 | H | H | CH$_3$ | |
| Q-2(R$_5$, R$_6$ = H) | 0 | H | H | OCH$_3$ | |
| Q-3(R$_5$, R$_6$ = H) | 0 | H | H | OC$_2$H$_5$ | |
| Q-4(R$_5$, R$_6$ = H) | 0 | H | H | CH$_3$ | |
| Q-7(R$_5$, R$_6$, R$_7$ = H) | 0 | H | H | CH$_3$ | |
| Q-8(R$_5$' = SCH$_3$) | 0 | H | H | OCH$_3$ | |
| Q-8(R$_5$' = CH$_3$) | 0 | H | H | OCH$_3$ | |
| Q-8(R$_5$' = H) | 0 | H | H | CH$_3$ | |
| Q-9(R$_5$ = CH$_3$) | 0 | H | H | OCF$_2$H | |
| Q-10(R$_5$ = CH$_3$) | 0 | H | H | CH$_3$ | |
| Q-14(R$_5$ = H) | 0 | H | H | OCH$_3$ | |
| Q-16(R$_5$ = H, R$_6$ = CH$_3$) | 0 | H | H | CH$_3$ | |
| Q-17(R$_5$ = H, R$_6$ = CH$_3$) | 0 | H | H | OCF$_2$H | |
| Q-18(R$_5$ = H, R$_6$ = CH$_3$) | 0 | H | H | OCH$_3$ | |

TABLE Ic-continued

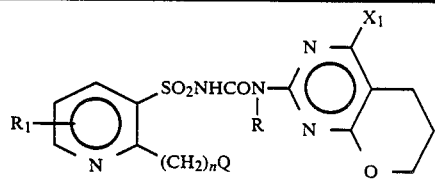

| Q | n | R | R$_1$ | X$_1$ | m.p. °C. |
|---|---|---|---|---|---|
| Q-21(R$_5$, R$_6$, R$_7$ = H) | 0 | H | H | OCH$_3$ | |
| Q-22(R$_5$, R$_6$, R$_7$ = H) | 0 | H | H | CH$_3$ | |
| Q-24(R$_5$, R$_6$, R$_7$ = H) | 0 | H | H | CH$_3$ | |
| Q-27(R$_5$, R$_6$ = H, n' = 0) | 0 | H | H | OCH$_3$ | |
| Q-30(R$_5$, R$_9$, R$_{10}$ = H) | 0 | H | H | OCH$_3$ | |
| Q-33(R$_5$, R$_6$ = H) | 0 | H | H | OCH$_3$ | |
| Q-1(R$_5$, R$_6$ = H) | 1 | H | H | CH$_3$ | |
| Q-2(R$_5$, R$_6$ = H) | 1 | H | H | OCH$_3$ | |
| Q-8(R$_5$' = CH$_3$) | 1 | H | H | OCH$_3$ | |
| Q-8(R$_5$' = SCH$_3$) | 1 | H | H | CH$_3$ | |
| Q-10(R$_5$ = CH$_3$) | 1 | H | H | OC$_2$H$_5$ | |
| Q-14(R$_5$ = H) | 1 | H | H | OCH$_3$ | |
| Q-17(R$_5$ = H, R$_6$ = CH$_3$) | 1 | H | H | OCF$_2$H | |
| Q-21(R$_5$, R$_6$, R$_7$ = H) | 1 | H | H | OCH$_3$ | |
| Q-33(R$_5$, R$_6$ = H) | 1 | H | H | OCH$_3$ | |
| Q-8(R$_5$' = CH$_3$) | 2 | H | H | CH$_3$ | |
| Q-27(R, R$_6$ = H, n' = 1) | 2 | H | H | OCH$_3$ | |
| Q-24(R$_5$, R$_6$ = H) | 2 | H | H | OCH$_3$ | |
| Q-1(R$_5$, R$_6$ = H) | 2 | H | H | CH$_3$ | |
| Q-4(R$_5$, R$_6$ = H) | 2 | H | H | OC$_2$H$_5$ | |

TABLE Id

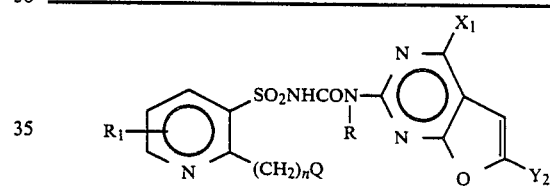

| Q | n | R | R$_1$ | X$_1$ | Y$_2$ | m.p. °C. |
|---|---|---|---|---|---|---|
| Q-1(R$_5$, R$_6$ = H) | 0 | H | H | CH$_3$ | CH$_3$ | |
| Q-2(R$_5$, R$_6$ = H) | 0 | H | H | OCH$_3$ | CH$_3$ | |
| Q-3(R$_5$, R$_6$ = H) | 0 | H | H | OC$_2$H$_5$ | H | |
| Q-4(R$_5$, R$_6$ = H) | 0 | H | H | CH$_3$ | CH$_3$ | |
| Q-7(R$_5$, R$_6$, R$_7$ = H) | 0 | H | H | CH$_3$ | CH$_3$ | |
| Q-8(R$_5$' = SCH$_3$) | 0 | H | H | CH$_3$ | CH$_3$ | |
| Q-8(R$_5$' = CH$_3$) | 0 | H | H | CH$_3$ | CH$_3$ | |
| Q-8(R$_5$' = H) | 0 | H | H | CH$_3$ | CH$_3$ | |
| Q-9(R$_5$ = CH$_3$) | 0 | H | H | OCF$_2$H | CH$_3$ | |
| Q-10(R$_5$ = CH$_3$) | 0 | H | H | CH$_3$ | CH$_3$ | |
| Q-14(R$_5$ = H) | 0 | H | H | CH$_3$ | CH$_3$ | |
| Q-16(R$_5$, R$_6$ = H) | 0 | H | H | CH$_3$ | CH$_3$ | |
| Q-17(R$_5$, R$_6$ = H) | 0 | H | H | OCF$_2$H | CH$_3$ | |
| Q-18(R$_5$, R$_6$ = H) | 0 | H | H | OC$_2$H$_5$ | CH$_3$ | |
| Q-21(R$_5$, R$_6$, R$_7$ = H) | 0 | H | H | CH$_3$ | CH$_3$ | |
| Q-22(R$_5$, R$_6$, R$_7$ = H) | 0 | H | H | OCH$_3$ | H | |
| Q-24(R$_5$, R$_6$, R$_7$ = H) | 0 | H | H | OCF$_2$H | CH$_3$ | |
| Q-27(R$_5$, R$_6$ = H, n' = 0) | 0 | H | H | CH$_3$ | CH$_3$ | |
| Q-30(R$_5$, R$_9$, R$_{10}$ = H) | 0 | H | H | CH$_3$ | CH$_3$ | |
| Q-33(R$_5$, R$_6$ = H) | 0 | H | H | CH$_3$ | CH$_3$ | |
| Q-1(R$_5$, R$_6$ = H) | 1 | H | H | CH$_3$ | CH$_3$ | |
| Q-2(R$_5$, R$_6$ = H) | 1 | H | H | OCH$_3$ | CH$_3$ | |
| Q-3(R$_5$, R$_6$ = H) | 1 | H | H | OC$_2$H$_5$ | H | |
| Q-8(R$_5$' = SCH$_3$) | 1 | H | H | CH$_3$ | CH$_3$ | |
| Q-8(R$_5$' = CH$_3$) | 1 | H | H | CH$_3$ | CH$_3$ | |
| Q-14(R$_5$ = H) | 1 | H | H | CH$_3$ | CH$_3$ | |
| Q-16(R$_5$, R$_6$ = H) | 1 | H | H | CH$_3$ | CH$_3$ | |
| Q-18(R$_5$, R$_6$ = H) | 1 | H | H | OC$_2$H$_5$ | CH$_3$ | |
| Q-21(R$_5$, R$_6$, R$_7$ = H) | 1 | H | H | CH$_3$ | CH$_3$ | |
| Q-27(R$_5$, R$_6$ = H) | 1 | H | H | CH$_3$ | CH$_3$ | |
| Q-33(R$_5$, R$_6$ = H) | 1 | H | H | CH$_3$ | CH$_3$ | |
| Q-38(R$_5$, R$_6$ = H) | 1 | H | H | CH$_3$ | CH$_3$ | |
| Q-1(R$_5$, R$_6$ = H) | 2 | H | H | CH$_3$ | CH$_3$ | |
| Q-8(R$_5$' = SCH$_3$) | 2 | H | H | CH$_3$ | CH$_3$ | |
| Q-8(R$_5$' = CH$_3$) | 2 | H | H | CH$_3$ | CH$_3$ | |

TABLE Id-continued

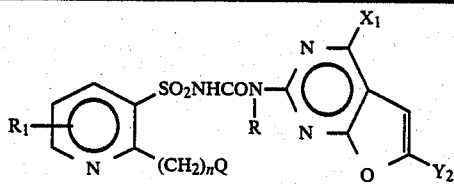

| Q | n | R | R₁ | X₁ | Y₂ | m.p. °C. |
|---|---|---|----|----|----|----------|
| Q-14 | 2 | H | H | OCH₃ | CH₃ | |
| Q-33(R₅, R₆ = H) | 2 | H | H | CH₃ | CH₃ | |

TABLE Ie

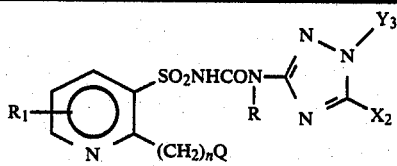

| Q | n | R | R₁ | X₂ | Y₃ | m.p. °C. |
|---|---|---|----|----|----|----------|
| Q-1(R₅, R₆ = H) | 0 | H | H | CH₃ | CH₃ | |
| Q-2(R₅, R₆ = H) | 0 | H | H | OCH₃ | CH₃ | |
| Q-3(R₅, R₆ = H) | 0 | H | H | OCH₃ | C₂H₅ | |
| Q-4(R₅, R₆ = H) | 0 | H | H | CH₃ | CH₃ | |
| Q-7(R₅, R₆, R₇ = H) | 0 | H | H | CH₃ | CH₃ | |
| Q-8(R₅' = SCH₃) | 0 | H | H | CH₃ | CH₂CF₃ | |
| Q-8(R₅' = CH₃) | 0 | H | H | CH₃ | CH₂CF₃ | |
| Q-8(R₅' = H) | 0 | H | H | CH₃ | CH₃ | |
| Q-9(R₅ = CH₃) | 0 | H | H | OCH₃ | CH₃ | |
| Q-10(R₅ = CH₃) | 0 | H | H | CH₃ | CH₃ | |
| Q-14(R₅ = H) | 0 | H | H | CH₃ | C₂H₅ | |
| Q-16(R₅ = H, R₆ = CH₃) | 0 | H | H | CH₃ | CH₃ | |
| Q-17(R₅ = H, R₆ = CH₃) | 0 | H | H | OCH₃ | CH₂CF₃ | |
| Q-18(R₅ = H, R₆ = CH₃) | 0 | H | H | OCH₃ | CH₃ | |
| Q-21(R₅, R₆, R₇ = H) | 0 | H | H | CH₃ | CH₃ | |
| Q-22(R₅, R₆, R₇ = H) | 0 | H | H | OCH₃ | C₂H₅ | |
| Q-24(R₅, R₆, R₇ = H) | 0 | H | H | OCH₃ | CH₃ | |
| Q-27(R₅, R₆ = H, n' = 1) | 0 | H | H | CH₃ | CH₃ | |
| Q-30(R₅, R₉, R₁₀ = H) | 0 | H | H | CH₃ | CH₃ | |
| Q-33(R₅, R₆ = H) | 0 | H | H | CH₃ | CH₃ | |
| Q-1(R₅, R₆ = H) | 1 | H | H | CH₃ | CH₃ | |
| Q-2(R₅, R₆ = H) | 1 | H | H | OCH₃ | CH₃ | |
| Q-8(R₅' = CH₃) | 1 | H | H | CH₃ | C₂H₅ | |
| Q-8(R₅' = SCH₃) | 1 | H | H | CH₃ | CH₂CF₃ | |
| Q-9(R₅ = CH₃) | 1 | H | H | OCH₃ | CH₃ | |
| Q-10(R₅ = CH₃) | 1 | H | H | CH₃ | CH₃ | |
| Q-14(R₅ = H) | 1 | H | H | CH₃ | C₂H₅ | |
| Q-16(R₅ = H, R₆ = CH₃) | 1 | H | H | CH₃ | CH₃ | |
| Q-27(R₅, R₆ = H) | 1 | H | H | CH₃ | CH₃ | |
| Q-33(R₅, R₆ = H) | 1 | H | H | CH₃ | CH₃ | |
| Q-1(R₅, R₆ = H) | 2 | H | H | CH₃ | CH₃ | |
| Q-8(R₅' = CH₃) | 2 | H | H | OCH₃ | CH₃ | |
| Q-14 | 2 | H | H | CH₃ | CH₃ | |
| Q-18 | 2 | H | H | OCH₃ | CH₂CF₃ | |

TABLE If

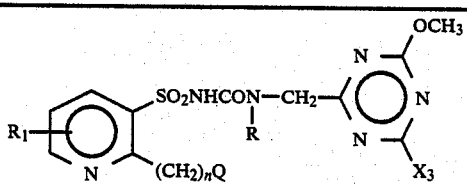

| Q | n | R | R₁ | X₃ | m.p. °C. |
|---|---|---|----|----|----------|
| Q-1 (R₅, R₆ = H) | 0 | H | H | CH₃ | |
| Q-2 (R₅, R₆ = H) | 0 | H | H | CH₃ | |
| Q-3 (R₅, R₆ = H) | 0 | H | H | CH₃ | |
| Q-4 (R₅, R₆ = H) | 0 | H | H | OCH₃ | |

TABLE If-continued

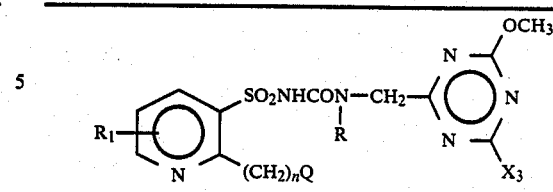

| Q | n | R | R₁ | X₃ | m.p. °C. |
|---|---|---|----|----|----------|
| Q-7 (R₅, R₆, R₇ = H) | 0 | H | H | OCH₃ | |
| Q-9 (R₅' = CH₃) | 0 | H | H | CH₃ | |
| Q-8 (R₅' = SCH₃) | 0 | H | H | OCH₃ | |
| Q-8 (R₅' = CH₃) | 0 | H | H | CH₃ | |
| Q-9 (R₅ = CH₃) | 0 | H | H | CH₃ | |
| Q-10 (R₅ = CH₃) | 0 | H | H | OCH₃ | |
| Q-14 (R₅ = H) | 0 | H | H | OCH₃ | |
| Q-16 (R₅, R₆ = H) | 0 | H | H | CH₃ | |
| Q-17 (R₅, R₆ = H) | 0 | H | H | CH₃ | |
| Q-18 (R₅, R₆ = H) | 0 | H | H | OCH₃ | |
| Q-21 (R₅, R₆, R₇ = H) | 0 | H | H | CH₃ | |
| Q-22 (R₅, R₆, R₇ = H) | 0 | H | H | OCH₃ | |
| Q-24 (R₅, R₆, R₇ = H) | 0 | H | H | CH₃ | |
| Q-27 (R₅, R₆ = H, n' = 0) | 0 | H | H | CH₃ | |
| Q-30 (R₅, R₉, R₁₀ = H) | 0 | H | H | OCH₃ | |
| Q-33 (R₅, R₆ = H) | 0 | H | H | CH₃ | |
| Q-38 (R₅, R₆ = H) | 0 | H | H | CH₃ | |
| Q-1 (R₅, R₆ = H) | 1 | H | H | OCH₃ | |
| Q-2 (R₅, R₆ = H) | 1 | H | H | CH₃ | |
| Q-8 (R₅' = CH₃) | 1 | H | H | CH₃ | |
| Q-8 (R₅' = SCH₃) | 1 | H | H | OCH₃ | |
| Q-10 (R₅ = CH₃) | 1 | H | H | CH₃ | |
| Q-14 (R₅ = H) | 1 | H | H | CH₃ | |
| Q-16 (R₅, R₆ = H) | 1 | H | H | OCH₃ | |
| Q-18 (R₅, R₆ = H) | 1 | H | H | OCH₃ | |
| Q-27 (R₅, R₆ = H) | 1 | H | H | CH₃ | |
| Q-38 (R₅, R₆ = H) | 1 | H | H | OCH₃ | |
| Q-1 (R₅, R₆ = H) | 2 | H | H | OCH₃ | |
| Q-8 (R₅' = CH₃) | 2 | H | H | OCH₃ | |

TABLE Iq

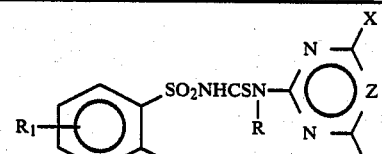

| Q | n | R | R₁ | X | Y | Y | m.p. °C. |
|---|---|---|----|----|----|----|----------|
| Q-1 (R₅, R₆ = H) | 0 | H | H | OCH₃ | OCH₃ | CH | |
| Q-1 (R₅, R₆ = H) | 1 | H | H | OCH₃ | OCH₃ | CH | |
| Q-2 (R₅, R₆ = H) | 0 | H | H | OCH₃ | CH₃ | CH | |
| Q-3 (R₅, R₆ = H) | 0 | H | H | OCH₃ | OCH₃ | CH | |
| Q-4 (R₅, R₆ = H) | 0 | H | H | OCH₃ | OCH₃ | CH | |
| Q-1 (R₅, R₆ = H) | 0 | H | H | CH₃ | OCH₃ | N | |
| Q-8 (R₅' = CH₃) | 0 | H | H | OCH₃ | CH₃ | CH | |
| Q-9 (R₅ = CH₃) | 0 | H | H | OCH₃ | OCH₃ | CH | |
| Q-10 (R₅ = CH₃) | 0 | H | H | CH₃ | OCH₃ | CH | |
| Q-14 (R₅ = H) | 0 | H | H | OCH₃ | OCH₃ | CH | |
| Q-16 (R₅, R₆ = H) | 0 | H | H | OCH₃ | OCH₃ | CH | |
| Q-17 (R₅ = H, R₆ = CH₃) | 0 | H | H | OCH₃ | OCH₃ | CH | |
| Q-21 (R₅, R₆, R₇ = H) | 0 | H | H | OCH₃ | OCH₃ | CH | |
| Q-22 (R₅, R₆, R₇ = H) | 0 | H | H | OCH₃ | OCH₃ | CH | |
| Q-24 (R₅, R₆, R₇ = H) | 0 | H | H | OCH₃ | OCH₃ | CH | |
| Q-33 (R₅, R₆ = H) | 0 | H | H | OCH₃ | OCH₃ | CH | |
| Q-8 (R₅' = CH₃) | 1 | H | H | OCH₃ | OCH₃ | CH | |
| Q-8 (R₅' = CH₃) | 1 | H | H | OCH₃ | CH₃ | N | |
| Q-8 (R₅' = CH₃) | 0 | H | H | CH₃ | OCH₃ | N | |
| Q-8 (R₅' = CH₃) | 2 | H | H | OCH₃ | OCH₃ | CH | |

TABLE IIa

| Q | n | R | R₁ | X | Y | Z | m.p. °C. |
|---|---|---|---|---|---|---|---|
| Q-1 (R₅, R₆ = H) | 0 | CH₃ | H | OCH₃ | OCH₃ | CH | |
| Q-1 (R₅, R₆ = H) | 0 | H | H | CH₃ | CH₃ | CH | |
| Q-1 (R₅, R₆ = H) | 0 | H | H | CH₃ | OCH₃ | CH | |
| Q-1 (R₅, R₆ = H) | 0 | H | H | OCH₃ | OCH₃ | CH | |
| Q-1 (R₅, R₆ = H) | 0 | H | H | Cl | OCH₃ | CH | |
| Q-1 (R₅ = H, R₆ = CH₃) | 0 | H | H | OCH₃ | OCH₃ | CH | |
| Q-1 (R₅ = CH₃, R₆ = H) | 0 | H | H | OCH₃ | OCH₃ | CH | |
| Q-2 (R₅, R₆ = H) | 0 | H | H | CH₃ | CH₃ | CH | |
| Q-2 (R₅, R₆ = H) | 0 | H | H | OCH₃ | OCH₃ | CH | |
| Q-2 (R₅, R₆ = H) | 0 | H | H | CH₃ | OCH₃ | CH | |
| Q-2 (R₅, R₆ = H) | 0 | H | H | Cl | OCH₃ | CH | |
| Q-2 (R₅ = CH₃, R₆ = H) | 0 | H | H | OCH₃ | OCH₃ | CH | |
| Q-2 (R₅ = H, R₆ = CH₃) | 0 | H | H | OCH₃ | OCH₃ | CH | |
| Q-3 (R₅, R₆ = H) | 0 | H | H | CH₃ | CH₃ | CH | |
| Q-3 (R₅, R₆ = H) | 0 | H | H | CH₃ | OCH₃ | CH | |
| Q-3 (R₅, R₆ = H) | 0 | H | H | OCH₃ | OCH₃ | CH | |
| Q-3 (R₅, R₆ = H) | 0 | H | H | Cl | OCH₃ | CH | |
| Q-3 (R₅ = CH₃, R₆ = H) | 0 | H | H | OCH₃ | OCH₃ | CH | |
| Q-4 (R₅, R₆ = H) | 0 | H | H | CH₃ | CH₃ | CH | |
| Q-4 (R₅, R₆ = H) | 0 | H | H | OCH₃ | CH₃ | CH | |
| Q-4 (R₅, R₆ = H) | 0 | H | H | OCH₃ | OCH₃ | CH | |
| Q-4 (R₅, R₆ = H) | 0 | H | H | Cl | OCH₃ | CH | |
| Q-5 (R₅, R₆ = H) | 0 | H | H | OCH₃ | OCH₃ | CH | |
| Q-5 (R₅, R₆ = H) | 0 | H | H | CH₃ | CH₃ | CH | |
| Q-5 (R₅, R₆ = H) | 0 | H | H | CH₃ | OCH₃ | CH | |
| Q-5 (R₅, R₆ = H) | 0 | H | H | Cl | OCH₃ | CH | |
| Q-6 (R₅ = H) | 0 | H | H | OCH₃ | OCH₃ | CH | |
| Q-6 (R₅ = H) | 0 | H | H | CH₃ | OCH₃ | CH | |
| Q-6 (R₅ = H) | 0 | H | H | CH₃ | CH₃ | CH | |
| Q-6 (R₅ = H) | 0 | H | H | Cl | OCH₃ | CH | |
| Q-7 (R₅, R₆, R₇ = H) | 0 | H | H | CH₃ | CH₃ | CH | |
| Q-7 (R₅, R₆, R₇ = H) | 0 | H | H | OCH₃ | OCH₃ | CH | |
| Q-7 (R₅, R₆, R₇ = H) | 0 | H | H | CH₃ | OCH₃ | CH | |
| Q-7 (R₅, R₆, R₇ = H) | 0 | H | H | Cl | OCH₃ | CH | |
| Q-7 (R₅, R₇ = CH₃; R₆ = H) | 0 | H | H | OCH₃ | OCH₃ | CH | |
| Q-8 (R₅' = H) | 0 | H | H | CH₃ | CH₃ | CH | |
| Q-8 (R₅' = H) | 0 | H | H | OCH₃ | OCH₃ | CH | |
| Q-8 (R₅' = H) | 0 | H | H | CH₃ | OCH₃ | CH | |
| Q-8 (R₅' = H) | 0 | H | H | Cl | OCH₃ | CH | |
| Q-8 (R₅' = CH₃) | 0 | H | H | OCH₃ | OCH₃ | CH | |
| Q-8 (R₅' = CH₃) | 0 | H | H | CH₃ | OCH₃ | CH | |
| Q-8 (R₅' = CH₃) | 0 | H | H | CH₃ | CH₃ | CH | |
| Q-8 (R₅' = CH₃) | 0 | H | H | Cl | OCH₃ | CH | |
| Q-8 (R₅' = CH₃) | 0 | CH₃ | H | OCH₃ | OCH₃ | CH | |
| Q-8 (R₅' = C₂H₅) | 0 | H | H | CH₃ | CH₃ | CH | |
| Q-8 (R₅' = C₂H₅) | 0 | H | H | OCH₃ | OCH₃ | CH | |
| Q-8 (R₅' = C₂H₅) | 0 | H | H | CH₃ | OCH₃ | CH | |
| Q-8 (R₅' = C₂H₅) | 0 | H | H | Cl | OCH₃ | CH | |
| Q-8 (R₅' = SCH₃) | 0 | H | H | OCH₃ | OCH₃ | CH | |
| Q-8 (R₅' = SCH₃) | 0 | H | H | CH₃ | OCH₃ | CH | |
| Q-8 (R₅' = SCH₃) | 0 | H | H | CH₃ | CH₃ | CH | |
| Q-8 (R₅' = SCH₃) | 0 | H | H | Cl | OCH₃ | CH | |
| Q-8 (R₅' = SC₂H₅) | 0 | H | H | CH₃ | CH₃ | CH | |
| Q-8 (R₅' = SC₂H₅) | 0 | H | H | OCH₃ | OCH₃ | CH | |
| Q-8 (R₅' = SC₂H₅) | 0 | H | H | CH₃ | OCH₃ | CH | |
| Q-8 (R₅' = SC₂H₅) | 0 | H | H | Cl | OCH₃ | CH | |
| Q-8 (R₅' = SCH₂CH=CH₂) | 0 | H | H | OCH₃ | OCH₃ | CH | |
| Q-8 (R₅' = SCH₂CH=CH₂) | 0 | H | H | CH₃ | OCH₃ | CH | |
| Q-8 (R₅' = SCH₂CH=CH₂) | 0 | H | H | CH₃ | CH₃ | CH | |
| Q-8 (R₅' = SCH₂CH=CH₂) | 0 | H | H | Cl | OCH₃ | CH | |
| Q-8 (R₅' = SCF₂H) | 0 | H | H | OCH₃ | OCH₃ | CH | |
| Q-8 (R₅' = SCF₂H) | 0 | H | H | CH₃ | CH₃ | CH | |
| Q-8 (R₅' = SCF₂H) | 0 | H | H | OCH₃ | CH₃ | CH | |
| Q-8 (R₅' = SCF₂H) | 0 | H | H | Cl | OCH₃ | CH | |
| Q-8 (R₅' = SC₃H₇) | 0 | H | H | OCH₃ | OCH₃ | CH | |
| Q-8 (R₅' = SC₃H₇) | 0 | H | H | CH₃ | OCH₃ | CH | |
| Q-8 (R₅' = SC₃H₇) | 0 | H | H | Cl | OCH₃ | CH | |
| Q-8 (R₅' = OCH₃) | 0 | H | H | OCH₃ | OCH₃ | CH | |
| Q-8 (R₅' = OC₂H₅) | 0 | H | H | OCH₃ | OCH₃ | CH | |
| Q-9 (R₅ = H) | 0 | H | H | OCH₃ | OCH₃ | CH | |
| Q-9 (R₅ = H) | 0 | H | H | CH₃ | OCH₃ | CH | |

TABLE IIa-continued structure: R₁-[pyridine with (CH₂)ₙQ and SO₂NHCON(R)-heterocycle with X, Y, Z]

| Q | n | R | R₁ | X | Y | Z | m.p. °C. |
|---|---|---|----|---|---|---|----------|
| Q-9 (R₅ = H) | 0 | H | H | CH₃ | CH₃ | CH | |
| Q-9 (R₅ = H) | 0 | H | H | Cl | OCH₃ | CH | |
| Q-9 (R₅ = CH₃) | 0 | H | H | OCH₃ | OCH₃ | CH | |
| Q-9 (R₅ = CH₃) | 0 | H | H | CH₃ | OCH₃ | CH | |
| Q-9 (R₅ = CH₃) | 0 | H | H | CH₃ | CH₃ | CH | |
| Q-9 (R₅ = CH₃) | 0 | H | H | Cl | OCH₃ | CH | |
| Q-10 (R₅ = H) | 0 | H | H | CH₃ | CH₃ | CH | |
| Q-10 (R₅ = H) | 0 | H | H | OCH₃ | OCH₃ | CH | |
| Q-10 (R₅ = H) | 0 | H | H | CH₃ | OCH₃ | CH | |
| Q-10 (R₅ = H) | 0 | H | H | Cl | OCH₃ | CH | |
| Q-10 (R₅ = CH₃) | 0 | H | H | CH₃ | CH₃ | CH | 160–165 |
| Q-10 (R₅ = CH₃) | 0 | H | H | OCH₃ | OCH₃ | CH | 169–173 |
| Q-10 (R₅ = CH₃) | 0 | H | H | CH₃ | OCH₃ | CH | |
| Q-10 (R₅ = CH₃) | 0 | H | H | Cl | OCH₃ | CH | 162–166 |
| Q-11 (R₅ = H) | 0 | H | H | OCH₃ | OCH₃ | CH | |
| Q-12 (R₈ = H) | 0 | H | H | OCH₃ | OCH₃ | CH | |
| Q-12 (R₈ = Cl) | 0 | H | H | OCH₃ | OCH₃ | CH | |
| Q-13 (R₅ = CH₃) | 0 | H | H | OCH₃ | OCH₃ | CH | |
| Q-14 (R₅ = H) | 0 | H | H | OCH₃ | OCH₃ | CH | |
| Q-14 (R₅ = H) | 0 | H | H | CH₃ | OCH₃ | CH | |
| Q-14 (R₅ = H) | 0 | H | H | Cl | OCH₃ | CH | |
| Q-15 (R₅ = H) | 0 | H | H | OCH₃ | OCH₃ | CH | |
| Q-16 (R₅, R₆ = H) | 0 | H | H | CH₃ | CH₃ | CH | |
| Q-16 (R₅, R₆ = H) | 0 | H | H | OCH₃ | OCH₃ | CH | |
| Q-16 (R₅, R₆ = H) | 0 | H | H | CH₃ | OCH₃ | CH | |
| Q-16 (R₅, R₆ = H) | 0 | H | H | Cl | OCH₃ | CH | |
| Q-17 (R₅, R₆ = H) | 0 | H | H | OCH₃ | OCH₃ | CH | |
| Q-17 (R₅, R₆ = H) | 0 | H | H | CH₃ | OCH₃ | CH | |
| Q-17 (R₅, R₆ = H) | 0 | H | H | CH₃ | CH₃ | CH | |
| Q-17 (R₅, R₆ = H) | 0 | H | H | Cl | OCH₃ | CH | |
| Q-18 (R₅, R₆ = H) | 0 | H | H | OCH₃ | OCH₃ | CH | |
| Q-18 (R₅, R₆ = H) | 0 | H | H | CH₃ | OCH₃ | CH | |
| Q-18 (R₅, R₆ = H) | 0 | H | H | CH₃ | CH₃ | CH | |
| Q-18 (R₅, R₆ = H) | 0 | H | H | Cl | OCH₃ | CH | |
| Q-19 (R₅ = CH₃, R₆ = H) | 0 | H | H | OCH₃ | OCH₃ | CH | |
| Q-20 (R₅, R₆ = CH₃) | 0 | H | H | OCH₃ | OCH₃ | CH | |
| Q-21 (R₅, R₆, R₇ = H) | 0 | H | H | OCH₃ | OCH₃ | CH | |
| Q-22 (R₅, R₆, R₇ = H) | 0 | H | H | OCH₃ | OCH₃ | CH | |
| Q-23 (R₅, R₆, R₇ = H) | 0 | H | H | OCH₃ | OCH₃ | CH | |
| Q-24 (R₅, R₆, R₇ = H) | 0 | H | H | OCH₃ | CH₃ | CH | |
| Q-25 (R₅, R₆, R₇ = H) | 0 | H | H | OCH₃ | OCH₃ | CH | |
| Q-26 (W' = O) | 0 | H | H | OCH₃ | OCH₃ | CH | |
| Q-27 (R₅, R₆ = H, n' = 0) | 0 | H | H | OCH₃ | OCH₃ | CH | |
| Q-28 (R₅, R₆ = H, n' = 0) | 0 | H | H | OCH₃ | OCH₃ | CH | |
| Q-29 (R₅, R₆ = H, n' = 0) | 0 | H | H | OCH₃ | OCH₃ | CH | |
| Q-30 (R₅ = H; R₉, R₁₀ = OCH₃) | 0 | H | H | OCH₃ | OCH₃ | CH | |
| Q-30 (R₅ = H; R₉, R₁₀ = CH₃) | 0 | H | H | OCH₃ | OCH₃ | CH | |
| Q-31 (R₉, R₁₀ = H) | 0 | H | H | OCH₃ | OCH₃ | CH | |
| Q-32 (R₉, R₁₀ = H) | 0 | H | H | OCH₃ | OCH₃ | CH | |
| Q-33 (R₅, R₆ = H) | 0 | H | H | OCH₃ | OCH₃ | CH | |
| Q-34 (R₅, R₆ = H) | 0 | H | H | OCH₃ | OCH₃ | CH | |
| Q-35 (R₁₁, R₁₂ = OCH₃) | 0 | H | H | OCH₃ | OCH₃ | CH | |
| Q-36 (R₁₁, R₁₂ = CH₃) | 0 | H | H | OCH₃ | OCH₃ | CH | |
| C₆H₅ | 0 | H | H | CH₃ | CH₃ | CH | |
| C₆H₅ | 0 | H | H | OCH₃ | CH₃ | CH | |
| C₆H₅ | 0 | H | H | OCH₃ | OCH₃ | CH | |
| C₆H₅ | 0 | H | H | Cl | OCH₃ | CH | |
| Q-1 (R₅, R₆ = H) | 0 | H | H | CH₃ | OCH₃ | N | |
| Q-2 (R₅, R₆ = H) | 0 | H | H | OCH₃ | OCH₃ | N | |
| Q-3 (R₅ = CH₃, R₆ = H) | 0 | H | H | OCH₃ | OCH₃ | N | |
| Q-8 (R₅' = CH₃) | 0 | H | H | CH₃ | OCH₃ | N | |
| Q-8 (R₅' = SCH₃) | 0 | H | H | OCH₃ | OCH₃ | N | |
| Q-9 (R₅ = CH₃) | 0 | H | H | CH₃ | OCH₃ | N | |
| Q-10 (R₅ = CH₃) | 0 | H | H | CH₃ | OCH₃ | N | |
| Q-12 (R₈ = Cl) | 0 | H | H | CH₃ | OCH₃ | N | |
| Q-17 | 0 | H | H | OCH₃ | CH₃ | N | |
| Q-18 | 0 | H | H | CH₃ | OCH₃ | N | |
| Q-18 | 0 | H | H | OCH₃ | OCH₃ | N | |
| Q-22 (R₅, R₆, R₇ = H) | 0 | H | H | CH₃ | OCH₃ | N | |
| Q-26 (W' = S) | 0 | H | H | CH₃ | OCH₃ | N | |
| Q-27 (R₅, R₆ = H, n' = 0) | 0 | H | H | CH₃ | OCH₃ | N | |

TABLE IIa-continued $$R_1 \text{-pyridine-}(CH_2)_nQ, SO_2NHCON(R)\text{-pyrimidine}(X,Y,Z)$$

| Q | n | R | $R_1$ | X | Y | Z | m.p. °C. |
|---|---|---|---|---|---|---|---|
| Q-27 ($R_5$, $R_6$ = H, n' = 0) | 0 | H | H | $OCH_3$ | $OCH_3$ | N | |
| Q-30 ($R_5$, $R_9$, $R_{10}$ = H) | 0 | H | H | $CH_3$ | $OCH_3$ | N | |
| Q-30 ($R_5$, $R_9$, $R_{10}$ = H) | 0 | H | H | $OCH_3$ | $OCH_3$ | N | |
| Q-33 ($R_5$, $R_6$ = H) | 0 | H | H | $CH_3$ | $OCH_3$ | N | |
| $C_6H_5$ | 0 | H | H | $CH_3$ | $OCH_3$ | N | |
| $C_6H_5$ | 0 | H | H | $OCH_3$ | $OCH_3$ | N | |
| $C_6H_5$ | 0 | H | H | $CH_3$ | $CH_3$ | N | |
| Q-2 ($R_5$, $R_6$ = H) | 0 | H | 5-Cl | $OCH_3$ | $OCH_3$ | CH | |
| Q-16 ($R_5$, $R_6$ = H) | 0 | H | 6-Br | $OCH_3$ | $OCH_3$ | CH | |
| Q-8 ($R_5'$ = $SCH_3$) | 0 | H | 5-$CH_3$ | $OCH_3$ | $OCH_3$ | CH | |
| Q-8 ($R_5'$ = $SCH_3$) | 0 | H | 5-Cl | $OCH_3$ | $CH_3$ | N | |
| Q-1 ($R_5$, $R_6$ = H) | 0 | H | 5-$CH_3$ | $OCH_3$ | $CH_3$ | N | |
| Q-1 ($R_5$, $R_6$ = H) | 0 | $CH_3$ | H | $OCH_3$ | $CH_3$ | N | |
| Q-8 ($R_5'$ = $SCH_3$) | 0 | H | H | $OC_2H_5$ | $CH_3$ | CH | |
| Q-1 ($R_5$, $R_6$ = H) | 0 | H | H | F | $OCH_3$ | CH | |
| Q-2 ($R_5$, $R_6$ = H) | 0 | H | H | Br | $OCH_3$ | CH | |
| Q-3 ($R_5$, $R_6$ = H) | 0 | H | H | I | $OCH_3$ | CH | |
| Q-8 ($R_5'$ = $SCH_3$) | 0 | H | H | $OCF_2H$ | $OCH_3$ | CH | |
| Q-10 ($R_5$ = $CH_3$) | 0 | H | H | $CH_2F$ | $OCH_3$ | CH | |
| Q-18 ($R_5$ = H, $R_6$ = $CH_3$) | 0 | H | H | $OCH_2CH_2F$ | $CH_3$ | CH | |
| Q-17 ($R_5$ = H, $R_6$ = $CH_3$) | 0 | H | H | $OCH_2CHF_2$ | $CH_3$ | CH | |
| Q-8 ($R_5'$ = $SCH_3$) | 0 | H | H | $OCH_2CF_3$ | $OCH_3$ | CH | |
| Q-10 ($R_5$ = $CH_3$) | 0 | H | H | $CF_3$ | $OCH_3$ | CH | |
| Q-2 ($R_5$, $R_6$ = H) | 0 | H | H | $OCH_2CH_3$ | $OCH_3$ | N | |
| Q-1 ($R_5$, $R_6$ = H) | 0 | H | H | $OCH_2CH_2F$ | $CH_3$ | N | |
| Q-8 ($R_5'$ = $SCH_3$) | 0 | H | H | $OCH_2CF_3$ | $OCH_3$ | N | |
| Q-9 ($R_5$ = $CH_3$) | 0 | H | H | $OCH_3$ | H | CH | |
| Q-16 | 0 | H | H | $CH_3$ | $OC_2H_5$ | CH | |
| Q-8 ($R_5'$ = $SCH_3$) | 0 | H | H | $CH_3$ | $CH_2OCH_3$ | CH | |
| Q-8 ($R_5'$ = $CH_3$) | 0 | H | H | $OC_2H_5$ | $NHCH_3$ | N | |
| Q-17 ($R_5$ = H, $R_6$ = $CH_3$) | 0 | H | H | $OCH_3$ | $N(OCH_3)CH_3$ | N | |
| Q-8 ($R_5'$ = $SCH_3$) | 0 | H | H | $OCH_3$ | $N(CH_3)_2$ | N | |
| Q-18 ($R_5$ = H, $R_6$ = $CH_3$) | 0 | H | H | $OCH_3$ | $C_2H_5$ | CH | |
| Q-12 ($R_8$ = Cl) | 0 | H | H | $OCH_3$ | $CF_3$ | CH | |
| Q-11 ($R_5$ = $CH_3$) | 0 | H | H | $OCH_3$ | $SCH_3$ | CH | |
| Q-18 ($R_5$ = H, $R_6$ = $CH_3$) | 0 | H | H | $CH_3$ | $OCH_2CH=CH_2$ | N | |
| Q-10 ($R_5$ = H) | 0 | H | H | $CH_3$ | $OCH_2C\equiv CH$ | N | |
| Q-13 ($R_5$ = $CH_3$) | 0 | H | H | $OCH_3$ | $CH_2OCH_2CH_3$ | CH | |
| Q-17 ($R_5$ = H, $R_6$ = $CH_3$) | 0 | H | H | $CH_3$ | $OCH_2CH_2OCH_3$ | CH | |
| Q-14 | 0 | H | H | $CH_3$ | $CH_2SCH_3$ | CH | |
| Q-10 ($R_5$ = $CH_3$) | 0 | H | H | $CH_3$ | $\underset{CH}{\overset{O}{\|}}$ | CH | |
| Q-1 ($R_5$, $R_6$ = H) | 0 | H | H | $CH_3$ | $\underset{CCH_3}{\overset{O}{\|}}$ | CH | |
| Q-8 ($R_5'$ = $SCH_3$) | 0 | H | H | $OCH_3$ | $CH(OCH_3)_2$ | CH | |
| Q-1($R_5$, $R_6$ = H) | 0 | H | H | $CH_3$ | $CH(OCH_3)_2$ | N | |
| Q-8 ($R_5$ = $CH_3$) | 0 | H | H | $OCH_3$ | $CH(OC_2H_5)_2$ | CH | |
| Q-2 ($R_5$, $R_6$ = H) | 0 | H | H | $OCH_3$ | $CH(SCH_3)_2$ | CH | |
| Q-3 ($R_5$, $R_6$ = H) | 0 | H | H | $OCH_3$ | $C(CH_3)(OCH_3)_2$ | CH | |
| Q-8 ($R_5'$ = $SCH_3$) | 0 | H | H | $OCH_3$ | 1,3-dioxolan-2-yl | CH | |
| Q-18 | 0 | H | H | $CH_3$ | 1,3-dioxan-2-yl | CH | |

TABLE IIa-continued structure: R₁-pyridine with (CH₂)ₙQ substituent, SO₂NHCON(R)— linked to pyrimidine/triazine with X, Y, Z substituents

| Q | n | R | R₁ | X | Y | Z | m.p. °C. |
|---|---|---|----|---|---|---|----------|
| Q-17 | 0 | H | H | OCH₃ | (O-CH-S cyclic, CH₂CH₂) | CH | |
| Q-8 (R₅' = CH₃) | 0 | H | H | OCH₃ | (O-CH(CH₃)-O-CH₂ cyclic) | CH | |
| Q-10 (R₅ = H) | 0 | H | H | OCH₃ | OCF₂H | CH | |
| Q-14 | 0 | H | H | OCH₃ | SCF₂H | CH | |
| Q-8 (R₅' = SCH₃) | 0 | H | H | OCH₃ | (cyclopropyl CH-CH₂-CH₂) | N | |
| Q-1 (R₅, R₆ = H) | 0 | H | H | OCH₃ | (cyclopropyl CH-CH₂-CH₂) | CH | |
| C₆H₅ | 0 | H | H | OCH₃ | (cyclopropyl CH-CH₂-CH₂) | N | |
| C₆H₅ | 0 | H | H | OCH₃ | (cyclopropyl CH-CH₂-CH₂) | CH | |
| Q-1 (R₅, R₆ = H) | 1 | CH₃ | H | OCH₃ | OCH₃ | CH | |
| Q-1 (R₅, R₆ = H) | 1 | H | H | CH₃ | CH₃ | CH | |
| Q-1 (R₅, R₆ = H) | 1 | H | H | CH₃ | OCH₃ | CH | |
| Q-1 (R₅, R₆ = H) | 1 | H | H | OCH₃ | OCH₃ | CH | |
| Q-1 (R₅, R₆ = H) | 1 | H | H | Cl | OCH₃ | CH | |
| Q-1 (R₅ = H, R₆ = CH₃) | 1 | H | H | OCH₃ | OCH₃ | CH | |
| Q-1 (R₅ = CH₃, R₆ = H) | 1 | H | H | OCH₃ | OCH₃ | CH | |
| Q-2 (R₅, R₆ = H) | 1 | H | H | CH₃ | CH₃ | CH | |
| Q-2 (R₅, R₆ = H) | 1 | H | H | OCH₃ | OCH₃ | CH | |
| Q-2 (R₅, R₆ = H) | 1 | H | H | CH₃ | OCH₃ | CH | |
| Q-2 (R₅, R₆ = H) | 1 | H | H | Cl | OCH₃ | CH | |
| Q-2 (R₅ = CH₃, R₆ = H) | 1 | H | H | OCH₃ | OCH₃ | CH | |
| Q-2 (R₅ = H, R₆ = CH₃) | 1 | H | H | OCH₃ | OCH₃ | CH | |
| Q-3 (R₅, R₆ = H) | 1 | H | H | CH₃ | CH₃ | CH | |
| Q-3 (R₅, R₆ = H) | 1 | H | H | CH₃ | OCH₃ | CH | |
| Q-3 (R₅, R₆ = H) | 1 | H | H | OCH₃ | OCH₃ | CH | |
| Q-3 (R₅, R₆ = H) | 1 | H | H | Cl | OCH₃ | CH | |
| Q-3 (R₅ = CH₃; R₆ = H) | 1 | H | H | OCH₃ | OCH₃ | CH | |
| Q-4 (R₅, R₆ = H) | 1 | H | H | CH₃ | CH₃ | CH | |
| Q-4 (R₅, R₆ = H) | 1 | H | H | OCH₃ | CH₃ | CH | |
| Q-4 (R₅, R₆ = H) | 1 | H | H | OCH₃ | OCH₃ | CH | |
| Q-4 (R₅, R₆ = H) | 1 | H | H | Cl | OCH₃ | CH | |
| Q-5 (R₅, R₆ = H) | 1 | H | H | OCH₃ | OCH₃ | CH | |
| Q-5 (R₅, R₆ = H) | 1 | H | H | CH₃ | CH₃ | CH | |
| Q-5 (R₅, R₆ = H) | 1 | H | H | CH₃ | OCH₃ | CH | |
| Q-5 (R₅, R₆ = H) | 1 | H | H | Cl | OCH₃ | CH | |
| Q-6 (R₅ = H) | 1 | H | H | OCH₃ | OCH₃ | CH | |
| Q-6 (R₅ = H) | 1 | H | H | CH₃ | OCH₃ | CH | |
| Q-6 (R₅ = H) | 1 | H | H | CH₃ | CH₃ | CH | |
| Q-6 (R₅ = H) | 1 | H | H | Cl | OCH₃ | CH | |
| Q-8 (R₅' = H) | 1 | H | H | CH₃ | CH₃ | CH | |
| Q-8 (R₅' = H) | 1 | H | H | OCH₃ | OCH₃ | CH | |

TABLE IIa-continued

| Q | n | R | $R_1$ | X | Y | Z | m.p. °C. |
|---|---|---|---|---|---|---|---|
| Q-8 ($R_5' = H$) | 1 | H | H | $CH_3$ | $OCH_3$ | CH | |
| Q-8 ($R_5' = H$) | 1 | H | H | Cl | $OCH_3$ | CH | |
| Q-9 ($R_5 = H$) | 1 | H | H | $OCH_3$ | $OCH_3$ | CH | |
| Q-9 ($R_5 = H$) | 1 | H | H | $CH_3$ | $OCH_3$ | CH | |
| Q-10 ($R_5 = H$) | 1 | H | H | $OCH_3$ | $OCH_3$ | CH | |
| Q-10 ($R_5 = H$) | 1 | H | H | $CH_3$ | $OCH_3$ | CH | |
| Q-10 ($R_5 = H$) | 1 | H | H | Cl | $OCH_3$ | CH | |
| Q-11 ($R_5 = H$) | 1 | H | H | $OCH_3$ | $OCH_3$ | CH | |
| Q-11 ($R_5 = H$) | 1 | H | H | $CH_3$ | $OCH_3$ | CH | |
| Q-12 ($R_8 = H$) | 1 | H | H | $CH_3$ | $CH_3$ | CH | |
| Q-12 ($R_8 = H$) | 1 | H | H | Cl | $OCH_3$ | CH | |
| Q-13 ($R_5 = CH_3$) | 1 | H | H | $OCH_3$ | $OCH_3$ | CH | |
| Q-14 ($R_5 = H$) | 1 | H | H | $CH_3$ | $CH_3$ | CH | |
| Q-14 ($R_5 = H$) | 1 | H | H | $OCH_3$ | $OCH_3$ | CH | |
| Q-14 ($R_5 = H$) | 1 | H | H | $CH_3$ | $OCH_3$ | CH | |
| Q-14 ($R_5 = H$) | 1 | H | H | Cl | $OCH_3$ | CH | |
| Q-15 ($R_5 = H$) | 1 | H | H | $OCH_3$ | $OCH_3$ | CH | |
| Q-16 ($R_5, R_6 = H$) | 1 | H | H | $CH_3$ | $OCH_3$ | CH | |
| Q-16 ($R_5, R_6 = H$) | 1 | H | H | $CH_3$ | $CH_3$ | CH | |
| Q-16 ($R_5, R_6 = H$) | 1 | H | H | Cl | $OCH_3$ | CH | |
| Q-17 ($R_5, R_6 = H$) | 1 | H | H | $CH_3$ | $CH_3$ | CH | |
| Q-16 ($R_5, R_6 = H$) | 1 | H | H | $OCH_3$ | $OCH_3$ | CH | |
| Q-18 ($R_5, R_6 = H$) | 1 | H | H | $CH_3$ | $OCH_3$ | CH | |
| Q-18 ($R_5, R_6 = H$) | 1 | H | H | Cl | $OCH_3$ | CH | |
| Q-18 ($R_5, R_6 = H$) | 1 | H | H | $OCH_3$ | $OCH_3$ | CH | |
| Q-19 ($R_5 = CH_3, R_6 = H$) | 1 | H | H | $OCH_3$ | $OCH_3$ | CH | |
| Q-20 ($R_5, R_6 = CH_3$) | 1 | H | H | $OCH_3$ | $OCH_3$ | CH | |
| Q-22 ($R_5, R_6, R_7 = H$) | 1 | H | H | $OCH_3$ | $OCH_3$ | CH | |
| Q-24 ($R_5, R_6, R_7 = H$) | 1 | H | H | $OCH_3$ | $CH_3$ | CH | |
| Q-28 ($R_5, R_6 = H, n' = 1$) | 1 | H | H | $OCH_3$ | $OCH_3$ | CH | |
| Q-30 ($R_5 = H, R_9, R_{10} = CH_3$) | 1 | H | H | $OCH_3$ | $OCH_3$ | CH | |
| Q-33 ($R_5, R_6 = H$) | 1 | H | H | $OCH_3$ | $OCH_3$ | CH | |
| Q-35 ($R_{11}, R_{12} = OCH_3$) | 1 | H | H | $OCH_3$ | $OCH_3$ | CH | |
| $C_6H_5$ | 1 | H | H | $OCH_3$ | $OCH_3$ | CH | |
| $C_6H_5$ | 1 | H | H | $OCH_3$ | $CH_3$ | CH | |
| Q-37 ($R_5, R_6 = H$) | 1 | H | H | $OCH_3$ | $OCH_3$ | CH | |
| Q-38 ($R_5, R_6 = H$) | 1 | H | H | $OCH_3$ | $OCH_3$ | CH | |
| Q-39 ($R_5, R_6 = H$) | 1 | H | H | $OCH_3$ | $OCH_3$ | CH | |
| Q-1 ($R_5, R_6 = H$) | 1 | H | H | $OCH_3$ | $OCH_3$ | N | |
| Q-2 ($R_5, R_6 = H$) | 1 | H | H | $CH_3$ | $OCH_3$ | N | |
| Q-8 ($R_5' = CH_3$) | 1 | H | H | $CH_3$ | $OCH_3$ | N | |
| Q-8 ($R_5' = CH_3$) | 1 | H | H | $OCH_3$ | $OCH_3$ | N | |
| Q-12 ($R_8 = Cl$) | 1 | H | H | $OCH_3$ | $OCH_3$ | N | |
| Q-17 ($R_5, R_6 = H$) | 1 | H | H | $OCH_3$ | $OCH_3$ | N | |
| Q-18 ($R_5, R_6 = H$) | 1 | H | H | $OCH_3$ | $OCH_3$ | N | |
| Q-22 ($R_5, R_6, R_7 = H$) | 1 | H | H | $OCH_3$ | $CH_3$ | N | |
| Q-26 ($W' = O$) | 1 | H | H | $OCH_3$ | $OCH_3$ | N | |
| Q-27 ($R_5, R_6 = H$) | 1 | H | H | $OCH_3$ | $OCH_3$ | N | |
| Q-30 ($R_5, R_9, R_{10} = H$) | 1 | H | H | $OCH_3$ | $OCH_3$ | N | |
| Q-33 ($R_5, R_6 = H$) | 1 | H | H | $OCH_3$ | $OCH_3$ | N | |
| $C_6H_5$ | 1 | H | H | $CH_3$ | $OCH_3$ | N | |
| $C_6H_5$ | 1 | H | H | $OCH_3$ | $OCH_3$ | N | |
| Q-2 ($R_5, R_6 = H$) | 1 | H | 5-Cl | $OCH_3$ | $OCH_3$ | N | |
| Q-16 ($R_5, R_6 = H$) | 1 | H | 5-Br | $OCH_3$ | $OCH_3$ | CH | |
| Q-8 ($R_5' = SCH_3$) | 1 | H | 5-$CH_3$ | $OCH_3$ | $OCH_3$ | CH | |
| Q-8 ($R_5' = SCH_3$) | 1 | H | 5-Cl | $OCH_3$ | $OCH_3$ | N | |
| Q-1 ($R_5, R_6 = H$) | 1 | H | 5-$CH_3$ | $OCH_3$ | $CH_3$ | N | |
| Q-1 ($R_5, R_6 = H$) | 1 | $CH_3$ | H | $OCH_3$ | $CH_3$ | N | |
| Q-8 $R_5' = SCH_3$) | 1 | H | H | $OC_2H_5$ | $CH_3$ | CH | |
| Q-1 ($R_5, R_6 = H$) | 1 | H | H | F | $OCH_3$ | CH | |
| Q-2 ($R_5, R_6 = H$) | 1 | H | H | Br | $OCH_3$ | CH | |
| Q-3 ($R_5, R_6 = H$) | 1 | H | H | I | $OCH_3$ | CH | |
| Q-8 ($R_5'SCH_3$) | 1 | H | H | $OCF_2H$ | $OCH_3$ | CH | |
| Q-10 ($R_5 = CH_3$) | 1 | H | H | $CH_2F$ | $OCH_3$ | CH | |
| Q-18 ($R_5, R_6 = H$) | 1 | H | H | $OCH_2CH_2F$ | $CH_3$ | CH | |
| Q-17 ($R_5, R_6 = H$) | 1 | H | H | $OCH_2CHF_2$ | $CH_3$ | CH | |
| Q-8 ($R_5' = SCH_3$) | 1 | H | H | $OCH_2CF_3$ | $OCH_3$ | CH | |
| Q-10 ($R_5 = CH_3$) | 1 | H | H | $CF_3$ | $OCH_3$ | CH | |
| Q-2 ($R_5, R_6 = H$) | 1 | H | H | $OCH_2CH_3$ | $OCH_3$ | N | |
| Q-1 ($R_5, R_6 = H$) | 1 | H | H | $OCH_2CH_2F$ | $CH_3$ | N | |
| Q-8 ($R_5' = SCH_3$) | 1 | H | H | $OCH_2CF_3$ | $OCH_3$ | N | |

TABLE IIa-continued $$\underset{R_1}{\overset{(CH_2)_nQ}{\text{pyridine}}}-SO_2NHCON(R)-\underset{Y}{\overset{X}{\text{pyrimidine}}}Z$$

| Q | n | R | R$_1$ | X | Y | Z | m.p. °C. |
|---|---|---|---|---|---|---|---|
| Q-9 (R$_5$ = CH$_3$) | 1 | H | H | OCH$_3$ | H | CH | |
| Q-16 (R$_5$ = H, R$_6$ = CH$_3$) | 1 | H | H | CH$_3$ | OC$_2$H$_5$ | CH | |
| Q-8 (R$_5'$ = SCH$_3$) | 1 | H | H | CH$_3$ | CH$_2$OCH$_3$ | CH | |
| Q-8 (R$_5'$ = CH$_3$) | 1 | H | H | OC$_2$H$_5$ | NHCH$_3$ | N | |
| Q-17 (R$_5$ = H, R$_6$ = CH$_3$) | 1 | H | H | OCH$_3$ | N(OCH$_3$)CH$_3$ | N | |
| Q-8 (R$_5'$ = SCH$_3$) | 1 | H | H | OCH$_3$ | N(CH$_3$)$_2$ | N | |
| Q-18 (R$_5$ = H, R$_6$ = CH$_3$) | 1 | H | H | OCH$_3$ | C$_2$H$_5$ | CH | |
| Q-12 (R$_8$ = Cl) | 1 | H | H | OCH$_3$ | CF$_3$ | CH | |
| Q-11 (R$_5$ = CH$_3$) | 1 | H | H | OCH$_3$ | SCH$_3$ | N | |
| Q-18 (R$_5$ = H, R$_6$ = CH$_3$) | 1 | H | H | CH$_3$ | OCH$_2$CH=CH$_2$ | N | |
| Q-10 (R$_5$ = CH$_3$) | 1 | H | H | CH$_3$ | OCH$_2$C≡CH | N | |
| Q-13 (R$_5$ = CH$_3$) | 1 | H | H | OCH$_3$ | CH$_2$OCH$_2$CH$_3$ | CH | |
| Q-17 (R$_5$ = H, R$_6$ = CH$_3$) | 1 | H | H | CH$_3$ | OCH$_2$CH$_2$OCH$_3$ | CH | |
| Q-14 (R$_5$ = H) | 1 | H | H | CH$_3$ | CH$_2$SCH$_3$ | CH | |
| Q-1 (R$_5$, R$_6$-H) | 1 | H | H | OCH$_3$ | i-C$_3$H$_7$ | CH | |
| Q-10 (R$_5$ = CH$_3$) | 1 | H | H | CH$_3$ | CHO | CH | |
| Q-1 (R$_5$, R$_6$ = H) | 1 | H | H | CH$_3$ | COCH$_3$ | CH | |
| Q-8 R$_5'$ = SCH$_3$ | 1 | H | H | OCH$_3$ | CH(OCH$_3$)$_2$ | CH | |
| Q-1 (R$_5$, R$_6$ = H) | 1 | H | H | CH$_3$ | CH(OCH$_3$)$_2$ | N | |
| Q-8 (R$_5$ = SCH$_3$) | 1 | H | H | OCH$_3$ | CH(OC$_2$H$_5$)$_2$ | CH | |
| Q-2 (R$_5$, R$_6$ = H) | 1 | H | H | OCH$_3$ | CH(SCH$_3$)$_2$ | CH | |
| Q-3 (R$_5$, R$_6$ = H) | 1 | H | H | OCH$_3$ | C(CH$_3$)(OCH$_3$)$_2$ | CH | |
| Q-8 (R$_5'$SCH$_3$) | 1 | H | H | OCH$_3$ | CH(O-CH$_2$-CH$_2$-O) (1,3-dioxolane) | CH | |
| Q-18 (R$_5$ = R$_6$ = H) | 1 | H | H | CH$_3$ | CH(O-CH$_2$-CH$_2$-CH$_2$-O) (1,3-dioxane) | CH | |
| Q-17 (R$_5$ = R$_6$ = H) | 1 | H | H | OCH$_3$ | CH(O-CH$_2$-CH$_2$-S) (1,3-oxathiolane) | CH | |
| Q-8 (R$_5'$ = CH$_3$) | 1 | H | H | OCH$_3$ | CH(O-CH(CH$_3$)-CH$_2$-O) | CH | |
| Q-10 (R$_5$ = H) | 1 | H | H | OCH$_3$ | OCF$_2$H | CH | |
| Q-14 (R$_5$ = H) | 1 | H | H | OCH$_3$ | SCF$_2$H | CH | |
| Q-8 (R$_5'$ = SCH$_3$) | 1 | H | H | OCH$_3$ | CH(CH$_2$-CH$_2$-N) (aziridine) | N | |
| Q-1 (R$_5$, R$_6$ = H) | 1 | H | H | OCH$_3$ | CH(CH$_2$-CH$_2$) (cyclopropyl) | CH | |
| Q-1 (R$_5$, R$_6$ = H) | 1 | H | H | OCH$_3$ | CH(CH$_2$-CH$_2$) (cyclopropyl) | CH | |

TABLE IIa-continued

| Q | n | R | R₁ | X | Y | Z | m.p. °C. |
|---|---|---|----|---|---|---|----------|
| C₆H₅ | 1 | H | H | OCH₃ | CH₂–CH–CH₂ (cyclopropyl) | N | |
| C₆H₅ | 1 | H | H | OCH₃ | CH₂–CH–CH₂ (cyclopropyl) | CH | |
| Q-35 (R₁₁, R₁₂ = OCH₃) | 1 | H | H | OCH₃ | CH₂–CH–CH₂ (cyclopropyl) | CH | |
| Q-39 (R₅, R₆ = H) | 1 | H | H | OCH₃ | CH₂–CH–CH₂ (cyclopropyl) | CH | |
| Q-1 (R₅, R₆ = H) | 2 | H | H | OCH₃ | OCH₃ | CH | |
| Q-5 (R, R₆ = H) | 2 | H | H | OCH₃ | OCH₃ | CH | |
| Q-8 (R₅' = H) | 2 | H | H | OCH₃ | OCH₃ | CH | |
| Q-14 (R₅ = H) | 2 | H | H | OCH₃ | OCH₃ | CH | |
| Q-16 (R₅, R₆ = H) | 2 | H | H | OCH₃ | OCH₃ | CH | |
| Q-1 (R₅, R₆ = H) | 2 | H | H | OCH₃ | OCH₃ | N | |
| Q-10 (R₅ = H) | 2 | H | H | OCH₃ | OCH₃ | N | |
| Q-12 (R₈ = H) | 2 | H | H | CH₃ | OCH₃ | N | |
| Q-18 (R₅ = H, R₆ = CH₃) | 2 | H | H | OCH₃ | OCH₃ | N | |
| Q-24 (R₅, R₆, R₇ = H) | 2 | H | H | OCH₃ | OCH₃ | N | |
| Q-27 (R₅, R₆ = H) | 2 | H | H | OCH₃ | CH₃ | N | |
| Q-33 (R₅, R₆ = H) | 2 | H | H | OCH₃ | OCH₃ | N | |
| Q-37 (R₅, R₆ = H) | 2 | H | H | OCH₃ | OCH₃ | CH | |
| Q-1 (R₅, R₆ = H) | 2 | H | H | F | OCH₃ | CH | |
| Q-8 (R₅' = SCH₃) | 2 | H | H | OCF₂H | OCH₃ | CH | |
| Q-17 (R₅ = H, R₆ = CH₃) | 2 | H | H | OCH₂CH₂F | CH₃ | CH | |
| Q-2 (R₅, R₆ = H) | 2 | H | H | OCH₂CH₃ | OCH₃ | N | |
| Q-8 (R₅' = SCH₃) | 2 | H | H | OCH₂CF₃ | OCH₃ | N | |
| Q-8 (R₅' = CH₃) | 2 | H | H | OC₂H₅ | NHCH₃ | N | |
| Q-8 (R₅' = SCH₃) | 2 | H | H | OCH₃ | O–CH–O (dioxolane) | CH | |
| Q-18 (R₅ = H, R₆ = CH₃) | 2 | H | H | CH₃ | O–CH–O (dioxane) | CH | |
| Q-8 (R₅' = CH₃) | 2 | H | H | OCH₃ | CH₂–CH–CH₂ (cyclopropyl) | N | |
| Q-1 (R₅, R₆ = H) | 2 | H | H | OCH₃ | CH₂–CH–CH₂ (cyclopropyl) | CH | |

TABLE IIa-continued

Structure: Pyridine with R₁, (CH₂)ₙQ substituent, SO₂NHCON(R)- linked to pyrimidine with X, Y, Z substituents.

| Q | n | R | R₁ | X | Y | Z | m.p. °C. |
|---|---|---|---|---|---|---|---|
| C₆H₅ | 2 | H | H | OCH₃ | CH₂-CH-CH₂ (cyclopropyl) | CH | |
| C₆H₅ | 2 | H | H | OCH₃ | CH₂-CH-CH₂ (cyclopropyl) | CH | |
| Q-10 (R₅ = CH₃) | 0 | H | H | OCH₃ | OCH₃ | N | 185–188 |

TABLE IIb

Structure: Pyridine with R₁, (CH₂)ₙQ, SO₂NHCON(R)- linked to fused bicyclic pyrimidine with X₁, Y₁.

| Q | n | R | R₁ | X₁ | Y₁ | m.p. °C. |
|---|---|---|---|---|---|---|
| Q-1 (R₅, R₆ = H) | 0 | H | H | CH₃ | O | |
| Q-2 (R₅, R₆ = H) | 0 | H | H | CH₃ | O | |
| Q-3 (R₅, R₆ = H) | 0 | H | H | CH₃ | O | |
| Q-4 (R₅, R₆ = H) | 0 | H | H | CH₃ | O | |
| Q-7 (R₅, R₆, R₇ = H) | 0 | H | H | CH₃ | O | |
| Q-8 (R₅' = SCH₃) | 0 | H | H | CH₃ | O | |
| Q-8 (R₅' = CH₃) | 0 | H | H | CH₃ | O | |
| Q-8 (R₅' = H) | 0 | H | H | CH₃ | O | |
| Q-9 (R₅ = CH₃) | 0 | H | H | CH₃ | O | |
| Q-10 (R₅ = CH₃) | 0 | H | H | CH₃ | O | |
| Q-14 (R₅ = H) | 0 | H | H | CH₃ | O | |
| Q-16 (R₅, R₆ = H) | 0 | H | H | CH₃ | O | |
| Q-17 (R₅, R₆ = H) | 0 | H | H | CH₃ | O | |
| Q-18 (R₅, R₆ = H) | 0 | H | H | CH₃ | O | |
| Q-21 (R₅, R₆, R₇ = H) | 0 | H | H | CH₃ | O | |
| Q-22 (R₅, R₆, R₇ = H) | 0 | H | H | CH₃ | O | |
| Q-24 (R₅, R₆, R₇ = H) | 0 | H | H | CH₃ | O | |
| Q-27 (R₅, R₆ = H, n' = 0) | 0 | H | H | CH₃ | O | |
| Q-30 (R₅, R₉, R₁₀ = H) | 0 | H | H | CH₃ | O | |
| Q-33 (R₅, R₆ = H) | 0 | H | H | CH₃ | O | |
| Q-8 (R₅' = SCH₃) | 0 | H | H | OCH₃ | O | |
| Q-1 (R₅, R₆ = H) | 0 | H | H | OC₂H₅ | O | |
| Q-9 (R₅ = CH₃) | 0 | H | H | OCF₂H | O | |
| Q-8 (R₅' = CH₃) | 0 | H | H | CH₃ | CH₂ | |
| Q-8 (R₅' = SCH₃) | 0 | H | H | OCH₃ | CH₂ | |
| Q-1 (R₅, R₆ = H) | 1 | H | H | CH₃ | O | |
| Q-2 (R₅, R₆ = H) | 1 | H | H | CH₃ | O | |
| Q-8 (R₅' = SCH₃) | 1 | H | H | CH₃ | O | |
| Q-8 (R₅' = CH₃) | 1 | H | H | CH₃ | O | |
| Q-14 (R₅ = H) | 1 | H | H | CH₃ | O | |
| Q-16 (R₅, R₆ = H) | 1 | H | H | CH₃ | O | |
| Q-17 (R₅, R₆ = H) | 1 | H | H | CH₃ | O | |
| Q-18 (R₅, R₆ = H) | 1 | H | H | CH₃ | O | |
| Q-33 (R₅, R₆ = H) | 1 | H | H | CH₃ | O | |
| Q-1 (R₅, R₆ = H) | 1 | H | H | OC₂H₅ | O | |
| Q-8 (R₅' = CH₃) | 1 | H | H | OCF₂H | O | |
| Q-8 (R₅' = SCH₃) | 1 | H | H | OCH₃ | CH₂ | |
| Q-8 (R₅' = CH₃) | 2 | H | H | CH₃ | O | |
| Q-14 (R₅ = H) | 2 | H | H | CH₃ | O | |
| Q-8 (R₅' = SCH₃) | 2 | H | H | OC₂H₅ | O | |

TABLE IIb-continued

| Q | n | R | R₁ | X₁ | Y₁ | m.p. °C. |
|---|---|---|---|---|---|---|
| Q-33 (R₅, R₆ = H) | 2 | H | H | CH₃ | O | |

TABLE IIc

Structure: Pyridine with R₁, (CH₂)ₙQ, SO₂NHCON(R)- linked to pyrimidine fused with oxygen-containing ring, X₁ substituent.

| Q | n | R | R₁ | X₁ | m.p. °C. |
|---|---|---|---|---|---|
| Q-1 (R₅, R₆ = H) | 0 | H | H | CH₃ | |
| Q-2 (R₅, R₆ = H) | 0 | H | H | OCH₃ | |
| Q-3 (R₅, R₆ = H) | 0 | H | H | OC₂H₅ | |
| Q-4 (R₅, R₆ = H) | 0 | H | H | CH₃ | |
| Q-7 (R₅, R₆, R₇ = H) | 0 | H | H | CH₃ | |
| Q-8 (R₅' = SCH₃) | 0 | H | H | OCH₃ | |
| Q-8 (R₅' = CH₃) | 0 | H | H | OCH₃ | |
| Q-8 (R₅' = H) | 0 | H | H | CH₃ | |
| Q-9 (R₅ = CH₃) | 0 | H | H | OCF₂H | |
| Q-10 (R₅ = CH₃) | 0 | H | H | CH₃ | |
| Q-14 (R₅ = H) | 0 | H | H | OCH₃ | |
| Q-16 (R₅ = H, R₆ = CH₃) | 0 | H | H | CH₃ | |
| Q-17 (R₅ = H, R₆ = CH₃) | 0 | H | H | OCF₂H | |
| Q-18 (R₅ = H, R₆ = CH₃) | 0 | H | H | OCH₃ | |
| Q-21 (R₅, R₆, R₇ = H) | 0 | H | H | OCH₃ | |
| Q-22 (R₅, R₆, R₇ = H) | 0 | H | H | CH₃ | |
| Q-24 (R₅, R₆, R₇ = H) | 0 | H | H | CH₃ | |
| Q-27 (R₅, R₆ = H, n' = 0) | 0 | H | H | OCH₃ | |
| Q-30 (R₅, R₆, R₁₀ = H) | 0 | H | H | OCH₃ | |
| Q-33 (R₅, R₆ = H) | 0 | H | H | OCH₃ | |
| Q-1 (R₅, R₆ = H) | 1 | H | H | CH₃ | |
| Q-2 (R₅, R₆ = H) | 1 | H | H | OCH₃ | |
| Q-8 (R₅' = CH₃) | 1 | H | H | OCH₃ | |
| Q-8 (R₅' = SCH₃) | 1 | H | H | CH₃ | |
| Q-10 (R₅ = CH₃) | 1 | H | H | OC₂H₅ | |

TABLE IIc-continued

| Q | n | R | R₁ | X₁ | m.p. °C. |
|---|---|---|---|---|---|
| Q-14 ($R_5$ = H) | 1 | H | H | OCH₃ | |
| Q-17 ($R_5$ = H, $R_6$ = CH₃) | 1 | H | H | OCF₂H | |
| Q-21 ($R_5$ = H, $R_6$ = CH₃) | 1 | H | H | OCH₃ | |
| Q-33 ($R_5$, $R_6$ = H) | 1 | H | H | OCH₃ | |
| Q-8 ($R_5'$ = CH₃) | 2 | H | H | CH₃ | |
| Q-27 (R, $R_6$ = H, n' = 0) | 2 | H | H | OCH₃ | |
| Q-28 ($R_5$, $R_6$ = H, n' = 1) | 2 | H | H | OCH₃ | |
| Q-1 ($R_5$, $R_6$ = H) | 2 | H | H | CH₃ | |
| Q-4 ($R_5$, $R_6$ = H) | 2 | H | H | OC₂H₅ | |

TABLE IId

| Q | n | R | R₁ | X₁ | Y₂ | m.p. °C. |
|---|---|---|---|---|---|---|
| Q-1 ($R_5$, $R_6$ = H) | 0 | H | H | CH₃ | CH₃ | |
| Q-2 ($R_5$, $R_6$ = H) | 0 | H | H | OCH₃ | CH₃ | |
| Q-3 ($R_5$, $R_6$ = H) | 0 | H | H | OC₂H₅ | H | |
| Q-4 ($R_5$, $R_6$ = H) | 0 | H | H | CH₃ | CH₃ | |
| Q-7 ($R_5$, $R_6$, $R_7$ = H) | 0 | H | H | CH₃ | CH₃ | |
| Q-8 ($R_5'$ = SCH₃) | 0 | H | H | CH₃ | CH₃ | |
| Q-8 ($R_5'$ = CH₃) | 0 | H | H | CH₃ | CH₃ | |
| Q-8 ($R_5'$ = H) | 0 | H | H | CH₃ | CH₃ | |
| Q-9 ($R_5$ = CH₃) | 0 | H | H | OCF₂H | CH₃ | |
| Q-10 ($R_5$ = CH₃) | 0 | H | H | CH₃ | CH₃ | |
| Q-14 ($R_5$ = H) | 0 | H | H | CH₃ | CH₃ | |
| Q-16 ($R_5$, $R_6$ = H) | 0 | H | H | CH₃ | CH₃ | |
| Q-17 ($R_5$, $R_6$ = H) | 0 | H | H | OCF₂H | CH₃ | |
| Q-18 ($R_5$, $R_6$ = H) | 0 | H | H | OC₂H₅ | CH₃ | |
| Q-21 ($R_5$, $R_6$, $R_7$ = H) | 0 | H | H | CH₃ | CH₃ | |
| Q-22 ($R_5$, $R_6$, $R_7$ = H) | 0 | H | H | OCH₃ | H | |
| Q-24 ($R_5$, $R_6$, $R_7$ = H) | 0 | H | H | OCF₂H | CH₃ | |
| Q-27 ($R_5$, $R_6$ = H, n' = 0) | 0 | H | H | CH₃ | CH₃ | |
| Q-30 ($R_5$, $R_9$, $R_{10}$ = H) | 0 | H | H | CH₃ | CH₃ | |
| Q-33 ($R_5$, $R_6$ = H) | 0 | H | H | CH₃ | CH₃ | |
| Q-1 ($R_5$, $R_6$ = H) | 1 | H | H | CH₃ | CH₃ | |
| Q-2 ($R_5$, $R_6$ = H) | 1 | H | H | OCH₃ | CH₃ | |
| Q-3 ($R_5$, $R_6$ = H) | 1 | H | H | OC₂H₅ | H | |
| Q-8 ($R_5'$ = SCH₃) | 1 | H | H | CH₃ | CH₃ | |
| Q-8 ($R_5'$ = CH₃) | 1 | H | H | CH₃ | CH₃ | |
| Q-14 ($R_5$ = H) | 1 | H | H | CH₃ | CH₃ | |
| Q-16 ($R_5$ = H, $R_6$ = CH₃) | 1 | H | H | CH₃ | CH₃ | |
| Q-18 ($R_5$ = H, $R_6$ = CH₃) | 1 | H | H | OC₂H₅ | CH₃ | |
| Q-21 ($R_5$, $R_6$, $R_7$ = H) | 1 | H | H | CH₃ | CH₃ | |
| Q-27 ($R_5$, $R_6$ = H, n' = 0) | 1 | H | H | CH₃ | CH₃ | |
| Q-33 ($R_5$, $R_6$ = H) | 1 | H | H | CH₃ | CH₃ | |
| Q-38 ($R_5$, $R_6$ = H) | 1 | H | H | CH₃ | CH₃ | |
| Q-1 ($R_5$, $R_6$ = H) | 2 | H | H | CH₃ | CH₃ | |
| Q-8 ($R_5'$ = SCH₃) | 2 | H | H | CH₃ | CH₃ | |
| Q-8 ($R_5'$ = CH₃) | 2 | H | H | CH₃ | CH₃ | |
| Q-14 ($R_5$ = H) | 2 | H | H | OCH₃ | CH₃ | |
| Q-33 ($R_5$, $R_6$ = H) | 2 | H | H | CH₃ | CH₃ | |

TABLE IIe

| Q | n | R | R₁ | X₂ | Y₃ | m.p. °C. |
|---|---|---|---|---|---|---|
| Q-1 ($R_5$, $R_6$ = H) | 0 | H | H | CH₃ | CH₃ | |
| Q-2 ($R_5$, $R_6$ = H) | 0 | H | H | OCH₃ | CH₃ | |
| Q-3 ($R_5$, $R_6$ = H) | 0 | H | H | OCH₃ | C₂H₅ | |
| Q-4 ($R_5$, $R_6$ = H) | 0 | H | H | CH₃ | CH₃ | |
| Q-7 ($R_5$, $R_6$, $R_7$ = H) | 0 | H | H | CH₃ | CH₃ | |
| Q-8 ($R_5'$ = SCH₃) | 0 | H | H | CH₃ | CH₂CF₃ | |
| Q-8 ($R_5'$ = CH₃) | 0 | H | H | CH₃ | CH₂CF₃ | |
| Q-8 ($R_5'$ = H) | 0 | H | H | CH₃ | CH₃ | |
| Q-9 ($R_5$ = CH₃) | 0 | H | H | OCH₃ | CH₃ | |
| Q-10 ($R_5$ = CH₃) | 0 | H | H | CH₃ | CH₃ | |
| Q-14 ($R_5$ = H) | 0 | H | H | CH₃ | C₂H₅ | |
| Q-16 ($R_5$ = H, $R_6$ = CH₃) | 0 | H | H | CH₃ | CH₃ | |
| Q-17 ($R_5$ = H, $R_6$ = CH₃) | 0 | H | H | OCH₃ | CH₂CF₃ | |
| Q-18 ($R_5$ = H, $R_6$ = CH₃) | 0 | H | H | OCH₃ | CH₃ | |
| Q-21 ($R_5$, $R_6$, $R_7$ = H) | 0 | H | H | CH₃ | CH₃ | |
| Q-22 ($R_5$, $R_6$, $R_7$ = H) | 0 | H | H | OCH₃ | C₂H₅ | |
| Q-24 ($R_5$, $R_6$, $R_7$ = H) | 0 | H | H | OCH₃ | CH₃ | |
| Q-27 ($R_5$, $R_6$ = H, n' = 0) | 0 | H | H | CH₃ | CH₃ | |
| Q-30 ($R_5$, $R_9$, $R_{10}$ = H) | 0 | H | H | CH₃ | CH₃ | |
| Q-33 ($R_5$, $R_6$ = H) | 0 | H | H | CH₃ | CH₃ | |
| Q-1 ($R_5$, $R_6$ = H) | 1 | H | H | CH₃ | CH₃ | |
| Q-2 ($R_5$, $R_6$ = H) | 1 | H | H | OCH₃ | CH₃ | |
| Q-8 ($R_5'$ = CH₃) | 1 | H | H | CH₃ | C₂H₅ | |
| Q-8 ($R_5'$ = SCH₃) | 1 | H | H | CH₃ | CH₂CF₃ | |
| Q-9 ($R_5$ = CH₃) | 1 | H | H | OCH₃ | CH₃ | |
| Q-10 ($R_5$ = CH₃) | 1 | H | H | CH₃ | CH₃ | |
| Q-14 ($R_5$ = H) | 1 | H | H | CH₃ | C₂H₅ | |
| Q-16 ($R_5$ = H, $R_6$ = CH₃) | 1 | H | H | CH₃ | CH₃ | |
| Q-27 ($R_5$, $R_6$ = H) | 1 | H | H | CH₃ | CH₃ | |
| Q-33 ($R_5$, $R_6$ = H) | 1 | H | H | CH₃ | CH₃ | |
| Q-1 ($R_5$, $R_6$ = H) | 2 | H | H | CH₃ | CH₃ | |
| Q-8 ($R_5'$ = CH₃) | 2 | H | H | OCH₃ | CH₃ | |
| Q-14 ($R_5$ = H) | 2 | H | H | CH₃ | CH₃ | |
| Q-18 ($R_5$ = H, $R_6$ = CH₃) | 2 | H | H | OCH₃ | CH₂CF₃ | |

TABLE IIf

| Q | n | R | R₁ | X₃ | m.p. °C. |
|---|---|---|---|---|---|
| Q-1 ($R_5$, $R_6$ = H) | 0 | H | H | CH₃ | |
| Q-2 ($R_5$, $R_6$ = H) | 0 | H | H | CH₃ | |
| Q-3 ($R_5$, $R_6$ = H) | 0 | H | H | CH₃ | |
| Q-4 ($R_5$, $R_6$ = H) | 0 | H | H | OCH₃ | |
| Q-7 ($R_5$, $R_6$, $R_7$ = H) | 0 | H | H | OCH₃ | |
| Q-8 ($R_5'$ = CH₃) | 0 | H | H | CH₃ | |
| Q-8 ($R_5'$ = SCH₃) | 0 | H | H | OCH₃ | |
| Q-8 ($R_5'$ = H) | 0 | H | H | CH₃ | |
| Q-9 ($R_5$ = CH₃) | 0 | H | H | CH₃ | |
| Q-10 ($R_5$ = CH₃) | 0 | H | H | OCH₃ | |
| Q-14 ($R_5$ = H) | 0 | H | H | OCH₃ | |
| Q-16 ($R_5$ = H, $R_6$ = CH₃) | 0 | H | H | CH₃ | |
| Q-17 ($R_5$ = H, $R_6$ = CH₃) | 0 | H | H | CH₃ | |
| Q-18 ($R_5$ = H, $R_6$ = CH₃) | 0 | H | H | OCH₃ | |
| Q-21 ($R_5$, $R_6$, $R_7$ = H) | 0 | H | H | CH₃ | |
| Q-22 ($R_5$, $R_6$, $R_7$ = H) | 0 | H | H | OCH₃ | |
| Q-24 ($R_5$, $R_6$, $R_7$ = H) | 0 | H | H | CH₃ | |
| Q-27 ($R_5$, $R_6$ = H) | 0 | H | H | CH₃ | |
| Q-30 ($R_5$, $R_9$, $R_{10}$ = H) | 0 | H | H | OCH₃ | |
| Q-33 ($R_5$, $R_6$ = H) | 0 | H | H | CH₃ | |
| Q-38 ($R_5$, $R_6$ = H) | 0 | H | H | CH₃ | |
| Q-1 ($R_5$, $R_6$ = H) | 1 | H | H | OCH₃ | |
| Q-2 ($R_5$, $R_6$ = H) | 1 | H | H | CH₃ | |

TABLE IIf-continued $$R_1 \underset{N}{\overset{(CH_2)_nQ}{\bigcirc}} SO_2NHCON(R)-CH_2-\underset{N}{\overset{OCH_3}{\bigcirc}}-X_3$$

| Q | n | R | R₁ | X₃ | m.p. °C. |
|---|---|---|---|---|---|
| Q-8(R₅' = CH₃) | 1 | H | H | CH₃ | |
| Q-8(R₅' = SCH₃) | 1 | H | H | OCH₃ | |
| Q-10(R₅ = CH₃) | 1 | H | H | CH₃ | |
| Q-14(R₅ = H) | 1 | H | H | CH₃ | |
| Q-16(R₅ = H, R₆ = CH₃) | 1 | H | H | OCH₃ | |
| Q-18(R₅ = H, R₆ = CH₃) | 1 | H | H | OCH₃ | |
| Q-27(R₅, R₆ = H, n' = 0) | 1 | H | H | CH₃ | |
| Q-38(R₅, R₆ = H) | 1 | H | H | OCH₃ | |
| Q-1(R₅, R₆ = H) | 2 | H | H | OCH₃ | |
| Q-8(R₅' = CH₃) | 2 | H | H | OCH₃ | |

TABLE IIq $$R_1 \underset{N}{\overset{(CH_2)_nQ}{\bigcirc}} SO_2NHCSN(R)-\underset{N}{\overset{X}{\bigcirc}}\overset{Z}{\underset{Y}{}}$$

| Q | n | R | R₁ | X | Y | Z | m.p. °C. |
|---|---|---|---|---|---|---|---|
| Q-1(R₅, R₆ = H) | 0 | H | H | OCH₃ | OCH₃ | CH | |
| Q-1(R₅, R₆ = H) | 1 | H | H | OCH₃ | OCH₃ | CH | |
| Q-2(R₅, R₆ = H) | 0 | H | H | OCH₃ | CH₃ | CH | |
| Q-3(R₅, R₆ = H) | 0 | H | H | OCH₃ | OCH₃ | CH | |
| Q-4(R₅, R₆ = H) | 0 | H | H | OCH₃ | OCH₃ | CH | |
| Q-1(R₅, R₆ = H) | 0 | H | H | CH₃ | OCH₃ | N | |
| Q-8(R₅' = CH₃) | 0 | H | H | OCH₃ | CH₃ | CH | |
| Q-9(R₅ = CH₃) | 0 | H | H | OCH₃ | OCH₃ | CH | |
| Q-10(R₅ = CH₃) | 0 | H | H | CH₃ | OCH₃ | CH | |
| Q-14(R₅ = H) | 0 | H | H | OCH₃ | OCH₃ | CH | |
| Q-16(R₅, R₆ = H) | 0 | H | H | OCH₃ | OCH₃ | CH | |
| Q-17(R₅ = H, R₆ = CH₃) | 0 | H | H | OCH₃ | OCH₃ | CH | |
| Q-21(R₅, R₆, R₇ = H) | 0 | H | H | OCH₃ | OCH₃ | CH | |
| Q-22(R₅, R₆, R₇ = H) | 0 | H | H | OCH₃ | OCH₃ | CH | |
| Q-24(R₅, R₆, R₇ = H) | 0 | H | H | OCH₃ | OCH₃ | CH | |
| Q-33(R₅, R₆ = H) | 0 | H | H | OCH₃ | OCH₃ | CH | |
| Q-8(R₅' = CH₃) | 1 | H | H | OCH₃ | OCH₃ | CH | |
| Q-8(R₅' = CH₃) | 1 | H | H | OCH₃ | CH₃ | N | |
| Q-8(R₅' = CH₃) | 0 | H | H | CH₃ | OCH₃ | N | |
| Q-8(R₅' = CH₃) | 2 | H | H | OCH₃ | OCH₃ | CH | |

Formulations

Useful formulations of the compounds of Formulae I and II can be prepared in conventional ways. They include dusts, granules, pellets, solutions, suspensions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20-90 | 0-74 | 1-10 |
| Oil Suspensions and Solutions (including Emulsifiable Concentrates) | 1-50 | 40-99 | 0-15 |
| Aqueous Suspension | 5-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers", 2nd. Ed., Dorland Books, Caldwell, NJ. The more absorptive diluents are preferred for wettable powders and the denser ones for dusts. Typical liquid diluents and solvents are described in Marsden, "Solvents Guide", 2nd. Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, NJ, as well as Sisely and Wood, "Encyclopedia of Surface Active Agents", Chemical Publ. Co., Inc., New York, 1964, list surfactants and recommended uses. All formulations can contain minor amounts of additives to reduce foam, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. (see J. E. Browning, "Agglomeration", *Chemical Engineering*, Dec. 4, 1967, pp 147ff. and "Perry's Chemical Engineer's Handbook", 4th Ed., McGraw-Hill, NY, 1963, pp 8-59ff.)

EXAMPLE 6

Wettable Powder

| | |
|---|---|
| N—[(4,6-dimethoxypyrimidin-2-yl)aminocarbonyl]-2-(1H—1,2,4-triazol-1-yl)-3-pyridinesulfonamide | 80% |
| sodium alkylnaphthalenesulfonate | 2% |
| sodium ligninsulfonate | 2% |
| synthetic amorphous silica | 3% |
| kaolinite | 13% |

The ingredients are thoroughly blended and hammer-milled or air-milled to produce particles averaging below 20 microns in diameter. The product is reblended before packaging.

EXAMPLE 7

Oil suspension

| | |
|---|---|
| N—[(4,6-dimethoxypyrimidin-2-yl)aminocarbonyl]-2-(1H—1,2,4-triazol-1-yl)-3-pyridinesulfonamide | 35% |
| blend of polyalcohol carboxylic esters and oil soluble petroleum sulfonates | 6% |
| Xylene | 59% |

The ingredients are combined and ground together in a sand mill to produce particles essentially all below 3 microns. The product can be used directly, extended with oils, or emulsified in water.

EXAMPLE 8

Oil Suspension

| | |
|---|---|
| N—[(4,6-dimethoxypyrimidin-2-yl)aminocarbonyl]-2-(1H—1,2,4-triazol-1-yl)-3-pyridinesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

Solution

| | |
|---|---|
| N—[(4,6-dimethoxypyrimidin-2-yl)aminocarbonyl]-2-(1H—1,2,4-triazol-1-yl)-3-pyridinesulfonamide | 5% |
| dimethylformamide | 95% |

The ingredients are combined and stirred to produce a solution which can be used for low volume applications.

EXAMPLE 10

Emulsifiable Concentrate

| | |
|---|---|
| N—[(4,6-dimethoxypyrimidin-2-yl)aminocarbonyl]-2-(1H—1,2,4-triazol-1-yl)-3-pyridinesulfonamide | 5.0% |
| blend of oil soluble sulfonates and polyoxyethylene ethers | 4.0% |
| N—methyl pyrrolidone | 45.5% |
| xylene | 45.5% |

The active ingredients are combined and stirred until dissolved. A fine screen filter is included in packaging operation to insure the absence of any extraneous undissolved material in the product.

EXAMPLE 11

Aqueous Suspension

| | |
|---|---|
| N—[(4,6-dimethoxypyrimidin-2-yl)aminocarbonyl]-2-(1H—1,2,4-triazol-1-yl)-3-pyridinesulfonamide | 50.0% |
| dodecylphenol polyethylene glycol ether | 0.5% |
| crude calcium ligninsulfonate | 5.0% |
| xanthan gum thickener | 0.2% |
| paraformaldehyde | 0.2% |
| water | 44.1% |

The ingredients are ground together in a sand ball or roller mill to produce particles essentially all under five microns in size.

EXAMPLE 12

Dust

| | |
|---|---|
| N—[(4,6-dimethoxypyrimidin-2-yl)aminocarbonyl]-2-(1H—1,2,4-triazol-1-yl)-3-pyridinesulfonamide (active ingredient) | 20% |
| attapulgite | 10% |
| talc | 70% |

The ingredient is blended with attapulgite and then passed through a hammer-mill to produce particles substantially all below 200 microns. The ground concentrate is then blended with powdered talc until homogeneous.

EXAMPLE 13

Dust

| | |
|---|---|
| wettable powder of Example 6 | 5% |
| pyrophyllite (powder) | 95% |

The wettable powder and the pyrophyllite diluent are thoroughly blended and then packaged. The product is suitable for use as a dust.

EXAMPLE 14

Granule

| | |
|---|---|
| wettable powder of Example 6 | 84% |
| sugar | 16% |

The ingredients are blended in a rotating or fluid bed mixer and water sprayed on to accomplish granulation. When most of the material has reached the desired range of 1.0 to 0.52 mm. (U.S.S. #18 to 40 sieves), the granules are removed, dried, and screened. Oversize material is crushed to produce additional material in the desired range.

EXAMPLE 15

Granule

| | |
|---|---|
| wettable powder of Example 6 | 10% |
| attapulgite granules (U.S.S. #20–40; 0.84–0.42 mm) | 90% |

A slurry of wettable powder containing 50% solids is sprayed on the surface of attapulgite granules in a double-cone blender. The granules are dried and pckaged.

EXAMPLE 16

Extruded Pellet

| | |
|---|---|
| N—[(4,6-dimethoxypyrimidin-2-yl)aminocarbonyl]-2-(1H—1,2,4-triazol-1-yl)-3-pyridinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with water. The mixture is extruded as cylinders about 3 mm diameter which are cut to produce pellets about 3 mm long. These may be used directly after drying, or the dried pellets may be crushed to pass a U.S.S. #20 sieve (0.84 mm openings). The granules held on a U.S.S. #40 sieve (0.42 mm openings) may be packaged for use and the fines recycled.

EXAMPLE 17

High Strength Concentrate

| | |
|---|---|
| N—[(4,6-dimethoxypyrimidin-2-yl)aminocarbonyl]-]-(1H—1,2,4-triazol-1-yl)-3-pyridinesulfonamide | 98.5% |
| silica aerogel | 0.5% |
| synthetic amorphous fine silica | 1.0% |

The ingredients are blended and ground in a hammer-mill to produce a high strength concentrate essentially all passing a U.S.S. #50 sieve (0.3 mm openings). This material may then be formulated in a variety of ways.

Utility

Test results indicate that the compounds of the present invention are highly active preemergent or postemergent herbicides or plant growth regulators. Many of them have utility for broad-spectrum and pre- and or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, wheat, barley and corn. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commerical herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds

Compound 1

Compound 2

Compound 3

TEST A

Seeds of crabgrass (Digitaria spp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, cotton, rice, wheat, and purple nutsedge (Cyperus rotundus) tubers were planted and treated preemergence with the test chemicals dissolved in a non-phytotoxic solvent. At the same time, these crop and weed species were treated with a soil/foilage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| | Compound 1 | | Compound 2 | | Compound 3 | |
|---|---|---|---|---|---|---|
| Rate g/ha | 2000 | 400 | 2000 | 400 | 2000 | 400 |
| POSTEMERGENCE | | | | | | |
| Cotton | 5C,9G | 4C,9G | 4C,9G | 3C,9H | 3C,9H | 3C,5H |
| Sorghum | 3C,8H | 2C,2G | 3C,6G | 3C | 0 | 0 |
| Corn | 3C,8H | 0 | 2C,6H | 0 | 0 | 0 |
| Soybean | 3C,8H | 3C,8G | 3C,8G | 2C,8G | 0 | 0 |
| Wheat | 5G | 0 | 5G | 2G | 0 | 0 |
| Wild Oats | 0 | 0 | 5G | 0 | 0 | 0 |
| Rice | 2C,8G | 3G | 4C,8G | 3C,5G | 3C,5G | 0 |
| Barnyardgrass | 3C,9H | 2G | 4C,8H | 0 | 0 | 0 |
| Morningglory | 3C,8H | 3C,8H | 3C,8H | 3C,7H | 0 | 0 |
| Cocklebur | 5C,9H | 4C,8H | 3C,9H | 4C,9H | 0 | 0 |
| Sicklepod | 4C,8H | 3C,7G | 3C,8H | 4C,5G | 0 | 0 |
| Nutsedge | 2C,9G | 2C,9G | 3C,9G | 3C,8G | 0 | 0 |
| Sugar beet | 9C | 5C,9G | 9C | 9H | 0 | 0 |
| PREEMERGENCE | | | | | | |

TABLE A-continued

| Rate g/ha | Compound 1 | | Compound 2 | | Compound 3 | |
|---|---|---|---|---|---|---|
| | 2000 | 400 | 2000 | 400 | 2000 | 400 |
| Cotton | 9G | 8G | 9G | 7G | 2G | 0 |
| Sorghum | 3C,9G | 3C,5G | 3C,8H | 2C,5G | 0 | 0 |
| Corn | 2C,9G | 3C,7H | 3C,9H | 3C,7G | 2G | 0 |
| Soybean | 3C,7G | 3C,6G | 4C,8H | 3C,6H | 2C | 0 |
| Wheat | 2G | 0 | 2C,7G | 3G | 0 | 0 |
| Wild Oats | 0 | 0 | 3C,8G | 0 | 0 | 0 |
| Rice | 9H | 5G | 4C,8H | 2C,5G | 2C | 0 |
| Barnyardgrass | 8H | 3C,6H | 3C,8H | 0 | 0 | 0 |
| Morningglory | 9G | 9G | 9G | 3C,8H | 2C | 0 |
| Cocklebur | 9H | 7H | — | 3C,8H | 0 | 0 |
| Sicklepod | 8G | 4C,8G | 4C,9G | 3C,5G | 2C | 0 |
| Nutsedge | 10E | 5G | 10E | 0 | 0 | 0 |
| Sugar beet | 4C,9G | 5C,9G | 5C,9G | 3C,9G | 5G | 0 |

What is claimed is:

1. A compound of the formula I or II

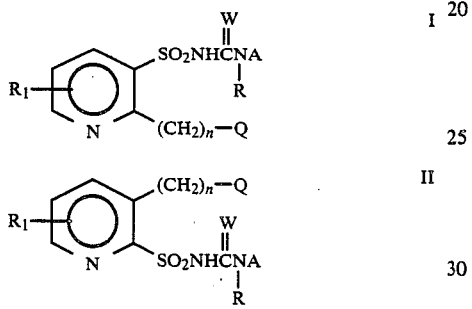

wherein
R is H or CH$_3$;
R$_1$ is H, Cl, Br, SCH$_3$ or CH$_3$;
n is 0, 1 or 2;
W is O or S;
Q is selected from the group consisting of

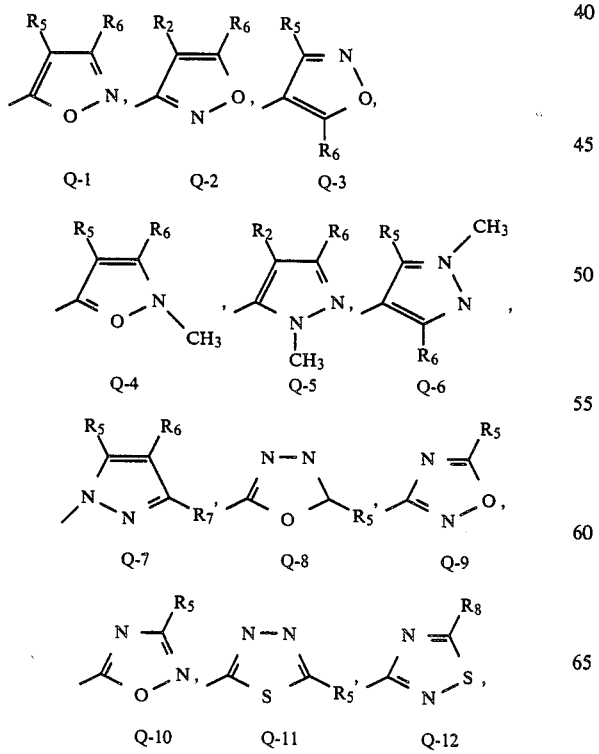

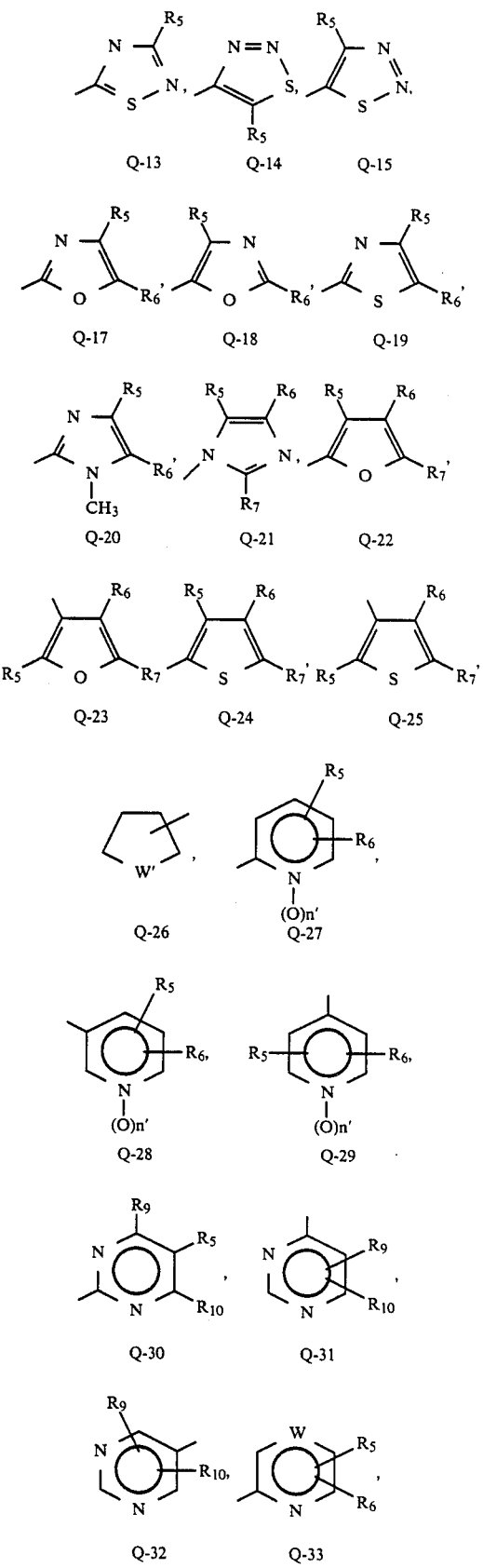

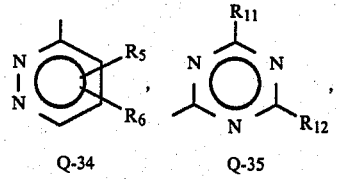

Q-34, Q-35

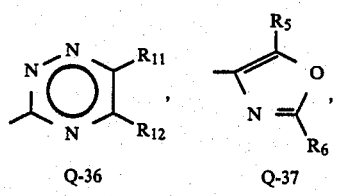

Q-36, Q-37

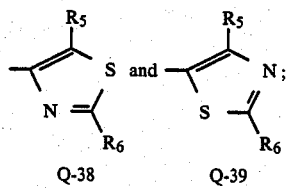

Q-38, Q-39 n' is 0 or 1;
$R_5$, $R_6$ and $R_7$ are independently H or $CH_3$;
$R_5'$ is H, $CH_3$, $C_2H_5$, $C_1$-$C_3$ alkylthio, $SCH_2CH=CH_2$, $SCF_2H$, $OCH_3$ or $OCH_2CH_3$;
$R_8$ is H or Cl;
$R_9$ and $R_{10}$ are independently H, $CH_3$ or $OCH_3$;
$R_{11}$ and $R_{12}$ are independently $CH_3$ or $OCH_3$;
W' is O, S or $NR_{13}$; and
$R_{13}$ is H, $C_1$-$C_3$ alkyl or $CH_2CH=CH_2$;
A is

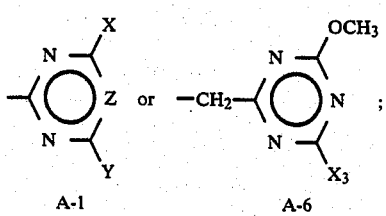

A-1, A-6

X is $CH_3$, $OCH_3$, $OCH_2CH_3$, $CH_2F$, $OCH_2CH_2F$, $OCH_2CHF_2$, $OCH_2CF_3$ or $CF_3$;
Y is H, $C_1$-$C_2$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv H$, $CH_2OCH_2CH_3$, $OCH_2CH_2OCH_3$, $CH_2SCH_3$,

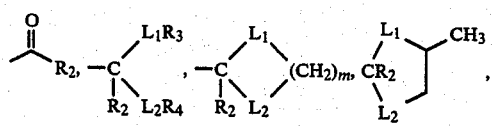

$SCF_2H$ or cyclopropyl;
m is 2 or 3;
$L_1$ and $L_2$ are independently O or S;
$R_2$ is H or $CH_3$;
$R_3$ and $R_4$ are independently $C_1$-$C_2$ alkyl;
Z is N; and
$X_3$ is $CH_3$ or $OCH_3$;
provided that
 when W is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

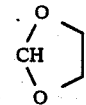

;

and their agriculturally suitable salts.

2. A compound of claim 1 selected from Formulae I or II wherein
R is H; and
W is O.

3. A compound of claim 2 wherein A is A-1; $R_1$ is H; n' is 0; and Q is selected from the group consisting of Q-1, Q-2, Q-3, Q-4, Q-7, Q-8, Q-9, Q-10, Q-11, Q-14, Q-17, Q-18, Q-21, Q-22, Q-24, Q-27, Q-30, Q-33, Q-37 and Q-38.

4. A compound of claim 3 wherein X is $CH_3$, $OCH_3$ or $OCH_2CH_3$ and Y is $CH_3$, $CH_2CH_3$, $OCH_3$, $CH(OCH_3)_2$ or $CH_2OCH_3$.

5. A compound of claim 4 where n is 0.

6. A compound of claim 5 where Y is $CH_3$, $CH_2CH_3$ or $OCH_3$.

7. A compound of claim 6 of Formula I.

8. A compound of claim 6 of Formula II.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 3 and at least one of the following: surfactant, solid or liquid diluent.

12. A composition suitable for controlling the growth of undesired vegetation which comprises an effective amount of a compound of claim 4 and at least one of the following: surfactant, solid or liquid diluent.

13. A composition suitable for controlling the growth of undesired vegetation which comprises an effective amount of a compound of claim 5 and at least one of the following: surfactant, solid or liquid diluent.

14. A composition suitable for controlling the growth of undesired vegetation which comprises an effective amount of a compound of claim 6 and at least one of the following: surfactant, solid or liquid diluent.

15. A composition suitable for controlling the growth of undesired vegetation which comprises an effective amount of a compound of claim 7 and at least one of the following: surfactant, solid or liquid diluent.

16. A composition suitable for controlling the growth of undesired vegetation which comprises an effective amount of a compound of claim 8 and at least one of the following: surfactant, solid or liquid diluent.

17. A method for controlling the growth of undesired vegetation which comprises applying to the locus to be protected, an effective amount of a compound of claim 1.

18. A method for controlling the growth of undesired vegetation which comprises applying the locus to be protected, an effective amount of a compound of claim 2.

19. A method for controlling the growth of undesired vegetation which comprises applying to the locus to be protected, an effective amount of a compound of claim 3.

20. A method for controlling the growth of undesired vegetation which comprises applying to the locus to be protected, an effective amount of a compound of claim 4.

21. A method for controlling the growth of undesired vegetation which comprises applying to the locus to be protected, an effective amount of a compound of claim 5.

22. A method for controlling the growth of undesired vegetation which comprises applying to the locus to be protected, an effective amount of a compound of claim 6.

23. A method for controlling the growth of undesired vegetation which comprises applying to the locus to be protected, an effective amount of a compound of claim 7.

24. A method for controlling the growth of undesired vegetation which comprises applying to the locus to be protected, an effective amount of a compound of claim 8.

* * * * *

UNITED STATES PATENT AND TRADEMARK OFFICE
CERTIFICATE OF CORRECTION

PATENT NO. : 4,784,684

DATED : November 15, 1988

INVENTOR(S) : Morris Padgett Rorer

It is certified that error appears in the above-identified patent and that said Letters Patent is hereby corrected as shown below:

col. 65, line 50: "OCH$_2$C≡H" should be --OCH$_2$C≡CH-- col. 63, line 40: 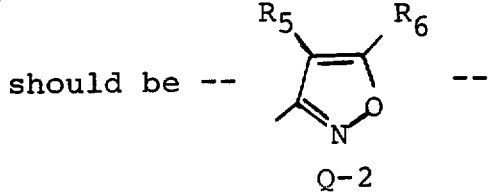

col. 63, line 50: 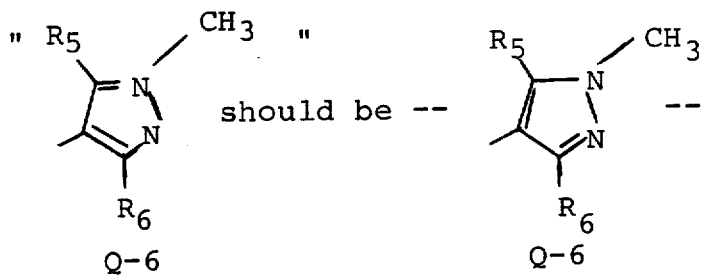

UNITED STATES PATENT AND TRADEMARK OFFICE
CERTIFICATE OF CORRECTION

PATENT NO. : 4,784,684

DATED : November 15, 1988

INVENTOR(S) : Morris Padgett Rorer

It is certified that error appears in the above-identified patent and that said Letters Patent is hereby corrected as shown below:

col. 63, line 55:

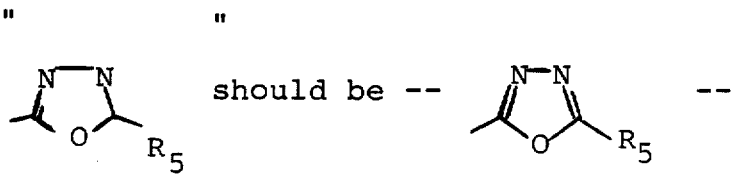

col. 64, line 62:

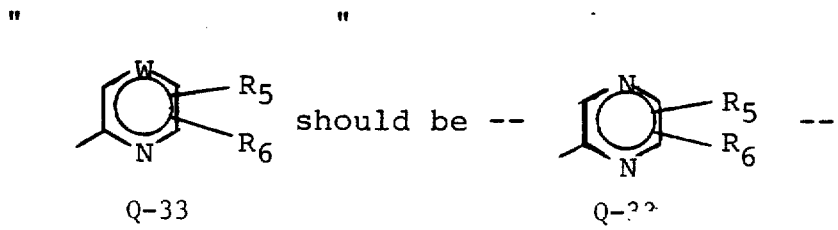

Signed and Sealed this

Seventeenth Day of April, 1990

Attest:

HARRY F. MANBECK, JR.

Attesting Officer

Commissioner of Patents and Trademarks